United States Patent
Yu et al.

(10) Patent No.: US 9,574,179 B2
(45) Date of Patent: *Feb. 21, 2017

(54) HEMATOPOIETIC PRECURSOR CELL PRODUCTION BY PROGRAMMING

(75) Inventors: Junying Yu, Madison, WI (US); Maksym A. Vodyanyk, Madison, WI (US)

(73) Assignee: Cellular Dynamics International, Inc., Madison, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/984,281

(22) PCT Filed: Feb. 7, 2012

(86) PCT No.: PCT/US2012/024098
§ 371 (c)(1),
(2), (4) Date: Oct. 18, 2013

(87) PCT Pub. No.: WO2012/109208
PCT Pub. Date: Aug. 16, 2012

(65) Prior Publication Data
US 2014/0037600 A1 Feb. 6, 2014

Related U.S. Application Data

(60) Provisional application No. 61/440,619, filed on Feb. 8, 2011.

(51) Int. Cl.
| | | |
|---|---|---|
| A01N 63/00 | (2006.01) | |
| A01N 65/00 | (2009.01) | |
| C12N 5/071 | (2010.01) | |
| C12N 5/00 | (2006.01) | |
| C12N 5/0789 | (2010.01) | |
| A61K 35/28 | (2015.01) | |

(52) U.S. Cl.
CPC .............. *C12N 5/0647* (2013.01); *A61K 35/28* (2013.01); *C12N 2501/60* (2013.01); *C12N 2501/999* (2013.01); *C12N 2506/02* (2013.01); *C12N 2506/45* (2013.01); *C12N 2510/00* (2013.01)

(58) Field of Classification Search
CPC ... C12N 5/0622; C12N 5/0639; C12N 5/0647; A61K 35/30; A61K 35/15; A61K 35/28
USPC ........................................................ 424/93.7
See application file for complete search history.

(56) References Cited

U.S. PATENT DOCUMENTS

| | | | |
|---|---|---|---|
| 8,546,140 B2 | 10/2013 | Mack | |
| 8,741,648 B2 | 6/2014 | Rajesh | |
| 2007/0048865 A1 | 3/2007 | Tani et al. | |
| 2008/0108044 A1 | 5/2008 | Rajesh et al. | |
| 2010/0150887 A1* | 6/2010 | Duff et al. | 424/93.21 |
| 2012/0009618 A1 | 1/2012 | Yu | |
| 2013/0189778 A1 | 7/2013 | Mack | |
| 2014/0038293 A1 | 2/2014 | Mack | |

FOREIGN PATENT DOCUMENTS

| | | |
|---|---|---|
| JP | 2006-149396 | 6/2006 |
| JP | PCT/JP2011/072234 | * 9/2011 |
| WO | WO 97/41224 | 11/1997 |
| WO | WO2010/099539 A1 | * 9/2010 |

OTHER PUBLICATIONS

Vodyanik et al 2005, Blood 105:617-626.*
Kaufman et al 2001, PNAS (USA) 98:10716-10721.*
Choi et al 2009, Life Sciences 85:39-45.*
Moreno-Gimeno et al 2010, FEBS Journal 277:5014-5025.*
Park et al 2010, Blood 116:5762-5772.*
Chang et al 2008, Taiwan J. Obstet. Gynecol. 47:422-430.*
Salanga et al 2010, Dev. Dyn 239:1178-1187.*
Chan et al 2007, Blood 109:1908-1915.*
Pimanda et al 2007, PNAS (USA) 104:17692-17697.*
Hosoya et al 2009, J. Exp. Med 206:2987-3000.*
Van der Meer 2010, Leukemia 24:1834-1843.*
Jiang et al 2010, Cytotechnology. 62:31-42.*
Choi et al., "Hematopoietic and Endothelial Differentiation of Human induced Pluripotent Stem Cells", *Stem Cells*, 27:559-567, 2008.
Kitajima et al., "GATA-2 and GATA-2/ER display opposing activities in the development and differentiation of blood progenitors", *The EMBO Journal*, 21(12):3060-3069, 2002.
Kitajima et al., "Redirecting differentiation of hematopoietic progenitors by a transcription factor, GATA-2", *Blood*, 107(5):1857-63, 2005.
Murphy et al., "Manipulation of Mouse Hematopoietic Progenitors by Specific Retroviral Infection", *The Journal of Biochemistry*, 278(44):43556-43563, 2003.
PCT International Preliminary Report on Patentability issued in International Application No. PCT/US2012/024098, mailed Aug. 22, 2013.
PCT International Search Report and Written Opinion issued in International Application No. PCT/US2012/024098, mailed Aug. 14, 2012.
Pimanda and Göttgens, "Gene regulatory networks governing haematopoietic stem cell development and identity", *Int J. Dev. Biol. Sci.*, 54:1201-11, 2010.
Szabo et al., "Direct conversion of human fibroblasts to multilineage blood progenitors", *Nature*, 468(7323):521-6, 2010.
Wilson et al., "The transcriptional program controlled by the stem cell leukemia gene Scl/Tal1 during early embryonic hematopoietic development", *Blood*, 113:5456-65, 2009.

(Continued)

*Primary Examiner* — Christopher M Babic
*Assistant Examiner* — Kelaginamane T Hiriyanna
(74) *Attorney, Agent, or Firm* — Parker Highlander PLLC

(57) ABSTRACT

The invention generally regards methods for providing hematopoietic cells and precursors of hematopoietic cells from a variety of cell sources, such as pluripotent stem cells or somatic cells. Also provided are therapeutic compositions including the provided hematopoietic cells and precursors of hematopoietic cells, and methods of using such for the treatment of subjects.

7 Claims, 7 Drawing Sheets

(56) References Cited

OTHER PUBLICATIONS

Zhu and Emerson, "Hematopoietic cytokines, transcription factors and lineage commitment", *Oncogene*, 21:3295-3313, 2002.
David et al., "Forward programming of pluripotent stem cells towards distinct cardiovascular cell types," *Cardiovascular Research*, 84:263-272, 2009.
Nikolova-Krstevski et al., "ERG is required for the differentiation of embryonic stem cells along the endothelial lineage," *BMC Developmental Biology*, 9:72, pp. 1-14, 2009.
Pillozzi et al., "HERG potassium channels are constitutively expressed in primary human acute myeloid leukemias and regulate cell proliferation of normal and leukemic hemopoietic progenitors," *Leukemia*, 16:1791-1798, 2002.
Kurita et al., "Tal1/Scl gene transduction using a lentiviral vector stimulates highly efficiency hematopoietic cell differentiation from common marmoset (*Callithrix jacchus*) embryonic stem cells," *Stem Cells*, 24:2014-2022, 2006.
Office Action issued in Japanese Application No. 2013-552725, mailed Jan. 5, 2016.
Chicha et al., "Human pluripotent stem cells differentiatied in fully defined medium generate hematopoietic CD34+ and CD34− progenitors with distinct characteristics," *PLoS ONE*, 6(2):e14733, 2011.
Dias et al., "Generation of red blood cells from human induced pluripotent stem cells," *Stem Cells and Development*, 20(9):1639-1647, 2011.
Extended European Search Report issued in European Application No. 12744365.3, mailed Oct. 31, 2014.
Grigoriadis et al., "Directed differentiation of hematopoietic precursors and functional osetoclasts from human ES and iPS cells," *Blood*, 115(14):2769-2776, 2010.
Office Action issued in European Application No. 12744365.3, mailed Mar. 2, 2016.
Shi et al., "Cooperative interaction of Etv2 and Gata2 regulates the development of endothelial and hematopoietic lineages," *Developmental Biology*, 389:208-218, 2014.

\* cited by examiner

SEQUENCE LISTING

```
<160> NUMBER OF SEQ ID NOS: 32

<210> SEQ ID NO 1
<211> LENGTH: 5042
<212> TYPE: DNA
<213> ORGANISM: Homo sapiens
<220> FEATURE:
<221> NAME/KEY: CDS
<222> LOCATION: (273)..(1661)

<400> SEQUENCE: 1
gttttcactt ggtcggaatg gggagagtgt gcaagagatc gctgcgggac aggttcctag      60
agatcgctcc gggacggtcg tgacggcccc cgagggacat gagagaagag gagcggcgct     120
caggttattc caggatcttt ggagacccga ggaaagccgt gttgaccaaa agcaagacaa     180
atgactcaca gagaaaaaag atggcagaac caagggcaac taaagccgtc aggttctgaa     240
cagctggtag atgggctggc ttactgaagg ac atg att cag act gtc ccg gac      293
                                   Met Ile Gln Thr Val Pro Asp
                                    1               5 cca gca gct cat atc aag gaa gcc tta tca gtt gtg agt gag gac cag       341
Pro Ala Ala His Ile Lys Glu Ala Leu Ser Val Val Ser Glu Asp Gln
            10              15                  20
```

```
tcg ttg ttt gag tgt gcc tac gga acg cca cac ctg gct aag aca gag      389
Ser Leu Phe Glu Cys Ala Tyr Gly Thr Pro His Leu Ala Lys Thr Glu
    25              30                  35 atg acc gcg tcc tcc tcc agc gac tat gga cag act tcc aag atg agc      437
Met Thr Ala Ser Ser Ser Asp Tyr Gly Gln Thr Ser Lys Met Ser
40              45                  50                  55 cca cgc gtc cct cag cag gat tgg ctg tct caa ccc cca gcc agg gtc      485
Pro Arg Val Pro Gln Gln Asp Trp Leu Ser Gln Pro Pro Ala Arg Val
                    60                  65                  70 acc atc aaa atg gaa tgt aac cct agc cag gtg aat ggc tca agg aac      533
Thr Ile Lys Met Glu Cys Asn Pro Ser Gln Val Asn Gly Ser Arg Asn
        75                  80                  85 tct cct gat gaa tgc agt gtg gcc aaa ggc ggg aag atg gtg ggc agc      581
Ser Pro Asp Glu Cys Ser Val Ala Lys Gly Gly Lys Met Val Gly Ser
            90                  95                  100 cca gac acc gtt ggg atg aac tac ggc agc tac atg gag gag aag cac      629
Pro Asp Thr Val Gly Met Asn Tyr Gly Ser Tyr Met Glu Glu Lys His
        105                 110                 115 atg cca ccc cca aac atg acc acg aac gag cgc aga gtt atc gtg cca      677
Met Pro Pro Pro Asn Met Thr Thr Asn Glu Arg Arg Val Ile Val Pro
120                 125                 130                 135 gca gat cct acg cta tgg agt aca gac cat gtg cgg cag tgg ctg gag      725
Ala Asp Pro Thr Leu Trp Ser Thr Asp His Val Arg Gln Trp Leu Glu
                140                 145                 150 tgg gcg gtg aaa gaa tat ggc ctt cca gac gtc aac atc ttg tta ttc      773
Trp Ala Val Lys Glu Tyr Gly Leu Pro Asp Val Asn Ile Leu Leu Phe
            155                 160                 165 cag aac atc gat ggg aag gaa ctg tgc aag atg acc aag gac gac ttc      821
Gln Asn Ile Asp Gly Lys Glu Leu Cys Lys Met Thr Lys Asp Asp Phe
        170                 175                 180 cag agg ctc acc ccc agc tac aac gcc gac atc ctt ctc tca cat ctc      869
Gln Arg Leu Thr Pro Ser Tyr Asn Ala Asp Ile Leu Leu Ser His Leu
    185                 190                 195 cac tac ctc aga gag act cct ctt cca cat ttg act tca gat gat gtt      917
His Tyr Leu Arg Glu Thr Pro Leu Pro His Leu Thr Ser Asp Asp Val
200                 205                 210                 215 gat aaa gcc tta caa aac tct cca cgg tta atg cat gct aga aac aca      965
Asp Lys Ala Leu Gln Asn Ser Pro Arg Leu Met His Ala Arg Asn Thr
                220                 225                 230 gat tta cca tat gag ccc ccc agg aga tca gcc tgg acc ggt cac ggc     1013
Asp Leu Pro Tyr Glu Pro Pro Arg Arg Ser Ala Trp Thr Gly His Gly
            235                 240                 245 cac ccc acg ccc cag tcg aaa gct gct caa cca tct cct tcc aca gtg     1061
His Pro Thr Pro Gln Ser Lys Ala Ala Gln Pro Ser Pro Ser Thr Val
        250                 255                 260 ccc aaa act gaa gac cag cgt cct cag tta gat cct tat cag att ctt     1109
Pro Lys Thr Glu Asp Gln Arg Pro Gln Leu Asp Pro Tyr Gln Ile Leu
    265                 270                 275 gga cca aca agt agc cgc ctt gca aat cca ggc agt ggc cag atc cag     1157
Gly Pro Thr Ser Ser Arg Leu Ala Asn Pro Gly Ser Gly Gln Ile Gln
280                 285                 290                 295 ctt tgg cag ttc ctc ctg gag ctc ctg tcg gac agc tcc aac tcc agc     1205
Leu Trp Gln Phe Leu Leu Glu Leu Leu Ser Asp Ser Ser Asn Ser Ser
                300                 305                 310 tgc atc acc tgg gaa ggc acc aac ggg gag ttc aag atg acg gat ccc     1253
Cys Ile Thr Trp Glu Gly Thr Asn Gly Glu Phe Lys Met Thr Asp Pro
            315                 320                 325 gac gag gtg gcc cgg cgc tgg gga gag cgg aag agc aaa ccc aac atg     1301
Asp Glu Val Ala Arg Arg Trp Gly Glu Arg Lys Ser Lys Pro Asn Met
        330                 335                 340
```

```
aac tac gat aag ctc agc cgc gcc ctc cgt tac tac tat gac aag aac      1349
Asn Tyr Asp Lys Leu Ser Arg Ala Leu Arg Tyr Tyr Tyr Asp Lys Asn
345                 350                 355 atc atg acc aag gtc cat ggg aag cgc tac gcc tac aag ttc gac ttc      1397
Ile Met Thr Lys Val His Gly Lys Arg Tyr Ala Tyr Lys Phe Asp Phe
360                 365                 370                 375 cac ggg atc gcc cag gcc ctc cag ccc cac ccc ccg gag tca tct ctg      1445
His Gly Ile Ala Gln Ala Leu Gln Pro His Pro Pro Glu Ser Ser Leu
            380                 385                 390 tac aag tac ccc tca gac ctc ccg tac atg ggc tcc tat cac gcc cac      1493
Tyr Lys Tyr Pro Ser Asp Leu Pro Tyr Met Gly Ser Tyr His Ala His
            395                 400                 405 cca cag aag atg aac ttt gtg gcg ccc cac cct cca gcc ctc ccc gtg      1541
Pro Gln Lys Met Asn Phe Val Ala Pro His Pro Pro Ala Leu Pro Val
            410                 415                 420 aca tct tcc agt ttt ttt gct gcc cca aac cca tac tgg aat tca cca      1589
Thr Ser Ser Ser Phe Phe Ala Ala Pro Asn Pro Tyr Trp Asn Ser Pro
            425                 430                 435 act ggg ggt ata tac ccc aac act agg ctc ccc acc agc cat atg cct      1637
Thr Gly Gly Ile Tyr Pro Asn Thr Arg Leu Pro Thr Ser His Met Pro
440                 445                 450                 455 tct cat ctg ggc act tac tac taa agacctggcg gaggcttttc ccatcagcgt     1691
Ser His Leu Gly Thr Tyr Tyr
            460 gcattcacca gcccatcgcc acaaactcta tcggagaaca tgaatcaaaa gtgcctcaag    1751 aggaatgaaa aaagctttac tggggctggg gaaggaagcc ggggaagaga tccaaagact    1811 cttgggaggg agttactgaa gtcttactac agaaatgagg aggatgctaa aaatgtcacg    1871 aatatggaca tatcatctgt ggactgacct tgtaaaagac agtgtatgta gaagcatgaa    1931 gtcttaagga caaagtgcca agaaagtgg tcttaagaaa tgtataaact ttagagtaga    1991 gtttggaatc ccactaatgc aaactgggat gaaactaaag caatagaaac aacacagttt    2051 tgacctaaca taccgtttat aatgccattt taaggaaaac tacctgtatt taaaaatага    2111 aacatatcaa aaacaagaga aaagacacga gagagactgt ggcccatcaa cagacgttga    2171 tatgcaactg catggcatgt gctgttttgg ttgaaatcaa atacattccg tttgatggac    2231 agctgtcagc tttctcaaac tgtgaagatg acccaaagtt tccaactcct ttacagtatt    2291 accgggacta tgaactaaaa ggtgggactg aggatgtgta tagagtgagc gtgtgattgt    2351 agacagaggg gtgaagaagg aggaggaaga ggcagagaag gaggagacca gggctgggaa    2411 agaaacttct caagcaatga agactggact caggacattt ggggactgtg tacaatgagt    2471 tatggagact cgagggttca tgcagtcagt gttataccaa acccagtgtt aggagaaagg    2531 acacagcgta atggagaaag gggaagtagt agaattcaga aacaaaaatg cgcatctctt    2591 tctttgtttg tcaaatgaaa attttaactg gaattgtctg atatttaaga gaaacattca    2651 ggacctcatc attatgtggg ggctttgttc tccacagggt caggtaagag atggccttct    2711 tggctgccac aatcagaaat cacgcaggca ttttgggtag gcggcctcca gttttccttt    2771 gagtcgcgaa cgctgtgcgt ttgtcagaat gaagtataca agtcaatgtt tttccccctt    2831 tttatataat aattatataa cttatgcatt tatacactac gagttgatct cggccagcca    2891 aagacacacg acaaaagaga caatcgatat aatgtggcct tgaattttaa ctctgtatgc    2951 ttaatgttta caatatgaag ttattagttc ttagaatgca gaatgtatgt aataaaataa    3011 gcttggccta gcatggcaaa tcagatttat acaggagtct gcatttgcac tttttttagt    3071 gactaaagtt gcttaatgaa acatgtgct gaatgttgtg gattttgtgt tataatttac     3131
```

-continued

```
tttgtccagg aacttgtgca agggagagcc aaggaaatag gatgtttggc acccaaatgg    3191
cgtcagcctc tccaggtcct tcttgcctcc cctcctgtct tttatttcta gccccttttg    3251
gaacagaagg accccggggtt tcacattgga gcctccatat ttatgcctgg aatggaaaga    3311
ggcctatgaa gctggggttg tcattgagaa attctagttc agcacctggt cacaaatcac    3371
ccttaattcc tgctatgatt aaaatacatt tgttgaacag tgaacaagct accactcgta    3431
aggcaaactg tattattact ggcaaataaa gcgtcatgga tagctgcaat ttctcacttt    3491
acagaaacaa gggataacgt ctagatttgc tgcggggttt ctctttcagg agctctcact    3551
aggtagacag ctttagtcct gctacatcag agttacctgg gcactgtggc ttgggattca    3611
ctagccctga gcctgatgtt gctggctatc ccttgaagac aatgtttatt tccataatct    3671
agagtcagtt ccctgggca tcttttcttt gaatcacaaa tgctgccaac cttggtccag    3731
gtgaaggcaa ctcaaaaggt gaaaatacaa ggtgaccgtg cgaaggcgct agccgaaaca    3791
tcttagctga ataggtttct gaactggccc ttttcatagc tgtttcaggg cctgtttttt    3851
tcacgttgca gtccttttgc tatgattatg tgaagttgcc aaacctctgt gctgtggatg    3911
ttttggcagt gggctttgaa gtcggcagga cacgattacc aatgctcctg acaccccgtg    3971
tcatttggat tagacggagc ccaaccatcc atcattttgc agcagcctgg gaaggcccac    4031
aaagtgcccg tatctcctta gggaaaataa ataaatacaa tcatgaaagc tggcagttag    4091
gctgacccaa actgtgctaa tggaaaagat cagtcatttt tattttggaa tgcaaagtca    4151
agacacacct acattcttca tagaaataca catttacttg gataatcact cagttctctc    4211
ttcaagactg tctcatgagc aagatcataa aaacaagaca tgattatcat attcaatttt    4271
aacagatgtt ttccattaga tccctcaacc ctccaccccc agtccaggtt attagcaagt    4331
cttatgagca actgggataa ttttggataa catgataata ctgagttcct tcaaatacat    4391
aattcttaaa ttgttttcaaa atggcattaa ctctctgtta ctgttgtaat ctaattccaa    4451
agcccccctcc aggtcatatt cataattgca tgaacctttt ctctctgttt gtccctgtct    4511
cttggcttgc cctgatgtat actcagactc ctgtacaatc ttactcctgc tggcaagaga    4571
tttgtcttct tttcttgtct tcaattggct ttcgggcctt gtatgtggta aaatcaccaa    4631
atcacagtca agactgtgtt tttgttccta gtttgatgcc cttatgtccc ggaggggttc    4691
acaaagtgct ttgtcaggac tgctgcagtt agaaggctca ctgcttctcc taagccttct    4751
gcacagatgt ggcacctgca acccaggagc aggagccgga ggagctgccc tctgacagca    4811
ggtgcagcag agatggctac agctcaggag ctgggaaggt gatggggcac agggaaagca    4871
cagatgttct gcagcgcccc aaagtgaccc attgcctgga gaaagagaag aaaatatttt    4931
ttaaaaagct agtttattta gcttctcatt aattcattca aataaagtcg tgaggtgact    4991
aattagagaa taaaaattac tttggactac tcaaaaatac ccaaaaaaa a              5042
```

<210> SEQ ID NO 2
<211> LENGTH: 462
<212> TYPE: PRT
<213> ORGANISM: Homo sapiens

<400> SEQUENCE: 2

Met Ile Gln Thr Val Pro Asp Pro Ala Ala His Ile Lys Glu Ala Leu
1               5                   10                  15

Ser Val Val Ser Glu Asp Gln Ser Leu Phe Glu Cys Ala Tyr Gly Thr
            20                  25                  30

-continued

```
Pro His Leu Ala Lys Thr Glu Met Thr Ala Ser Ser Ser Asp Tyr
        35                  40                  45
Gly Gln Thr Ser Lys Met Ser Pro Arg Val Pro Gln Gln Asp Trp Leu
 50                  55                  60
Ser Gln Pro Pro Ala Arg Val Thr Ile Lys Met Glu Cys Asn Pro Ser
 65                  70                  75                  80
Gln Val Asn Gly Ser Arg Asn Ser Pro Asp Glu Cys Ser Val Ala Lys
                 85                  90                  95
Gly Gly Lys Met Val Gly Ser Pro Asp Thr Val Gly Met Asn Tyr Gly
            100                 105                 110
Ser Tyr Met Glu Glu Lys His Met Pro Pro Asn Met Thr Thr Asn
            115                 120                 125
Glu Arg Arg Val Ile Val Pro Ala Asp Pro Thr Leu Trp Ser Thr Asp
130                 135                 140
His Val Arg Gln Trp Leu Glu Trp Ala Val Lys Glu Tyr Gly Leu Pro
145                 150                 155                 160
Asp Val Asn Ile Leu Leu Phe Gln Asn Ile Asp Gly Lys Glu Leu Cys
                165                 170                 175
Lys Met Thr Lys Asp Asp Phe Gln Arg Leu Thr Pro Ser Tyr Asn Ala
            180                 185                 190
Asp Ile Leu Leu Ser His Leu His Tyr Leu Arg Glu Thr Pro Leu Pro
            195                 200                 205
His Leu Thr Ser Asp Asp Val Asp Lys Ala Leu Gln Asn Ser Pro Arg
        210                 215                 220
Leu Met His Ala Arg Asn Thr Asp Leu Pro Tyr Glu Pro Pro Arg Arg
225                 230                 235                 240
Ser Ala Trp Thr Gly His Gly His Pro Thr Pro Gln Ser Lys Ala Ala
                245                 250                 255
Gln Pro Ser Pro Ser Thr Val Pro Lys Thr Glu Asp Gln Arg Pro Gln
            260                 265                 270
Leu Asp Pro Tyr Gln Ile Leu Gly Pro Thr Ser Ser Arg Leu Ala Asn
        275                 280                 285
Pro Gly Ser Gly Gln Ile Gln Leu Trp Gln Phe Leu Leu Glu Leu Leu
290                 295                 300
Ser Asp Ser Ser Asn Ser Ser Cys Ile Thr Trp Glu Gly Thr Asn Gly
305                 310                 315                 320
Glu Phe Lys Met Thr Asp Pro Asp Glu Val Ala Arg Arg Trp Gly Glu
                325                 330                 335
Arg Lys Ser Lys Pro Asn Met Asn Tyr Asp Lys Leu Ser Arg Ala Leu
            340                 345                 350
Arg Tyr Tyr Tyr Asp Lys Asn Ile Met Thr Lys Val His Gly Lys Arg
        355                 360                 365
Tyr Ala Tyr Lys Phe Asp Phe His Gly Ile Ala Gln Ala Leu Gln Pro
370                 375                 380
His Pro Pro Glu Ser Ser Leu Tyr Lys Tyr Pro Ser Asp Leu Pro Tyr
385                 390                 395                 400
Met Gly Ser Tyr His Ala His Pro Gln Lys Met Asn Phe Val Ala Pro
                405                 410                 415
His Pro Pro Ala Leu Pro Val Thr Ser Ser Ser Phe Phe Ala Ala Pro
            420                 425                 430
```

```
Asn Pro Tyr Trp Asn Ser Pro Thr Gly Gly Ile Tyr Pro Asn Thr Arg
        435                 440                 445

Leu Pro Thr Ser His Met Pro Ser His Leu Gly Thr Tyr Tyr
    450                 455                 460

<210> SEQ ID NO 3
<211> LENGTH: 5114
<212> TYPE: DNA
<213> ORGANISM: Homo sapiens
<220> FEATURE:
<221> NAME/KEY: CDS
<222> LOCATION: (273)..(1733)

<400> SEQUENCE: 3
gttttcactt ggtcggaatg gggagagtgt gcaagagatc gctgcgggac aggttcctag     60
agatcgctcc gggacggtcg tgacggcccc cgagggacat gagagaagag gagcggcgct    120
caggttattc aggatctttt ggagacccga ggaaagccgt gttgaccaaa agcaagacaa    180
atgactcaca gagaaaaaag atggcagaac caagggcaac taaagccgtc aggttctgaa    240
cagctggtag atgggctggc ttactgaagg ac atg att cag act gtc ccg gac      293
                                   Met Ile Gln Thr Val Pro Asp
                                     1               5 cca gca gct cat atc aag gaa gcc tta tca gtt gtg agt gag gac cag      341
Pro Ala Ala His Ile Lys Glu Ala Leu Ser Val Val Ser Glu Asp Gln
            10                  15                  20 tcg ttg ttt gag tgt gcc tac gga acg cca cac ctg gct aag aca gag      389
Ser Leu Phe Glu Cys Ala Tyr Gly Thr Pro His Leu Ala Lys Thr Glu
    25                  30                  35 atg acc gcg tcc tcc tcc agc gac tat gga cag act tcc aag atg agc      437
Met Thr Ala Ser Ser Ser Ser Asp Tyr Gly Gln Thr Ser Lys Met Ser
40                  45                  50                  55 cca cgc gtc cct cag cag gat tgg ctg tct caa ccc cca gcc agg gtc      485
Pro Arg Val Pro Gln Gln Asp Trp Leu Ser Gln Pro Pro Ala Arg Val
                60                  65                  70 acc atc aaa atg gaa tgt aac cct agc cag gtg aat ggc tca agg aac      533
Thr Ile Lys Met Glu Cys Asn Pro Ser Gln Val Asn Gly Ser Arg Asn
            75                  80                  85 tct cct gat gaa tgc agt gtg gcc aaa ggc ggg aag atg gtg ggc agc      581
Ser Pro Asp Glu Cys Ser Val Ala Lys Gly Gly Lys Met Val Gly Ser
    90                  95                 100 cca gac acc gtt ggg atg aac tac ggc agc tac atg gag gag aag cac      629
Pro Asp Thr Val Gly Met Asn Tyr Gly Ser Tyr Met Glu Glu Lys His
105                 110                 115 atg cca ccc caa aac atg acc acg aac gag cgc aga gtt atc gtg cca      677
Met Pro Pro Pro Asn Met Thr Thr Asn Glu Arg Arg Val Ile Val Pro
120                 125                 130                 135 gca gat cct acg cta tgg agt aca gac cat gtg cgg cag tgg ctg gag      725
Ala Asp Pro Thr Leu Trp Ser Thr Asp His Val Arg Gln Trp Leu Glu
                140                 145                 150 tgg gcg gtg aaa gaa tat ggc ctt cca gac gtc aac atc ttg tta ttc      773
Trp Ala Val Lys Glu Tyr Gly Leu Pro Asp Val Asn Ile Leu Leu Phe
            155                 160                 165 cag aac atc gat ggg aag gaa ctg tgc aag atg acc aag gac gac ttc      821
Gln Asn Ile Asp Gly Lys Glu Leu Cys Lys Met Thr Lys Asp Asp Phe
    170                 175                 180 cag agg ctc acc ccc agc tac aac gcc gac atc ctt ctc tca cat ctc      869
Gln Arg Leu Thr Pro Ser Tyr Asn Ala Asp Ile Leu Leu Ser His Leu
185                 190                 195
```

| | | |
|---|---|---|
| cac tac ctc aga gag act cct ctt cca cat ttg act tca gat gat gtt<br>His Tyr Leu Arg Glu Thr Pro Leu Pro His Leu Thr Ser Asp Asp Val<br>200                     205                          210                     215 | | 917 |
| gat aaa gcc tta caa aac tct cca cgg tta atg cat gct aga aac aca<br>Asp Lys Ala Leu Gln Asn Ser Pro Arg Leu Met His Ala Arg Asn Thr<br>                   220                          225                     230 | | 965 |
| ggg ggt gca gct ttt att ttc cca aat act tca gta tat cct gaa gct<br>Gly Gly Ala Ala Phe Ile Phe Pro Asn Thr Ser Val Tyr Pro Glu Ala<br>                235                          240                     245 | | 1013 |
| acg caa aga att aca act agg cca gat tta cca tat gag ccc ccc agg<br>Thr Gln Arg Ile Thr Thr Arg Pro Asp Leu Pro Tyr Glu Pro Pro Arg<br>         250                          255                     260 | | 1061 |
| aga tca gcc tgg acc ggt cac ggc cac ccc acg ccc cag tcg aaa gct<br>Arg Ser Ala Trp Thr Gly His Gly His Pro Thr Pro Gln Ser Lys Ala<br>265                     270                          275 | | 1109 |
| gct caa cca tct cct tcc aca gtg ccc aaa act gaa gac cag cgt cct<br>Ala Gln Pro Ser Pro Ser Thr Val Pro Lys Thr Glu Asp Gln Arg Pro<br>280                     285                          290                     295 | | 1157 |
| cag tta gat cct tat cag att ctt gga cca aca agt agc cgc ctt gca<br>Gln Leu Asp Pro Tyr Gln Ile Leu Gly Pro Thr Ser Ser Arg Leu Ala<br>                             300                          305                     310 | | 1205 |
| aat cca ggc agt ggc cag atc cag ctt tgg cag ttc ctc ctg gag ctc<br>Asn Pro Gly Ser Gly Gln Ile Gln Leu Trp Gln Phe Leu Leu Glu Leu<br>                315                          320                     325 | | 1253 |
| ctg tcg gac agc tcc aac tcc agc tgc atc acc tgg gaa ggc acc aac<br>Leu Ser Asp Ser Ser Asn Ser Ser Cys Ile Thr Trp Glu Gly Thr Asn<br>         330                          335                     340 | | 1301 |
| ggg gag ttc aag atg acg gat ccc gac gag gtg gcc cgg cgc tgg gga<br>Gly Glu Phe Lys Met Thr Asp Pro Asp Glu Val Ala Arg Arg Trp Gly<br>345                     350                          355 | | 1349 |
| gag cgg aag agc aaa ccc aac atg aac tac gat aag ctc agc cgc gcc<br>Glu Arg Lys Ser Lys Pro Asn Met Asn Tyr Asp Lys Leu Ser Arg Ala<br>360                     365                          370                     375 | | 1397 |
| ctc cgt tac tac tat gac aag aac atc atg acc aag gtc cat ggg aag<br>Leu Arg Tyr Tyr Tyr Asp Lys Asn Ile Met Thr Lys Val His Gly Lys<br>                             380                          385                     390 | | 1445 |
| cgc tac gcc tac aag ttc gac ttc cac ggg atc gcc cag gcc ctc cag<br>Arg Tyr Ala Tyr Lys Phe Asp Phe His Gly Ile Ala Gln Ala Leu Gln<br>                395                          400                     405 | | 1493 |
| ccc cac ccc ccg gag tca tct ctg tac aag tac ccc tca gac ctc ccg<br>Pro His Pro Pro Glu Ser Ser Leu Tyr Lys Tyr Pro Ser Asp Leu Pro<br>         410                          415                     420 | | 1541 |
| tac atg ggc tcc tat cac gcc cac cca cag aag atg aac ttt gtg gcg<br>Tyr Met Gly Ser Tyr His Ala His Pro Gln Lys Met Asn Phe Val Ala<br>425                     430                          435 | | 1589 |
| ccc cac cct cca gcc ctc ccc gtg aca tct tcc agt ttt ttt gct gcc<br>Pro His Pro Pro Ala Leu Pro Val Thr Ser Ser Ser Phe Phe Ala Ala<br>440                     445                          450                     455 | | 1637 |
| cca aac cca tac tgg aat tca cca act ggg ggt ata tac ccc aac act<br>Pro Asn Pro Tyr Trp Asn Ser Pro Thr Gly Gly Ile Tyr Pro Asn Thr<br>                     460                          465                     470 | | 1685 |
| agg ctc ccc acc agc cat atg cct tct cat ctg ggc act tac tac taa<br>Arg Leu Pro Thr Ser His Met Pro Ser His Leu Gly Thr Tyr Tyr<br>                475                          480                     485 | | 1733 |
| agacctggcg gaggcttttc ccatcagcgt gcattcacca gcccatcgcc acaaactcta | | 1793 |
| tcggagaaca tgaatcaaaa gtgcctcaag aggaatgaaa aaagctttac tggggctggg | | 1853 |
| gaaggaagcc ggggaagaga tccaaagact cttgggaggg agttactgaa gtcttactac | | 1913 |
| agaaatgagg aggatgctaa aaatgtcacg aatatggaca tatcatctgt ggactgacct | | 1973 |

```
tgtaaaagac agtgtatgta gaagcatgaa gtcttaagga caaagtgcca aagaaagtgg    2033
tcttaagaaa tgtataaact ttagagtaga gtttggaatc ccactaatgc aaactgggat    2093
gaaactaaag caatagaaac aacacagttt tgacctaaca taccgtttat aatgccattt    2153
taaggaaaac tacctgtatt taaaaataga aacatatcaa aaacaagaga aaagacacga    2213
gagagactgt ggcccatcaa cagacgttga tatgcaactg catggcatgt gctgttttgg    2273
ttgaaatcaa atacattccg tttgatggac agctgtcagc tttctcaaac tgtgaagatg    2333
acccaaagtt tccaactcct ttacagtatt accgggacta tgaactaaaa ggtgggactg    2393
aggatgtgta tagagtgagc gtgtgattgt agacagaggg gtgaagaagg aggaggaaga    2453
ggcagagaag gaggagacca gggctgggaa agaaacttct caagcaatga agactggact    2513
caggacattt ggggactgtg tacaatgagt tatggagact cgagggttca tgcagtcagt    2573
gttataccaa acccagtgtt aggagaaagg acacagcgta atggagaaag gggaagtagt    2633
agaattcaga aacaaaaatg cgcatctctt tctttgtttg tcaaatgaaa attttaactg    2693
gaattgtctg atatttaaga gaaacattca ggacctcatc attatgtggg ggctttgttc    2753
tccacagggt caggtaagag atggccttct tggctgccac aatcagaaat cacgcaggca    2813
ttttgggtag gcggcctcca gttttccttt gagtcgcgaa cgctgtgcgt ttgtcagaat    2873
gaagtataca agtcaatgtt tttccccctt tttatataat aattatataa cttatgcatt    2933
tatacactac gagttgatct cggccagcca aagcacacg acaaaagaga caatcgatat    2993
aatgtggcct tgaattttaa ctctgtatgc ttaatgttta caatatgaag ttattagttc    3053
ttagaatgca gaatgtatgt aataaaataa gcttggccta gcatggcaaa tcagatttat    3113
acaggagtct gcatttgcac tttttttagt gactaaagtt gcttaatgaa aacatgtgct    3173
gaatgttgtg gattttgtgt tataatttac tttgtccagg aacttgtgca agggagagcc    3233
aaggaaatag gatgtttggc acccaaatgg cgtcagcctc tccaggtcct tcttgcctcc    3293
cctcctgtct tttatttcta gcccctttt g gaacagaagg accccgggtt tcacattgga    3353
gcctccatat ttatgcctgg aatggaaaga ggcctatgaa gctggggttg tcattgagaa    3413
attctagttc agcaccctggt cacaaatcac ccttaattcc tgctatgatt aaaatacatt    3473
tgttgaacag tgaacaagct accactcgta aggcaaactg tattattact ggcaaataaa    3533
gcgtcatgga tagctgcaat ttctcacttt acagaaacaa gggataacgt ctagatttgc    3593
tgcgggtttt ctcttttcagg agctctcact aggtagacag ctttagtcct gctacatcag    3653
agttacctgg gcactgtggc ttgggattca ctagccctga gcctgatgtt gctggctatc    3713
ccttgaagac aatgtttatt tccataatct agagtcagtt ccctgggca tcttttcttt    3773 gaatcacaaa tgctgccaac cttggtccag gtgaaggcaa ctcaaaaggt gaaaatacaa    3833
ggtgaccgtg cgaaggcgct agccgaaaca tcttagctga ataggtttct gaactggccc    3893
ttttcatagc tgtttcaggg cctgttttt t tcacgttgca gtccttttgc tatgattatg    3953
tgaagttgcc aaacctctgt gctgtggatg ttttggcagt gggctttgaa gtcggcagga    4013
cacgattacc aatgctcctg acaccccgtg tcatttggat tagacggagc ccaaccatcc    4073
atcattttgc agcagcctgg gaaggcccac aaagtgcccg tatctcctta gggaaaataa    4133
ataaatacaa tcatgaaagc tggcagttag gctgacccaa actgtgctaa tggaaaagat    4193
cagtcatttt tatttggaa tgcaaagtca agacacacct acattcttca tagaaataca    4253
catttacttg gataatcact cagttctctc ttcaagactc tctcatgagc aagatcataa    4313
aaacaagaca tgattatcat attcaatttt aacagatgtt ttccattaga tccctcaacc    4373
```

```
ctccaccccc agtccaggtt attagcaagt cttatgagca actgggataa ttttggataa      4433
catgataata ctgagttcct tcaaatacat aattcttaaa ttgtttcaaa atggcattaa      4493
ctctctgtta ctgttgtaat ctaattccaa agcccctcc aggtcatatt cataattgca       4553
tgaacctttt ctctctgttt gtccctgtct cttggcttgc cctgatgtat actcagactc      4613
ctgtacaatc ttactcctgc tggcaagaga tttgtcttct tttcttgtct tcaattggct      4673
ttcgggcctt gtatgtggta aaatcaccaa atcacagtca agactgtgtt tttgttccta      4733
gtttgatgcc cttatgtccc ggaggggttc acaaagtgct tgtcaggac tgctgcagtt       4793
agaaggctca ctgcttctcc taagccttct gcacagatgt ggcacctgca acccaggagc      4853
aggagccgga ggagctgccc tctgacagca ggtgcagcag agatggctac agctcaggag      4913
ctggaaggt gatggggcac agggaaagca cagatgttct gcagcgcccc aaagtgaccc       4973
attgcctgga gaaagagaag aaaatatttt ttaaaaagct agtttattta gcttctcatt      5033
aattcattca aataaagtcg tgaggtgact aattagagaa taaaaattac tttggactac      5093
tcaaaaatac accaaaaaaa a                                                5114
```

<210> SEQ ID NO 4
<211> LENGTH: 486
<212> TYPE: PRT
<213> ORGANISM: Homo sapiens

<400> SEQUENCE: 4

```
Met Ile Gln Thr Val Pro Asp Pro Ala Ala His Ile Lys Glu Ala Leu
1               5                  10                  15

Ser Val Val Ser Glu Asp Gln Ser Leu Phe Glu Cys Ala Tyr Gly Thr
            20                  25                  30

Pro His Leu Ala Lys Thr Glu Met Thr Ala Ser Ser Ser Ser Asp Tyr
        35                  40                  45

Gly Gln Thr Ser Lys Met Ser Pro Arg Val Pro Gln Gln Asp Trp Leu
    50                  55                  60

Ser Gln Pro Pro Ala Arg Val Thr Ile Lys Met Glu Cys Asn Pro Ser
65                  70                  75                  80

Gln Val Asn Gly Ser Arg Asn Ser Pro Asp Glu Cys Ser Val Ala Lys
                85                  90                  95

Gly Gly Lys Met Val Gly Ser Pro Asp Thr Val Gly Met Asn Tyr Gly
            100                 105                 110

Ser Tyr Met Glu Glu Lys His Met Pro Pro Asn Met Thr Thr Asn
        115                 120                 125

Glu Arg Arg Val Ile Val Pro Ala Asp Pro Thr Leu Trp Ser Thr Asp
    130                 135                 140

His Val Arg Gln Trp Leu Glu Trp Ala Val Lys Glu Tyr Gly Leu Pro
145                 150                 155                 160

Asp Val Asn Ile Leu Leu Phe Gln Asn Ile Asp Gly Lys Glu Leu Cys
                165                 170                 175

Lys Met Thr Lys Asp Asp Phe Gln Arg Leu Thr Pro Ser Tyr Asn Ala
            180                 185                 190

Asp Ile Leu Leu Ser His Leu His Tyr Leu Arg Glu Thr Pro Leu Pro
        195                 200                 205

His Leu Thr Ser Asp Asp Val Asp Lys Ala Leu Gln Asn Ser Pro Arg
    210                 215                 220

Leu Met His Ala Arg Asn Thr Gly Gly Ala Ala Phe Ile Phe Pro Asn
225                 230                 235                 240
```

-continued

```
Thr Ser Val Tyr Pro Glu Ala Thr Gln Arg Ile Thr Thr Arg Pro Asp
            245                 250                 255

Leu Pro Tyr Glu Pro Pro Arg Arg Ser Ala Trp Thr Gly His Gly His
        260                 265                 270

Pro Thr Pro Gln Ser Lys Ala Ala Gln Pro Ser Pro Ser Thr Val Pro
    275                 280                 285

Lys Thr Glu Asp Gln Arg Pro Gln Leu Asp Pro Tyr Gln Ile Leu Gly
290                 295                 300

Pro Thr Ser Ser Arg Leu Ala Asn Pro Gly Ser Gly Gln Ile Gln Leu
305                 310                 315                 320

Trp Gln Phe Leu Leu Glu Leu Leu Ser Asp Ser Ser Asn Ser Ser Cys
                325                 330                 335

Ile Thr Trp Glu Gly Thr Asn Gly Glu Phe Lys Met Thr Asp Pro Asp
            340                 345                 350

Glu Val Ala Arg Arg Trp Gly Glu Arg Lys Ser Lys Pro Asn Met Asn
        355                 360                 365

Tyr Asp Lys Leu Ser Arg Ala Leu Arg Tyr Tyr Tyr Asp Lys Asn Ile
    370                 375                 380

Met Thr Lys Val His Gly Lys Arg Tyr Ala Tyr Lys Phe Asp Phe His
385                 390                 395                 400

Gly Ile Ala Gln Ala Leu Gln Pro His Pro Glu Ser Ser Leu Tyr
                405                 410                 415

Lys Tyr Pro Ser Asp Leu Pro Tyr Met Gly Ser Tyr His Ala His Pro
            420                 425                 430

Gln Lys Met Asn Phe Val Ala Pro His Pro Pro Ala Leu Pro Val Thr
        435                 440                 445

Ser Ser Ser Phe Phe Ala Ala Pro Asn Pro Tyr Trp Asn Ser Pro Thr
    450                 455                 460

Gly Gly Ile Tyr Pro Asn Thr Arg Leu Pro Thr Ser His Met Pro Ser
465                 470                 475                 480

His Leu Gly Thr Tyr Tyr
                485

<210> SEQ ID NO 5
<211> LENGTH: 3993
<212> TYPE: DNA
<213> ORGANISM: Homo sapiens
<220> FEATURE:
<221> NAME/KEY: CDS
<222> LOCATION: (342)..(1700)

<400> SEQUENCE: 5
agaagagaga ggagagctcg aggcgagaga gagagagaga gagagagaga     60
gagagagaga gagagatagg acttcctccc cgattcgcaa agtgaagtca cttcccaaaa     120
ttagctgaaa aaaagtttc atccggttaa ctgtctcttt cgctccgcta caacaacaaa     180
cgtgcacagg ggagtgaggg cagggcgctc gcaggggca cgcagggagg gcccagggcg     240
ccagggaggc cgcgccgggc taatccgaag gggctgcgag gtcaggctgt aaccgggtca     300
atgtgtggaa tattgggggg ctcggctgca gacttggcc a atg gac ggg act att     356
                                            Met Asp Gly Thr Ile
                                              1               5 aag gag gct ctg tcg gtg gtg agc gac gac cag tcc ctc ttt gac tca     404
Lys Glu Ala Leu Ser Val Val Ser Asp Asp Gln Ser Leu Phe Asp Ser
         10                  15                  20
```

|     |     |     |     |     |     |     |     |     |     |     |     |     |     |     |     |      |
|-----|-----|-----|-----|-----|-----|-----|-----|-----|-----|-----|-----|-----|-----|-----|-----|------|
| gcg | tac | gga | gcg | gca | gcc | cat | ctc | ccc | aag | gcc | gac | atg | act | gcc | tcg | 452  |
| Ala | Tyr | Gly | Ala | Ala | Ala | His | Leu | Pro | Lys | Ala | Asp | Met | Thr | Ala | Ser |      |
|     |     |     | 25  |     |     |     | 30  |     |     |     |     | 35  |     |     |     |      |

|     |     |     |     |     |     |     |     |     |     |     |     |     |     |     |     |
|-----|-----|-----|-----|-----|-----|-----|-----|-----|-----|-----|-----|-----|-----|-----|-----|
| ggg | agt | cct | gac | tac | ggg | cag | ccc | cac | aag | atc | aac | ccc | ctc | cca | cca | 500 |
| Gly | Ser | Pro | Asp | Tyr | Gly | Gln | Pro | His | Lys | Ile | Asn | Pro | Leu | Pro | Pro |     |
|     |     | 40  |     |     |     |     | 45  |     |     |     |     | 50  |     |     |     |     |

|     |     |     |     |     |     |     |     |     |     |     |     |     |     |     |     |
|-----|-----|-----|-----|-----|-----|-----|-----|-----|-----|-----|-----|-----|-----|-----|-----|
| cag | cag | gag | tgg | atc | aat | cag | cca | gtg | agg | gtc | aac | gtc | aag | cgg | gag | 548 |
| Gln | Gln | Glu | Trp | Ile | Asn | Gln | Pro | Val | Arg | Val | Asn | Val | Lys | Arg | Glu |     |
|     | 55  |     |     |     |     | 60  |     |     |     |     | 65  |     |     |     |     |     |

|     |     |     |     |     |     |     |     |     |     |     |     |     |     |     |     |
|-----|-----|-----|-----|-----|-----|-----|-----|-----|-----|-----|-----|-----|-----|-----|-----|
| tat | gac | cac | atg | aat | gga | tcc | agg | gag | tct | ccg | gtg | gac | tgc | agc | gtt | 596 |
| Tyr | Asp | His | Met | Asn | Gly | Ser | Arg | Glu | Ser | Pro | Val | Asp | Cys | Ser | Val |     |
| 70  |     |     |     |     | 75  |     |     |     |     | 80  |     |     |     |     | 85  |     |

|     |     |     |     |     |     |     |     |     |     |     |     |     |     |     |     |
|-----|-----|-----|-----|-----|-----|-----|-----|-----|-----|-----|-----|-----|-----|-----|-----|
| agc | aaa | tgc | agc | aag | ctg | gtg | ggc | gga | ggc | gag | tcc | aac | ccc | atg | aac | 644 |
| Ser | Lys | Cys | Ser | Lys | Leu | Val | Gly | Gly | Gly | Glu | Ser | Asn | Pro | Met | Asn |     |
|     |     |     |     | 90  |     |     |     |     | 95  |     |     |     |     | 100 |     |     |

|     |     |     |     |     |     |     |     |     |     |     |     |     |     |     |     |
|-----|-----|-----|-----|-----|-----|-----|-----|-----|-----|-----|-----|-----|-----|-----|-----|
| tac | aac | agc | tat | atg | gac | gag | aag | aat | ggc | ccc | cct | cct | ccc | aac | atg | 692 |
| Tyr | Asn | Ser | Tyr | Met | Asp | Glu | Lys | Asn | Gly | Pro | Pro | Pro | Pro | Asn | Met |     |
|     |     |     | 105 |     |     |     |     | 110 |     |     |     |     | 115 |     |     |     |

|     |     |     |     |     |     |     |     |     |     |     |     |     |     |     |     |
|-----|-----|-----|-----|-----|-----|-----|-----|-----|-----|-----|-----|-----|-----|-----|-----|
| acc | acc | aac | gag | agg | aga | gtc | atc | gtc | ccc | gca | gac | ccc | aca | ctg | tgg | 740 |
| Thr | Thr | Asn | Glu | Arg | Arg | Val | Ile | Val | Pro | Ala | Asp | Pro | Thr | Leu | Trp |     |
|     |     |     |     | 120 |     |     |     |     | 125 |     |     |     |     | 130 |     |     |

|     |     |     |     |     |     |     |     |     |     |     |     |     |     |     |     |
|-----|-----|-----|-----|-----|-----|-----|-----|-----|-----|-----|-----|-----|-----|-----|-----|
| aca | cag | gag | cat | gtg | agg | caa | tgg | ctg | gag | tgg | gcc | ata | aag | gag | tac | 788 |
| Thr | Gln | Glu | His | Val | Arg | Gln | Trp | Leu | Glu | Trp | Ala | Ile | Lys | Glu | Tyr |     |
|     | 135 |     |     |     |     | 140 |     |     |     |     | 145 |     |     |     |     |     |

|     |     |     |     |     |     |     |     |     |     |     |     |     |     |     |     |
|-----|-----|-----|-----|-----|-----|-----|-----|-----|-----|-----|-----|-----|-----|-----|-----|
| agc | ttg | atg | gag | atc | gac | aca | tcc | ttt | ttc | cag | aac | atg | gat | ggc | aag | 836 |
| Ser | Leu | Met | Glu | Ile | Asp | Thr | Ser | Phe | Phe | Gln | Asn | Met | Asp | Gly | Lys |     |
| 150 |     |     |     |     | 155 |     |     |     |     | 160 |     |     |     |     | 165 |     |

|     |     |     |     |     |     |     |     |     |     |     |     |     |     |     |     |
|-----|-----|-----|-----|-----|-----|-----|-----|-----|-----|-----|-----|-----|-----|-----|-----|
| gaa | ctg | tgt | aaa | atg | aac | aag | gag | gac | ttc | ctc | cgc | gcc | acc | acc | ctc | 884 |
| Glu | Leu | Cys | Lys | Met | Asn | Lys | Glu | Asp | Phe | Leu | Arg | Ala | Thr | Thr | Leu |     |
|     |     |     | 170 |     |     |     |     | 175 |     |     |     |     | 180 |     |     |     |

|     |     |     |     |     |     |     |     |     |     |     |     |     |     |     |     |
|-----|-----|-----|-----|-----|-----|-----|-----|-----|-----|-----|-----|-----|-----|-----|-----|
| tac | aac | acg | gaa | gtg | ctg | ttg | tca | cac | ctc | agt | tac | ctc | agg | gaa | agt | 932 |
| Tyr | Asn | Thr | Glu | Val | Leu | Leu | Ser | His | Leu | Ser | Tyr | Leu | Arg | Glu | Ser |     |
|     |     |     |     | 185 |     |     |     |     | 190 |     |     |     |     | 195 |     |     |

|     |     |     |     |     |     |     |     |     |     |     |     |     |     |     |     |
|-----|-----|-----|-----|-----|-----|-----|-----|-----|-----|-----|-----|-----|-----|-----|-----|
| tca | ctg | ctg | gcc | tat | aat | aca | acc | tcc | cac | acc | gac | caa | tcc | tca | cga | 980 |
| Ser | Leu | Leu | Ala | Tyr | Asn | Thr | Thr | Ser | His | Thr | Asp | Gln | Ser | Ser | Arg |     |
|     |     | 200 |     |     |     |     | 205 |     |     |     |     | 210 |     |     |     |     |

|     |     |     |     |     |     |     |     |     |     |     |     |     |     |     |     |      |
|-----|-----|-----|-----|-----|-----|-----|-----|-----|-----|-----|-----|-----|-----|-----|-----|------|
| ttg | agt | gtc | aaa | gaa | gac | cct | tct | tat | gac | tca | gtc | aga | aga | gga | gct | 1028 |
| Leu | Ser | Val | Lys | Glu | Asp | Pro | Ser | Tyr | Asp | Ser | Val | Arg | Arg | Gly | Ala |      |
|     | 215 |     |     |     |     | 220 |     |     |     |     | 225 |     |     |     |     |      |

|     |     |     |     |     |     |     |     |     |     |     |     |     |     |     |     |      |
|-----|-----|-----|-----|-----|-----|-----|-----|-----|-----|-----|-----|-----|-----|-----|-----|------|
| tgg | ggc | aat | aac | atg | aat | tct | ggc | ctc | aac | aaa | agt | cct | ccc | ctt | gga | 1076 |
| Trp | Gly | Asn | Asn | Met | Asn | Ser | Gly | Leu | Asn | Lys | Ser | Pro | Pro | Leu | Gly |      |
| 230 |     |     |     |     | 235 |     |     |     |     | 240 |     |     |     |     | 245 |      |

|     |     |     |     |     |     |     |     |     |     |     |     |     |     |     |     |      |
|-----|-----|-----|-----|-----|-----|-----|-----|-----|-----|-----|-----|-----|-----|-----|-----|------|
| ggg | gca | caa | acg | atc | agt | aag | aat | aca | gag | caa | cgg | ccc | cag | cca | gat | 1124 |
| Gly | Ala | Gln | Thr | Ile | Ser | Lys | Asn | Thr | Glu | Gln | Arg | Pro | Gln | Pro | Asp |      |
|     |     |     |     | 250 |     |     |     |     | 255 |     |     |     |     | 260 |     |      |

|     |     |     |     |     |     |     |     |     |     |     |     |     |     |     |     |      |
|-----|-----|-----|-----|-----|-----|-----|-----|-----|-----|-----|-----|-----|-----|-----|-----|------|
| ccg | tat | cag | atc | ctg | ggc | ccg | acc | agc | agt | cgc | cta | gcc | aac | cct | gga | 1172 |
| Pro | Tyr | Gln | Ile | Leu | Gly | Pro | Thr | Ser | Ser | Arg | Leu | Ala | Asn | Pro | Gly |      |
|     |     |     | 265 |     |     |     |     | 270 |     |     |     |     | 275 |     |     |      |

|     |     |     |     |     |     |     |     |     |     |     |     |     |     |     |     |      |
|-----|-----|-----|-----|-----|-----|-----|-----|-----|-----|-----|-----|-----|-----|-----|-----|------|
| agc | ggg | cag | atc | cag | ctg | tgg | caa | ttc | ctc | ctg | gag | ctg | ctc | tcc | gac | 1220 |
| Ser | Gly | Gln | Ile | Gln | Leu | Trp | Gln | Phe | Leu | Leu | Glu | Leu | Leu | Ser | Asp |      |
|     |     |     |     | 280 |     |     |     |     | 285 |     |     |     |     | 290 |     |      |

|     |     |     |     |     |     |     |     |     |     |     |     |     |     |     |     |      |
|-----|-----|-----|-----|-----|-----|-----|-----|-----|-----|-----|-----|-----|-----|-----|-----|------|
| agc | gcc | aac | gcc | agc | tgt | atc | acc | tgg | gag | ggg | acc | aac | ggg | gag | ttc | 1268 |
| Ser | Ala | Asn | Ala | Ser | Cys | Ile | Thr | Trp | Glu | Gly | Thr | Asn | Gly | Glu | Phe |      |
|     | 295 |     |     |     |     | 300 |     |     |     |     | 305 |     |     |     |     |      |

|     |     |     |     |     |     |     |     |     |     |     |     |     |     |     |     |      |
|-----|-----|-----|-----|-----|-----|-----|-----|-----|-----|-----|-----|-----|-----|-----|-----|------|
| aaa | atg | acg | gac | ccc | gat | gag | gtg | gcc | agg | cgc | tgg | ggc | gag | cgg | aaa | 1316 |
| Lys | Met | Thr | Asp | Pro | Asp | Glu | Val | Ala | Arg | Arg | Trp | Gly | Glu | Arg | Lys |      |
| 310 |     |     |     |     | 315 |     |     |     |     | 320 |     |     |     |     | 325 |      |

|     |     |     |     |     |     |     |     |     |     |     |     |     |     |     |     |      |
|-----|-----|-----|-----|-----|-----|-----|-----|-----|-----|-----|-----|-----|-----|-----|-----|------|
| agc | aag | ccc | aac | atg | aat | tac | gac | aag | ctg | agc | cgg | gcc | ctc | cgt | tat | 1364 |
| Ser | Lys | Pro | Asn | Met | Asn | Tyr | Asp | Lys | Leu | Ser | Arg | Ala | Leu | Arg | Tyr |      |
|     |     |     | 330 |     |     |     |     | 335 |     |     |     |     | 340 |     |     |      |

|  |  |
|---|---|
| tac tat gat aaa aac att atg acc aaa gtg cac ggc aaa aga tat gct<br>Tyr Tyr Asp Lys Asn Ile Met Thr Lys Val His Gly Lys Arg Tyr Ala<br>                  345                    350                  355 | 1412 |
| tac aaa ttt gac ttc cac ggc att gcc cag gct ctg cag cca cat ccg<br>Tyr Lys Phe Asp Phe His Gly Ile Ala Gln Ala Leu Gln Pro His Pro<br>           360                    365                    370 | 1460 |
| acc gag tcg tcc atg tac aag tac cct tct gac atc tcc tac atg cct<br>Thr Glu Ser Ser Met Tyr Lys Tyr Pro Ser Asp Ile Ser Tyr Met Pro<br>375                    380                    385 | 1508 |
| tcc tac cat gcc cac cag cag aag gtg aac ttt gtc cct ccc cat cca<br>Ser Tyr His Ala His Gln Gln Lys Val Asn Phe Val Pro Pro His Pro<br>390                    395                  400                  405 | 1556 |
| tcc tcc atg cct gtc act tcc tcc agc ttc ttt gga gcc gca tca caa<br>Ser Ser Met Pro Val Thr Ser Ser Ser Phe Phe Gly Ala Ala Ser Gln<br>                  410                    415                  420 | 1604 |
| tac tgg acc tcc ccc acg ggg gga atc tac ccc aac ccc aac gtc ccc<br>Tyr Trp Thr Ser Pro Thr Gly Gly Ile Tyr Pro Asn Pro Asn Val Pro<br>                    425                    430                  435 | 1652 |
| cgc cat cct aac acc cac gtg cct tca cac tta ggc agc tac tac tag<br>Arg His Pro Asn Thr His Val Pro Ser His Leu Gly Ser Tyr Tyr<br>                  440                    445                  450 | 1700 |
| aagcttactc atcagtggcc ttctagctga agcccatcct gcacacttac tggatgcttt | 1760 |
| ggactcaaca ggacatatgt ggccttgaag ggaagacaaa actggatgtt ctttcttgtt | 1820 |
| ggatagaacc tttgtatttg ttcttttaaaa acatttttttt taatgttggt aacttttgct | 1880 |
| tcctctacct gaacaaagag atgaataatt ccatgggcca gtatgccagt ttgaattctc | 1940 |
| agtctcctag catcttgtga gttgcatatt aagattactg gaatggttaa gtcatggttc | 2000 |
| tgagaaagaa gctgtacgtt ttctttatgt ttttatgacc aaagcagttt cttgtcaata | 2060 |
| cacggggttc agtatgacac agaatcatgg acttaacccg tcatgttctg gtttgagatt | 2120 |
| tagtgacaaa tagaggtggg aagcttataa tctaatttta ggaggaccaa attcagtgga | 2180 |
| tggcaactgg aacattgatt gtaaggccag tgaagttttc acccaactgg aatttgatgg | 2240 |
| aaagaaggtt tgtgtgttta agacgccaag ggcattgcag aatccctctc agtggacagt | 2300 |
| atgcactcag ctgaccactc tctctagaaa tagtcaagat atgaactaag aaattttaat | 2360 |
| gcaaatacat acattcctga agacgggga attaaattac taattttttt tttttttaa | 2420 |
| atgatgacag tggtcccaga acttggaaaa gttgtaggga tttctaaact caagcagatt | 2480 |
| cgcaagtgct gtgcgcttgt cagaccatca gaccagggcc aaccaatcag aaggcaactt | 2540 |
| actgtataaa ttatgcagag ttattttcct atatctcaca gtattaaaaa taaataatta | 2600 |
| aaaattaaga ataaataaac gagttgacct cggtcacaaa agcagtttta ctatcgaatc | 2660 |
| aatcgctgtt attttttta atgtaatttg tacatctttt tcaatctgt acatttgggc | 2720 |
| tgtctgtatg tttttatagc tggttttaa aaagcataat atgcctatag ctgaaaagga | 2780 |
| aacagggctg tttaagtcac tgacttatga gaaagcaaag cactggtaca gttatttaac | 2840 |
| aggcatacac aagcagggaa aagataatcc atttagatct ttaatgcttt ggaaatgcgt | 2900 |
| gtaacagtac tgcaataatc acagctctgg gaaaaacaac gaaactttcc cttgtggaga | 2960 |
| ggagggattt tcctgctcta tataagcaac atatttttag acattaaaat atatataatt | 3020 |
| ttgcaggtaa ttgttgactt ttttaactat attaagtgtt aagctgacaa ctgtcaaaga | 3080 |
| agaccatgtt gtaaaataat ttgactaaat aaatggttcc ttctctcagt gctgaggaca | 3140 |
| gttttcttat ttaccgcccc cgttaggtca aagggttttc cctggggaac ttccctattt | 3200 |
| acttcttgca ctatcaagaa ttttttcgaat gtacctactg cagtacagca gaaggtaaaa | 3260 |

```
aatcagtgtg gttttcatt gttgttgatg atgtttgtag tgttttgtg tgtgttattt      3320
aaatcttcct ccagcctaaa agggttttat aaaacagcag ctaaggccat ggataaacct      3380
gtatgtaagg actggagcaa agcgagctgg tctatccaga ctggtctgtg agatttaact      3440
ctgcagcctc ccctgggcac ttcagaccca gacggccacc ttctgccact ccagcaaaga      3500
ataagcgccc tgcttccttc aggtctcaga ccaggacttt atggctcatg cagatttta      3560
aggtcatttt tcttcccaag gaagaaactt gcctccagtt ccttcactgt taggtagctt      3620
attttcattt tctctatttt acaatgaaaa gagtgagacc tgggaagtcc ttgatttgca      3680
aggaattaga ctcacagcat tggtaaccct agaaccttct tagggtaaca ctaagtacct      3740
tctagacaac atgtctacct aaatgaaatg ggatgtgttt cggaacattt gtctccagtt      3800
ttttttaat cttgcaccct gccatttaaa aagatgtgta aagcacatat tctcaacata      3860
tgcacattga tttataaatc atatatacaa actgttacat tattcttcat attagaaaac      3920
aaatacaaaa tagaacattt taaatggtga tataaaaata aattgaaact gaaattctaa      3980
aaaaaaaaaa aaa                                                         3993

<210> SEQ ID NO 6
<211> LENGTH: 452
<212> TYPE: PRT
<213> ORGANISM: Homo sapiens

<400> SEQUENCE: 6

Met Asp Gly Thr Ile Lys Glu Ala Leu Ser Val Val Ser Asp Asp Gln
1               5                   10                  15

Ser Leu Phe Asp Ser Ala Tyr Gly Ala Ala His Leu Pro Lys Ala
                20                  25                  30

Asp Met Thr Ala Ser Gly Ser Pro Asp Tyr Gly Gln Pro His Lys Ile
            35                  40                  45

Asn Pro Leu Pro Pro Gln Gln Glu Trp Ile Asn Gln Pro Val Arg Val
        50                  55                  60

Asn Val Lys Arg Glu Tyr Asp His Met Asn Gly Ser Arg Glu Ser Pro
65                  70                  75                  80

Val Asp Cys Ser Val Ser Lys Cys Ser Lys Leu Val Gly Gly Gly Glu
                85                  90                  95

Ser Asn Pro Met Asn Tyr Asn Ser Tyr Met Asp Glu Lys Asn Gly Pro
                100                 105                 110

Pro Pro Pro Asn Met Thr Thr Asn Glu Arg Arg Val Ile Val Pro Ala
            115                 120                 125

Asp Pro Thr Leu Trp Thr Gln Glu His Val Arg Gln Trp Leu Glu Trp
        130                 135                 140

Ala Ile Lys Glu Tyr Ser Leu Met Glu Ile Asp Thr Ser Phe Phe Gln
145                 150                 155                 160

Asn Met Asp Gly Lys Glu Leu Cys Lys Met Asn Lys Glu Asp Phe Leu
                165                 170                 175

Arg Ala Thr Thr Leu Tyr Asn Thr Glu Val Leu Leu Ser His Leu Ser
                180                 185                 190

Tyr Leu Arg Glu Ser Ser Leu Leu Ala Tyr Asn Thr Thr Ser His Thr
            195                 200                 205

Asp Gln Ser Ser Arg Leu Ser Val Lys Glu Asp Pro Ser Tyr Asp Ser
        210                 215                 220

Val Arg Arg Gly Ala Trp Gly Asn Asn Met Asn Ser Gly Leu Asn Lys
225                 230                 235                 240
```

-continued

```
Ser Pro Pro Leu Gly Gly Ala Gln Thr Ile Ser Lys Asn Thr Glu Gln
                245                 250                 255

Arg Pro Gln Pro Asp Pro Tyr Gln Ile Leu Gly Pro Thr Ser Ser Arg
            260                 265                 270

Leu Ala Asn Pro Gly Ser Gly Gln Ile Gln Leu Trp Gln Phe Leu Leu
        275                 280                 285

Glu Leu Leu Ser Asp Ser Ala Asn Ala Ser Cys Ile Thr Trp Glu Gly
    290                 295                 300

Thr Asn Gly Glu Phe Lys Met Thr Asp Pro Asp Glu Val Ala Arg Arg
305                 310                 315                 320

Trp Gly Glu Arg Lys Ser Lys Pro Asn Met Asn Tyr Asp Lys Leu Ser
                325                 330                 335

Arg Ala Leu Arg Tyr Tyr Tyr Asp Lys Asn Ile Met Thr Lys Val His
            340                 345                 350

Gly Lys Arg Tyr Ala Tyr Lys Phe Asp Phe His Gly Ile Ala Gln Ala
        355                 360                 365

Leu Gln Pro His Pro Thr Glu Ser Ser Met Tyr Lys Tyr Pro Ser Asp
    370                 375                 380

Ile Ser Tyr Met Pro Ser Tyr His Ala His Gln Gln Lys Val Asn Phe
385                 390                 395                 400

Val Pro Pro His Pro Ser Ser Met Pro Val Thr Ser Ser Ser Phe Phe
                405                 410                 415

Gly Ala Ala Ser Gln Tyr Trp Thr Ser Pro Thr Gly Gly Ile Tyr Pro
            420                 425                 430

Asn Pro Asn Val Pro Arg His Pro Asn Thr His Val Pro Ser His Leu
        435                 440                 445

Gly Ser Tyr Tyr
    450

<210> SEQ ID NO 7
<211> LENGTH: 2802
<212> TYPE: DNA
<213> ORGANISM: Homo sapiens
<220> FEATURE:
<221> NAME/KEY: CDS
<222> LOCATION: (251)..(1519)

<400> SEQUENCE: 7
gagggtgcgc ccaccggtcc cgccgggcgc ccgcgggacg cgccgccagg gccctctccg      60 ccggggctc ggcgctcgcc cacctcttcc aaatttaacc attacctaaa tccgaaggga     120
aatgagcaaa cctctcggat tgggtgtcaa ggtctcctcc gggctgggc tgagcaagcc     180 ctcggagtga ccgtgggtga cagcggctcc agggactctt ggggcgcagt ggggaaagtg     240
ccggaccacc atg ccg cgc tca ttt ctc gtc aaa agc aag aag gct cac       289
            Met Pro Arg Ser Phe Leu Val Lys Ser Lys Lys Ala His
            1               5                   10 agc tac cac cag ccg cgc tcc cca gga cca gac tat tcc ctc cgt tta      337
Ser Tyr His Gln Pro Arg Ser Pro Gly Pro Asp Tyr Ser Leu Arg Leu
    15                  20                  25 gag aat gta ccg gcg cct agc cga gca gac agc act tca aat gca ggc      385
Glu Asn Val Pro Ala Pro Ser Arg Ala Asp Ser Thr Ser Asn Ala Gly
30                  35                  40                  45 ggg gcg aag gcg gag ccc cgg gac cgt ttg tcc ccc gaa tcg cag ctg      433
Gly Ala Lys Ala Glu Pro Arg Asp Arg Leu Ser Pro Glu Ser Gln Leu
            50                  55                  60
```

```
                                          -continued acc gaa gcc cca gac aga gcc tcc gca tcc cca gac agc tgc gaa ggc    481
Thr Glu Ala Pro Asp Arg Ala Ser Ala Ser Pro Asp Ser Cys Glu Gly
            65                  70                  75 agc gtc tgc gaa cgg agc tcg gag ttt gag gac ttc tgg agg ccc ccg    529
Ser Val Cys Glu Arg Ser Ser Glu Phe Glu Asp Phe Trp Arg Pro Pro
        80                  85                  90 tca ccc tcc gcg tct cca gcc tcg gag aag tca atg tgc cca tcg ctg    577
Ser Pro Ser Ala Ser Pro Ala Ser Glu Lys Ser Met Cys Pro Ser Leu
    95                 100                 105 gac gaa gcc cag ccc ttc ccc ctg cct ttc aaa ccg tac tca tgg agc    625
Asp Glu Ala Gln Pro Phe Pro Leu Pro Phe Lys Pro Tyr Ser Trp Ser
110                 115                 120                 125 ggc ctg gcg ggt tct gac ctg cgg cac ctg gtg cag agc tac cga ccg    673
Gly Leu Ala Gly Ser Asp Leu Arg His Leu Val Gln Ser Tyr Arg Pro
                130                 135                 140 tgt ggg gcc ctg gag cgt ggc gct ggc ctg ggc ctc ttc tgc gaa ccc    721
Cys Gly Ala Leu Glu Arg Gly Ala Gly Leu Gly Leu Phe Cys Glu Pro
            145                 150                 155 gcc ccg gag cct ggc cac ccg gcc gcg ctg tac ggc ccg aag cgg gct    769
Ala Pro Glu Pro Gly His Pro Ala Ala Leu Tyr Gly Pro Lys Arg Ala
        160                 165                 170 gcc ggc ggc gcg ggg gcc ggg gcg cca ggg agc tgc agc gca ggg gcc    817
Ala Gly Gly Ala Gly Ala Gly Ala Pro Gly Ser Cys Ser Ala Gly Ala
    175                 180                 185 ggt gcc acc gct ggc cct ggc cta ggg ctc tac ggc gac ttc ggg tct    865
Gly Ala Thr Ala Gly Pro Gly Leu Gly Leu Tyr Gly Asp Phe Gly Ser
190                 195                 200                 205 gcg gca gcc ggg ctg tat gag agg ccc acg gca gcg gcg ggc ttg ctg    913
Ala Ala Ala Gly Leu Tyr Glu Arg Pro Thr Ala Ala Ala Gly Leu Leu
                210                 215                 220 tac ccc gag cgt ggc cac ggg ctg cac gca gac aag ggc gct ggc gtc    961
Tyr Pro Glu Arg Gly His Gly Leu His Ala Asp Lys Gly Ala Gly Val
            225                 230                 235 aag gtg gag tcg gag ctg ctg tgc acc cgc ctg ctg ctg ggc ggc ggc   1009
Lys Val Glu Ser Glu Leu Leu Cys Thr Arg Leu Leu Leu Gly Gly Gly
        240                 245                 250 tcc tac aag tgc atc aag tgc agc aag gtg ttc tcc acg ccg cac ggg   1057
Ser Tyr Lys Cys Ile Lys Cys Ser Lys Val Phe Ser Thr Pro His Gly
    255                 260                 265 ctc gag gtg cac gtg cgc agg tcc cac agc ggt acc aga ccc ttt gcc   1105
Leu Glu Val His Val Arg Arg Ser His Ser Gly Thr Arg Pro Phe Ala
270                 275                 280                 285 tgc gag atg tgc ggc aag acc ttc ggg cac gcg gtg agc ctg gag cag   1153
Cys Glu Met Cys Gly Lys Thr Phe Gly His Ala Val Ser Leu Glu Gln
                290                 295                 300 cac aaa gcc gtg cac tcg cag gaa cgg agc ttt gac tgt aag atc tgt   1201
His Lys Ala Val His Ser Gln Glu Arg Ser Phe Asp Cys Lys Ile Cys
            305                 310                 315 ggg aag agc ttc aag agg tca tcc aca ctg tcc aca cac ctg ctt atc   1249
Gly Lys Ser Phe Lys Arg Ser Ser Thr Leu Ser Thr His Leu Leu Ile
        320                 325                 330 cac tca gac act cgg ccc tac ccc tgt cag tac tgt ggc aag agg ttc   1297
His Ser Asp Thr Arg Pro Tyr Pro Cys Gln Tyr Cys Gly Lys Arg Phe
    335                 340                 345 cac cag aag tca gac atg aag aaa cac act ttc atc cac act ggt gag   1345
His Gln Lys Ser Asp Met Lys Lys His Thr Phe Ile His Thr Gly Glu
350                 355                 360                 365 aag cct cac aag tgc cag gtg tgc ggc aag gca ttc agc cag agc tcc   1393
Lys Pro His Lys Cys Gln Val Cys Gly Lys Ala Phe Ser Gln Ser Ser
                370                 375                 380
```

| | | | | | | | | | | | | | | | | |
|---|---|---|---|---|---|---|---|---|---|---|---|---|---|---|---|---|
| aac | ctc | atc | acc | cac | agc | cgc | aaa | cac | aca | ggc | ttc | aag | ccc | ttc | ggc | 1441 |
| Asn | Leu | Ile | Thr | His | Ser | Arg | Lys | His | Thr | Gly | Phe | Lys | Pro | Phe | Gly | |
| | | | 385 | | | | 390 | | | | | 395 | | | | |
| tgc | gac | ctc | tgt | ggg | aag | ggt | ttc | cag | agg | aag | gtg | gac | ctc | cga | agg | 1489 |
| Cys | Asp | Leu | Cys | Gly | Lys | Gly | Phe | Gln | Arg | Lys | Val | Asp | Leu | Arg | Arg | |
| | | | 400 | | | | | 405 | | | | | 410 | | | |
| cac | cgg | gag | acg | cag | cat | ggg | ctc | aaa | tga | gcaccctggc | | tggctgcaag | | | | 1539 |
| His | Arg | Glu | Thr | Gln | His | Gly | Leu | Lys | | | | | | | | |
| | | 415 | | | | | 420 | | | | | | | | | |

| | | |
|---|---|---|
| cagcagctac acaacactac agagggcagc ctccctgctt gccaccactc tgctccctgc | 1599 |
| ttgcctccac tcccttctga cttttccagac cccaggtcca gtctgcagat cctaccaggt | 1659 |
| tgctcctcct tcgccttacc tcctggagct gccagaagaa atgaggtacc ttttcaaagt | 1719 |
| gcagccgaga gtgagaacca agtgactctc taggcttcgg acacaaatag gctcctctac | 1779 |
| acctgaagac aaaggcaaag tcaaatgggg accagaataa atcttagacc ccacagtcct | 1839 |
| tcccatttcc agccctaatc tacagacagg aatgcccttc aggtttcttc cctccccct | 1899 |
| cttgacctac cccagatatt tgtgtggaag aggaggaatc accatttaca aggtggacaa | 1959 |
| atgctaatat ttttatctag aaagaagagt gagtgttaac ttttattttt ttccttctgg | 2019 |
| ggggtctgtt gactcctttc ttttgggtgc tgcctataaa tcttggagga atcatttctc | 2079 |
| ctcctcaaaa actgattcag aaactgactt ggggaaggaa tttaatactt tgaagtcatg | 2139 |
| agatgcacca tcgaggctac ccccaagaag aagcagaaga gaagttggta atgagagggg | 2199 |
| attagaggtc ctcccttcag tagggctgtg aaaacctcat cactggaggt aaaagcacaa | 2259 |
| gcaatgcctg tggacaagat gtcattcatt cactcagcaa atgttcatgg atcaccggct | 2319 |
| accaaggtac caggcaccat gctaggtatt ggggaagaga gactgaagtc acaacccctg | 2379 |
| actgctcctc aaaagctaac ggttgcacct ccaagtggct gggtctgttc ttactcttgg | 2439 |
| agggaattct gagaagacag cacagaattg taaaccttcc cttttgaccc ttttggattt | 2499 |
| tatcaggtgt aaacaaaaag ctgaacagtt acttcaaaga tatgtgtgta tattcagttt | 2559 |
| tttattgtta agctgatatt ttaaagattt ctgagctagc aggcatgtgg gaaggaaggc | 2619 |
| tctgtcttca actctttgac cctccatgtg taccatagag gggggaaagg tggtatttc | 2679 |
| actttgatga ggttggtaaa tgttttttaga tcttctggta agcattatgt ttgttaatac | 2739 |
| atatttatta gagtgatgtt ttaagttaat aaagtattaa gagtattaaa aaaaaaaaa | 2799 |
| aaa | 2802 |

<210> SEQ ID NO 8
<211> LENGTH: 422
<212> TYPE: PRT
<213> ORGANISM: Homo sapiens

<400> SEQUENCE: 8

Met Pro Arg Ser Phe Leu Val Lys Ser Lys Lys Ala His Ser Tyr His
1               5                   10                  15

Gln Pro Arg Ser Pro Gly Pro Asp Tyr Ser Leu Arg Leu Glu Asn Val
            20                  25                  30

Pro Ala Pro Ser Arg Ala Asp Thr Ser Asn Ala Gly Gly Ala Lys
        35                  40                  45

Ala Glu Pro Arg Asp Arg Leu Ser Pro Glu Ser Gln Leu Thr Glu Ala
    50                  55                  60

Pro Asp Arg Ala Ser Ala Ser Pro Asp Ser Cys Glu Gly Ser Val Cys
65                  70                  75                  80

```
Glu Arg Ser Ser Glu Phe Glu Asp Phe Trp Arg Pro Ser Pro Ser
                85                  90                  95

Ala Ser Pro Ala Ser Glu Lys Ser Met Cys Pro Ser Leu Asp Glu Ala
            100                 105                 110

Gln Pro Phe Pro Leu Pro Phe Lys Pro Tyr Ser Trp Ser Gly Leu Ala
            115                 120                 125

Gly Ser Asp Leu Arg His Leu Val Gln Ser Tyr Arg Pro Cys Gly Ala
    130                 135                 140

Leu Glu Arg Gly Ala Gly Leu Gly Leu Phe Cys Glu Pro Ala Pro Glu
145                 150                 155                 160

Pro Gly His Pro Ala Ala Leu Tyr Gly Pro Lys Arg Ala Ala Gly Gly
                165                 170                 175

Ala Gly Ala Gly Ala Pro Gly Ser Cys Ser Ala Gly Ala Gly Ala Thr
            180                 185                 190

Ala Gly Pro Gly Leu Gly Leu Tyr Gly Asp Phe Gly Ser Ala Ala Ala
            195                 200                 205

Gly Leu Tyr Glu Arg Pro Thr Ala Ala Ala Gly Leu Leu Tyr Pro Glu
    210                 215                 220

Arg Gly His Gly Leu His Ala Asp Lys Gly Ala Gly Val Lys Val Glu
225                 230                 235                 240

Ser Glu Leu Leu Cys Thr Arg Leu Leu Leu Gly Gly Gly Ser Tyr Lys
                245                 250                 255

Cys Ile Lys Cys Ser Lys Val Phe Ser Thr Pro His Gly Leu Glu Val
            260                 265                 270

His Val Arg Arg Ser His Ser Gly Thr Arg Pro Phe Ala Cys Glu Met
    275                 280                 285

Cys Gly Lys Thr Phe Gly His Ala Val Ser Leu Glu Gln His Lys Ala
290                 295                 300

Val His Ser Gln Glu Arg Ser Phe Asp Cys Lys Ile Cys Gly Lys Ser
305                 310                 315                 320

Phe Lys Arg Ser Ser Thr Leu Ser Thr His Leu Leu Ile His Ser Asp
                325                 330                 335

Thr Arg Pro Tyr Pro Cys Gln Tyr Cys Gly Lys Arg Phe His Gln Lys
            340                 345                 350

Ser Asp Met Lys Lys His Thr Phe Ile His Thr Gly Glu Lys Pro His
    355                 360                 365

Lys Cys Gln Val Cys Gly Lys Ala Phe Ser Gln Ser Ser Asn Leu Ile
370                 375                 380

Thr His Ser Arg Lys His Thr Gly Phe Lys Pro Phe Gly Cys Asp Leu
385                 390                 395                 400

Cys Gly Lys Gly Phe Gln Arg Lys Val Asp Leu Arg Arg His Arg Glu
                405                 410                 415

Thr Gln His Gly Leu Lys
            420

<210> SEQ ID NO 9
<211> LENGTH: 5018
<212> TYPE: DNA
<213> ORGANISM: Homo sapiens
<220> FEATURE:
<221> NAME/KEY: CDS
<222> LOCATION: (578)..(1573)
```

<400> SEQUENCE: 9

```
gcccgggact atcccttcgc ggtgtagcgg cagccggaga cctggctgag gaggcaaccg    60
cgtagacacc tccctgctta gaaaacaaac actgaaccag accgatccca gttggagggt   120
tcgaaaatgt tccagacagc ctgtcgggag gggttgttgt tgctgttgga ctaaatagct   180
attcctgatt ggtcatgtat agggttttt aaggcgggtg gggggaggag ggggtagagg   240
aaaggctcca acacctgca ggttgggggc ggaaagctgt ttgcgattcc ctggactggt   300
tggtcgggga caggaggtaa ttcccagcca ttgaccccca tttctctctc tccctccctc   360
ttgccctgcc tctttctctc caccctatc tttcctggaa actcgctttg ggcgcggcag   420 atcgccagg accacaccgc agcgtaactg caggcctctc agcgaaaaag ggggaaagca   480
aagacccggg tgtgcatcct cttcctcggc ttccgcccct ttccggcgga gtggagatcc   540
tattcagagg ggccggtctc tctaaatatg ccccagg atg acc gag cgg ccg ccg   595
                                        Met Thr Glu Arg Pro Pro
                                         1               5 agc gag gcg gct cgc agt gac ccc cag cta gag gga cgg gac gcg gcc   643
Ser Glu Ala Ala Arg Ser Asp Pro Gln Leu Glu Gly Arg Asp Ala Ala
        10                  15                  20 gag gcc agc atg gcc ccc ccg cac ctg gtc ctg ctg aac ggc gtc gcc   691
Glu Ala Ser Met Ala Pro Pro His Leu Val Leu Leu Asn Gly Val Ala
    25                  30                  35 aag gag acg agc cgc gcg gcc gca gcg gag ccc cca gtc atc gaa ctg   739
Lys Glu Thr Ser Arg Ala Ala Ala Ala Glu Pro Pro Val Ile Glu Leu
40                  45                  50 ggc gcg cgc gga ggc ccg ggg ggc ggc cct gcc ggt ggg ggc ggc gcc   787
Gly Ala Arg Gly Gly Pro Gly Gly Gly Pro Ala Gly Gly Gly Gly Ala
55                  60                  65                  70 gcg aga gac tta aag ggc cgc gac gcg gcg acg gcc gaa gcg cgc cat   835
Ala Arg Asp Leu Lys Gly Arg Asp Ala Ala Thr Ala Glu Ala Arg His
                75                  80                  85 cgg gtg ccc acc acc gag ctg tgc aga cct ccc ggg ccc gcc ccg gcc   883
Arg Val Pro Thr Thr Glu Leu Cys Arg Pro Pro Gly Pro Ala Pro Ala
        90                  95                 100 ccc gcg ccc gcc tcg gtt aca gcg gag ctg ccc ggc gac ggc cgc atg   931
Pro Ala Pro Ala Ser Val Thr Ala Glu Leu Pro Gly Asp Gly Arg Met
    105                 110                 115 gtg cag ctg agt cct ccc gcg ctg gct gcc ccc gcc gcc ccc ggc cgc   979
Val Gln Leu Ser Pro Pro Ala Leu Ala Ala Pro Ala Ala Pro Gly Arg
120                 125                 130 gcg ctg ctc tac agc ctc agc cag ccg ctg gcc tct ctc ggc agc ggg  1027
Ala Leu Leu Tyr Ser Leu Ser Gln Pro Leu Ala Ser Leu Gly Ser Gly
135                 140                 145                 150 ttc ttt ggg gag ccg gat gcc ttc cct atg ttc acc acc aac aat cga  1075
Phe Phe Gly Glu Pro Asp Ala Phe Pro Met Phe Thr Thr Asn Asn Arg
                155                 160                 165 gtg aag agg aga cct tcc ccc tat gag atg gag att act gat ggt ccc  1123
Val Lys Arg Arg Pro Ser Pro Tyr Glu Met Glu Ile Thr Asp Gly Pro
        170                 175                 180 cac acc aaa gtt gtg cgg cgt atc ttc acc aac agc cgg gag cga tgg  1171
His Thr Lys Val Val Arg Arg Ile Phe Thr Asn Ser Arg Glu Arg Trp
    185                 190                 195 cgg cag cag aat gtg aac ggg gcc ttt gcc gag ctc cgc aag ctg atc  1219
Arg Gln Gln Asn Val Asn Gly Ala Phe Ala Glu Leu Arg Lys Leu Ile
200                 205                 210 ccc aca cat ccc ccg gac aag aag ctc agc aag aat gag atc ctc cgc  1267
Pro Thr His Pro Pro Asp Lys Lys Leu Ser Lys Asn Glu Ile Leu Arg
215                 220                 225                 230
```

```
ctg gcc atg aag tat atc aac ttc ttg gcc aag ctg ctc aat gac cag    1315
Leu Ala Met Lys Tyr Ile Asn Phe Leu Ala Lys Leu Leu Asn Asp Gln
            235                 240                 245 gag gag gag ggc acc cag cgg gcc aag act ggc aag gac cct gtg gtg    1363
Glu Glu Glu Gly Thr Gln Arg Ala Lys Thr Gly Lys Asp Pro Val Val
        250                 255                 260 ggg gct ggt ggg ggt gga ggt ggg gga ggg ggc ggc gcg ccc cca gat    1411
Gly Ala Gly Gly Gly Gly Gly Gly Gly Gly Gly Ala Pro Pro Asp
        265                 270                 275 gac ctc ctg caa gac gtg ctt tcc ccc aac tcc agc tgc ggc agc tcc    1459
Asp Leu Leu Gln Asp Val Leu Ser Pro Asn Ser Ser Cys Gly Ser Ser
    280                 285                 290 ctg gat ggg gca gcc agc ccg gac agc tac acg gag gag ccc gcg ccc    1507
Leu Asp Gly Ala Ala Ser Pro Asp Ser Tyr Thr Glu Glu Pro Ala Pro
295                 300                 305                 310 aaa cac acg gcc cgc agc ctc cat cct gcc atg ctg cct gcc gcc gat    1555
Lys His Thr Ala Arg Ser Leu His Pro Ala Met Leu Pro Ala Ala Asp
                315                 320                 325 gga gcc ggc cct cgg tga tgggtctggg ccaccaggat cagccaggag           1603
Gly Ala Gly Pro Arg
        330 ggcgttctta ggctgctggg atggtgggct tcagggcagg tggggtgaga attgggcggc  1663 tctgaagcaa ggcggtggac ttgaactttc ctggatgtct gaactttggg aagcctttac  1723 tgaccctggg gctggctttt ctgtttcctg taccagtagg agatcagaaa aatggagcaa  1783 agtggtaggt acttttttgtg aagacggcac ggtcttccct cttccctcag tcccaaatcc 1843 ttcccaagta agaggctgga gttgtcactg cttttggcct ggagtttggg atccctgtct  1903 ttcctaagac ctggggttgt cagctctcat ctgaggcatc cagcagtctc tgccttgcct  1963 ttagcccctc ccaagctggc tggggtggcc tgtgtggcca cttctgtcca tatttatagg  2023 tacccaatag ctgcccattt cgtgagcccc atcttcaccc aggcctatgt tgatccatcc  2083 agcttgccag atgctgcaga gtcacaagcc tcgaggtgcc ttcttcaggg cctggttgaa  2143 gaagatgatc agtggacagt ctgctctaga tgagctgggc cggagggtca ggaaacccag  2203 tcgcccttac ttcttgccct ggggatcaaa gttctgcttt ctccccaatg agacttgcct  2263 tcctaagcct gtggctgtgg agacaatgtc tgcagccctg agaaagccct gtcgggcttt  2323 gtgtgaaggc agagaaaggg acaatgatag tagagtgata tggagcaaga gatattttgg  2383 gcatgtgggc ttcaactcct cgacatcact gttcatgctg gcgagtgaat gccagtgtgc  2443 tgatgggcgt acgctggtgc tgagtagatg cgcagcccca tctgtgcatt ctcctggatg  2503 cttagaggga tttctttgct gtaagatgtc tgtttgctga tggtctggtc tatgttccga  2563 attgagcaca aaacctgtcc tatgaatgct ttgcatttgg aattttttgct tgacttcagt  2623 tattggtgga atctttagcg ctcaatagga ccaggatcca gcctcacttc tagggtatgg  2683 gaaatccaat cagagaccag gccctggcta agacccaaac atatgcacat tcacttagca  2743 gaaccttaaa caccccctcag ttgtgcagct tttggtcatc aagggtgcgt ctgggaggtt  2803 ggtttaatgc aatagaagtg ctcccctctg aaagttgtac atgaaatttt tgtaaatcac  2863 atccttatcc ttcatctttt aaagaaataa ccactgcaag tccttttgta aagtgaagaa  2923 tccttttgta gaatgaacca ctgccccttc attgatttcc tgtgtcaatc cagatggtgg  2983 gatgtggttt tcttaaggtg aggcctgtct gtgacctgca tctaagccca tgggacaaat  3043 tgcacagaag tcctgtatgt ctgtcattgt acccttaagt caccctagcc ctctccctct  3103
```

```
aggctctgcc ttcgaggtca gaggagagat agcctgtggc cctgtcctgc catgcaagaa   3163
ctcatcactg tggctgtctg gaaagccccc ccttatagtt tgggcttcag cctagtggct   3223
tgtcctcacc atgatggggc cctaattcag ccatgtacag acagagaata tgtctgctcc   3283
tttccccttc cttttaagta aggtccaatt ctcgagcttg gggcaacatt gttcaccttt   3343
gtagcactca ggctctccat tcaatttcag gctccccaga tcatgttttg gtgaaaatta   3403
gggttggttc ctttccaacg tttggaagat cctgtgagga gccccatctg tctaaagata   3463
gagtcattgc tgtaggatct aaggctgttt gcttcaccgt ggattcgctt gagttaggaa   3523
tgagaagtag ccacagtatg gatgggtgga tgggttttat gagatggatc acatatttta   3583
ttaagaactc aaacttctgg ctccctcttc tttcagactt gccatgtgac tctggcttgg   3643
cctatctcct agggctatgg tgtggactga atgggatcat gaaagtagac agttttgaga   3703
acgtaaagaa cttttctctt tccctcaatc tcaatcctgc agtggggttt cgcagcctga   3763
gtccacgacc taggcagtag gccggtgtgc ctgactgccc agcatttggg taatttagat   3823
tgtaaaccgc tttggcctga gttattgaga ttgtcctcat ttctccagat tatctatttg   3883
tgtgtgtgtg tgtgtgtgtg tgagagacgg tgtcttgttc tgtcactcag gctggagtac   3943
agtggtgcca tcattgctgt ctgcagcctt gaactctggg ctcaagcaat cctctcacct   4003
cagcctcccg agtagggagg accacaggtg tgagccacca cacctggcta attttttactt   4063 tttttttttt ttggtagaga tggagtcttg ctatattgcc caggctggtc ttgaagtcct   4123
ggcttcaggc aattctcctg cctttgcctc cagaagcact gggatcacag gtgtcagcca   4183
ttgcacccag cccagattgt cttaatttct atcttgttcc aaggccaggg acagtaataa   4243
gaatggaaaa gagatatggg aacactggca gactgtgtaa aatgtaatgc aactacccaa   4303
aacaagcctg gtaggaaagg gcaagtcttt aggtctttgt aagaactaaa gaagatctgt   4363
aatttttatt ttcaccctct gtaccccatg accttatcct tcctctcctt ccttgttacc   4423
catgaaaaac tggcaacatt ccaagaatag catctgtaca aaggggaaag aacataaagg   4483
taaaacaaaa caaaacaaca ttttgagaac aaagatgacc ataaccactg aagggaatca   4543
catcttttaa gacaaattca tattctttta tttgttatgg cagatgacaa gatggtacaa   4603
cctttattct tttccaaaat aaaacaaagg gcacagcatc tgtagtcagc cgacaactat   4663
ttcggccttt tggggtggg tctggccgta cttgtgattt cgatggtacg tgaccctctg   4723
ctgaagactt gcccctgcc cgtgtacata gtgcattgtt tctgtgggcg ggcccagcac   4783
tttccgtcaa cgttgtactg tatgtgatga attgcgttgg tctctgcatt tttctgcaga   4843
agaggagtaa ccgctccagg taccttgacc tttgtacagc ccagaggcca acactgtggg   4903
tgtgtgactc tttagcaaaa aaacccatg tggtgatgat gtgtatatat atgtgaggat   4963
gtatcgggaa gatttctaaa taaagttttt acaaaggggga aaaaaaaaaa aaaaa         5018
```

<210> SEQ ID NO 10
<211> LENGTH: 331
<212> TYPE: PRT
<213> ORGANISM: Homo sapiens

<400> SEQUENCE: 10

Met Thr Glu Arg Pro Pro Ser Glu Ala Ala Arg Ser Asp Pro Gln Leu
1               5                   10                  15

Glu Gly Arg Asp Ala Ala Glu Ala Ser Met Ala Pro Pro His Leu Val
            20                  25                  30

Leu Leu Asn Gly Val Ala Lys Glu Thr Ser Arg Ala Ala Ala Ala Glu

|  |  |  | 35 |  |  |  | 40 |  |  |  | 45 |  |  |
|---|---|---|---|---|---|---|---|---|---|---|---|---|---|

Pro Pro Val Ile Glu Leu Gly Ala Arg Gly Gly Pro Gly Gly Gly Pro
 50                     55                      60

Ala Gly Gly Gly Ala Ala Arg Asp Leu Lys Gly Arg Asp Ala Ala
65                   70                  75                  80

Thr Ala Glu Ala Arg His Arg Val Pro Thr Glu Leu Cys Arg Pro
             85                      90                      95

Pro Gly Pro Ala Pro Ala Pro Ala Ser Val Thr Ala Glu Leu
            100                 105                 110

Pro Gly Asp Gly Arg Met Val Gln Leu Ser Pro Ala Leu Ala Ala
            115                 120                 125

Pro Ala Ala Pro Gly Arg Ala Leu Leu Tyr Ser Leu Ser Gln Pro Leu
    130                 135                 140

Ala Ser Leu Gly Ser Gly Phe Phe Gly Glu Pro Asp Ala Phe Pro Met
145                 150                 155                 160

Phe Thr Thr Asn Asn Arg Val Lys Arg Arg Pro Ser Pro Tyr Glu Met
                165                 170                 175

Glu Ile Thr Asp Gly Pro His Thr Lys Val Val Arg Arg Ile Phe Thr
            180                 185                 190

Asn Ser Arg Glu Arg Trp Arg Gln Gln Asn Val Asn Gly Ala Phe Ala
        195                 200                 205

Glu Leu Arg Lys Leu Ile Pro Thr His Pro Pro Asp Lys Lys Leu Ser
    210                 215                 220

Lys Asn Glu Ile Leu Arg Leu Ala Met Lys Tyr Ile Asn Phe Leu Ala
225                 230                 235                 240

Lys Leu Leu Asn Asp Gln Glu Glu Gly Thr Gln Arg Ala Lys Thr
                245                 250                 255

Gly Lys Asp Pro Val Val Gly Ala Gly Gly Gly Gly Gly Gly Gly
            260                 265                 270

Gly Gly Ala Pro Pro Asp Asp Leu Leu Gln Asp Val Leu Ser Pro Asn
        275                 280                 285

Ser Ser Cys Gly Ser Ser Leu Asp Gly Ala Ala Ser Pro Asp Ser Tyr
    290                 295                 300

Thr Glu Glu Pro Ala Pro Lys His Thr Ala Arg Ser Leu His Pro Ala
305                 310                 315                 320

Met Leu Pro Ala Ala Asp Gly Ala Gly Pro Arg
                325                 330

<210> SEQ ID NO 11
<211> LENGTH: 1788
<212> TYPE: DNA
<213> ORGANISM: Homo sapiens
<220> FEATURE:
<221> NAME/KEY: CDS
<222> LOCATION: (655)..(1497)

<400> SEQUENCE: 11
ggagtgtgca aagccaaagg gcagactcgg acataagagg aggcagcttc cctgcctcag      60
tttaccccct gcgtgcatcc aggcacctcc ctccccggct gccctggggc ccgggtcccc     120
agaggcccgg ggtccctaca gtggctgggg gagcggaagg cgaagccctg aggggtggcg     180
gaccgagtcc tgccagcgcc ggctgggggc ggggccggga ggcccgcgct gctaggtccc     240
cgcccgctgg tttcctccgg ggtcagccag gctccttatc aggcgcggcc aggcagcctg     300
gcccttatct gcactgggcc agcatcctcc ggccgctgcg ccgccagggg tgagagggag     360

-continued

| | |
|---|---|
| gaaaccgggc cgccggggc ggggagaagg cgggccggcc cgggagccgc tcactttccc | 420 |
| tgggggggac ctacgcggag acctcggcta tcctggcctt ccgaggccca cgaggaggcg | 480 |
| cggcccaacg ccggggcctg gagcattgag gccggaccct cgcgagacag cagagcctgg | 540 |
| cctgacgctg gaaaccacac cctggcccag actgccagcc ctgacgggac agagccaggg | 600 |
| cactcaccag gctgcaagaa cagtgctggg gtgagtaccc ccacgtcggg gtcc atg<br>                                                                                               Met<br>                                                                                               1 | 657 |
| tgc ccg cct cag gca cag gca gag gtg ggc ccc acc atg act gag aag<br>Cys Pro Pro Gln Ala Gln Ala Glu Val Gly Pro Thr Met Thr Glu Lys<br>                5                      10                      15 | 705 |
| gca gag atg gtg tgt gcc ccc agc cca gcg cct gcc cca ccc cct aag<br>Ala Glu Met Val Cys Ala Pro Ser Pro Ala Pro Ala Pro Pro Pro Lys<br>        20                      25                      30 | 753 |
| cct gcc tcg cct ggg ccc ccg cag gtg gag gag gtg ggc cac cga gga<br>Pro Ala Ser Pro Gly Pro Pro Gln Val Glu Glu Val Gly His Arg Gly<br>     35                      40                      45 | 801 |
| ggc tcc tcg ccc ccc agg ctg cca cct ggt gta cca gtg atc agc ctg<br>Gly Ser Ser Pro Pro Arg Leu Pro Pro Gly Val Pro Val Ile Ser Leu<br>50                      55                      60                      65 | 849 |
| ggc cac agc agg ccc cca ggg gta gcc atg ccc acc aca gag ctg ggc<br>Gly His Ser Arg Pro Pro Gly Val Ala Met Pro Thr Thr Glu Leu Gly<br>              70                      75                      80 | 897 |
| act ctg cgg ccc ccg ctg ctg caa ctc tcc acc ctg gga act gcc ccg<br>Thr Leu Arg Pro Pro Leu Leu Gln Leu Ser Thr Leu Gly Thr Ala Pro<br>            85                      90                      95 | 945 |
| ccc act ttg gcc ctg cac tac cac cct cac ccc ttc ctc aac agt gtc<br>Pro Thr Leu Ala Leu His Tyr His Pro His Pro Phe Leu Asn Ser Val<br>        100                      105                      110 | 993 |
| tac att ggg cca gca gga cct ttt agc atc ttc cct agc agc cgg ttg<br>Tyr Ile Gly Pro Ala Gly Pro Phe Ser Ile Phe Pro Ser Ser Arg Leu<br>    115                      120                      125 | 1041 |
| aag cgg aga cca agc cac tgt gag ctg gac ctg gct gag ggg cac cag<br>Lys Arg Arg Pro Ser His Cys Glu Leu Asp Leu Ala Glu Gly His Gln<br>130                      135                      140                      145 | 1089 |
| ccc cag aag gtg gcc cgg cgc gtg ttc acc aac agc cgg gag cgc tgg<br>Pro Gln Lys Val Ala Arg Arg Val Phe Thr Asn Ser Arg Glu Arg Trp<br>                150                      155                      160 | 1137 |
| cgg cag cag aac gtt aac ggc gcc ttc gcc gag ctg agg aag ctg ctg<br>Arg Gln Gln Asn Val Asn Gly Ala Phe Ala Glu Leu Arg Lys Leu Leu<br>            165                      170                      175 | 1185 |
| ccg acg cac ccg ccc gac cgg aag ctg agc aag aac gag gtg ctc cgc<br>Pro Thr His Pro Pro Asp Arg Lys Leu Ser Lys Asn Glu Val Leu Arg<br>        180                      185                      190 | 1233 |
| cta gcc atg aag tac atc ggc ttc ctg gtg cgg ctg ctg cgc gac caa<br>Leu Ala Met Lys Tyr Ile Gly Phe Leu Val Arg Leu Leu Arg Asp Gln<br>    195                      200                      205 | 1281 |
| gcc gca gct ctg gcc gca ggc ccc acc cct ccc ggg cct cgc aaa cgg<br>Ala Ala Ala Leu Ala Ala Gly Pro Thr Pro Pro Gly Pro Arg Lys Arg<br>210                      215                      220                      225 | 1329 |
| ccg gtg cac cgg gtc cca gac gac ggc gcc cgc cgg gga tcc gga cgc<br>Pro Val His Arg Val Pro Asp Asp Gly Ala Arg Arg Gly Ser Gly Arg<br>                230                      235                      240 | 1377 |
| agg gcc gag gcg gca gcg cgc tcg cag ccc gcg ccc ccg gcc gac ccc<br>Arg Ala Glu Ala Ala Ala Arg Ser Gln Pro Ala Pro Pro Ala Asp Pro<br>            245                      250                      255 | 1425 |
| gac ggc agc ccc ggt gga gcg gcc cgg ccc atc aag atg gag caa acc<br>Asp Gly Ser Pro Gly Gly Ala Ala Arg Pro Ile Lys Met Glu Gln Thr<br>        260                      265                      270 | 1473 |

```
gct ttg agc cca gag gtg cgg tga ccgcacgcgg cagcacctct gagccggagg    1527
Ala Leu Ser Pro Glu Val Arg
    275                 280 gcaccaggga ctcggcccag ggccgtcaag gaaagggcag tggacgtgct gcgcatgttc    1587
gggagcgaac tcccccgaag aaggaccagt gaagacgtca ggggcaaggt ctcggggggtc    1647 cggaagggtg atcatcgacc cccaagggac ccgcagaccc ttaaaaaaat cacccacaac    1707
cctctggaag tggccttgcc cggtcccctt cccaggggcg aggtcggcaa agcaacatgg    1767
cagagcagtc ataggaccca a                                              1788

<210> SEQ ID NO 12
<211> LENGTH: 280
<212> TYPE: PRT
<213> ORGANISM: Homo sapiens

<400> SEQUENCE: 12

Met Cys Pro Pro Gln Ala Gln Ala Glu Val Gly Pro Thr Met Thr Glu
1               5                   10                  15

Lys Ala Glu Met Val Cys Ala Pro Ser Pro Ala Pro Ala Pro Pro Pro
            20                  25                  30

Lys Pro Ala Ser Pro Gly Pro Pro Gln Val Glu Val Gly His Arg
        35                  40                  45

Gly Gly Ser Ser Pro Pro Arg Leu Pro Pro Gly Val Pro Val Ile Ser
    50                  55                  60

Leu Gly His Ser Arg Pro Pro Gly Val Ala Met Pro Thr Thr Glu Leu
65                  70                  75                  80

Gly Thr Leu Arg Pro Pro Leu Leu Gln Leu Ser Thr Leu Gly Thr Ala
                85                  90                  95

Pro Pro Thr Leu Ala Leu His Tyr His Pro His Pro Phe Leu Asn Ser
            100                 105                 110

Val Tyr Ile Gly Pro Ala Gly Pro Phe Ser Ile Phe Pro Ser Ser Arg
        115                 120                 125

Leu Lys Arg Arg Pro Ser His Cys Glu Leu Asp Leu Ala Glu Gly His
    130                 135                 140

Gln Pro Gln Lys Val Ala Arg Arg Val Phe Thr Asn Ser Arg Glu Arg
145                 150                 155                 160

Trp Arg Gln Gln Asn Val Asn Gly Ala Phe Ala Glu Leu Arg Lys Leu
                165                 170                 175

Leu Pro Thr His Pro Pro Asp Arg Lys Leu Ser Lys Asn Glu Val Leu
            180                 185                 190

Arg Leu Ala Met Lys Tyr Ile Gly Phe Leu Val Arg Leu Leu Arg Asp
        195                 200                 205

Gln Ala Ala Leu Ala Ala Gly Pro Thr Pro Gly Pro Arg Lys
    210                 215                 220

Arg Pro Val His Arg Val Pro Asp Asp Gly Ala Arg Gly Ser Gly
225                 230                 235                 240

Arg Arg Ala Glu Ala Ala Arg Ser Gln Pro Ala Pro Ala Asp
                245                 250                 255

Pro Asp Gly Ser Pro Gly Gly Ala Ala Arg Pro Ile Lys Met Glu Gln
            260                 265                 270

Thr Ala Leu Ser Pro Glu Val Arg
        275                 280

<210> SEQ ID NO 13
```

<211> LENGTH: 3383
<212> TYPE: DNA
<213> ORGANISM: Homo sapiens
<220> FEATURE:
<221> NAME/KEY: CDS
<222> LOCATION: (335)..(1777)

<400> SEQUENCE: 13

| | |
|---|---:|
| gtgagcgcca ggaaggtagc gaggccagcg tcgccccggg actcgctgct caagtctgtc | 60 |
| tattgcctgc cgccacatcc atcctagcag ggccccgtcg cccaccaggc ggacaaaagc | 120 |
| ggtccgctga acaccatgcg gccgctcggc gtgccgccca ggctctgctg gtgagcgccg | 180 |
| ccaccccgcg cccaggtccc gcgagcccgc ctgccgcgca cctcgccctg ctcccagctc | 240 |
| tactccaggc cccgtccgcc cgggggcgcc gcccaccgcg cctcgctcgg gccgttgccg | 300 |
| tctgcaccca gaccctgagc cgccgccgcc ggcc atg gag gtg gcg ccc gag cag | 355 |
|                                                Met Glu Val Ala Pro Glu Gln<br>                                                1            5 | |
| ccg cgc tgg atg gcg cac ccg gcc gtg ctg aat gcg cag cac ccc gac<br>Pro Arg Trp Met Ala His Pro Ala Val Leu Asn Ala Gln His Pro Asp<br>        10                      15                      20 | 403 |
| tca cac cac ccg ggc ctg gcg cac aac tac atg gaa ccc gcg cag ctg<br>Ser His His Pro Gly Leu Ala His Asn Tyr Met Glu Pro Ala Gln Leu<br>25                      30                      35 | 451 |
| ctg cct cca gac gag gtg gac gtc ttc ttc aat cac ctc gac tcg cag<br>Leu Pro Pro Asp Glu Val Asp Val Phe Phe Asn His Leu Asp Ser Gln<br>40                      45                      50                      55 | 499 |
| ggc aac ccc tac tat gcc aac ccc gct cac gcg cgg gcg cgc gtc tcc<br>Gly Asn Pro Tyr Tyr Ala Asn Pro Ala His Ala Arg Ala Arg Val Ser<br>                      60                      65                      70 | 547 |
| tac agc ccc gcg cac gcc cgc ctg acc gga ggc cag atg tgc cgc cca<br>Tyr Ser Pro Ala His Ala Arg Leu Thr Gly Gly Gln Met Cys Arg Pro<br>        75                      80                      85 | 595 |
| cac ttg ttg cac agc ccg ggt ttg ccc tgg ctg gac ggg ggc aaa gca<br>His Leu Leu His Ser Pro Gly Leu Pro Trp Leu Asp Gly Gly Lys Ala<br>90                      95                      100 | 643 |
| gcc ctc tct gcc gct gcg gcc cac cac cac aac ccc tgg acc gtg agc<br>Ala Leu Ser Ala Ala Ala Ala His His His Asn Pro Trp Thr Val Ser<br>105                      110                      115 | 691 |
| ccc ttc tcc aag acg cca ctg cac ccc tca gct gct gga ggc cct gga<br>Pro Phe Ser Lys Thr Pro Leu His Pro Ser Ala Ala Gly Gly Pro Gly<br>120                      125                      130                      135 | 739 |
| ggc cca ctc tct gtg tac cca ggg gct ggg ggt ggg agc ggg gga ggc<br>Gly Pro Leu Ser Val Tyr Pro Gly Ala Gly Gly Gly Ser Gly Gly Gly<br>                      140                      145                      150 | 787 |
| agc ggg agc tca gtg gcc tcc ctc acc cct aca gca gcc cac tct ggc<br>Ser Gly Ser Ser Val Ala Ser Leu Thr Pro Thr Ala Ala His Ser Gly<br>                      155                      160                      165 | 835 |
| tcc cac ctt ttc ggc ttc cca ccc acg cca ccc aaa gaa gtg tct cct<br>Ser His Leu Phe Gly Phe Pro Pro Thr Pro Pro Lys Glu Val Ser Pro<br>                      170                      175                      180 | 883 |
| gac cct agc acc acg ggg gct gcg tct cca gcc tca tct tcc gcg ggg<br>Asp Pro Ser Thr Thr Gly Ala Ala Ser Pro Ala Ser Ser Ser Ala Gly<br>185                      190                      195 | 931 |
| ggt agt gca gcc cga gga gag gac aag gac ggc gtc aag tac cag gtg<br>Gly Ser Ala Ala Arg Gly Glu Asp Lys Asp Gly Val Lys Tyr Gln Val<br>200                      205                      210                      215 | 979 |
| tca ctg acg gag agc atg aag atg gaa agt ggc agt ccc ctg cgc cca<br>Ser Leu Thr Glu Ser Met Lys Met Glu Ser Gly Ser Pro Leu Arg Pro<br>                      220                      225                      230 | 1027 |

```
ggc cta gct act atg ggc acc cag cct gct aca cac cac ccc atc ccc    1075
Gly Leu Ala Thr Met Gly Thr Gln Pro Ala Thr His His Pro Ile Pro
            235             240             245 acc tac ccc tcc tat gtg ccg gcg gct gcc cac gac tac agc agc gga    1123
Thr Tyr Pro Ser Tyr Val Pro Ala Ala Ala His Asp Tyr Ser Ser Gly
        250             255             260 ctc ttc cac ccc gga ggc ttc ctg ggg gga ccg gcc tcc agc ttc acc    1171
Leu Phe His Pro Gly Gly Phe Leu Gly Gly Pro Ala Ser Ser Phe Thr
    265             270             275 cct aag cag cgc agc aag gct cgt tcc tgt tca gaa ggc cgg gag tgt    1219
Pro Lys Gln Arg Ser Lys Ala Arg Ser Cys Ser Glu Gly Arg Glu Cys
280             285             290             295 gtc aac tgt ggg gcc aca gcc acc cct ctc tgg cgg cgg gac ggc acc    1267
Val Asn Cys Gly Ala Thr Ala Thr Pro Leu Trp Arg Arg Asp Gly Thr
            300             305             310 ggc cac tac ctg tgc aat gcc tgt ggc ctc tac cac aag atg aat ggg    1315
Gly His Tyr Leu Cys Asn Ala Cys Gly Leu Tyr His Lys Met Asn Gly
        315             320             325 cag aac cga cca ctc atc aag ccc aag cga aga ctg tcg gcc gcc aga    1363
Gln Asn Arg Pro Leu Ile Lys Pro Lys Arg Arg Leu Ser Ala Ala Arg
    330             335             340 aga gcc ggc acc tgt tgt gca aat tgt cag acg aca acc acc tta       1411
Arg Ala Gly Thr Cys Cys Ala Asn Cys Gln Thr Thr Thr Thr Leu
345             350             355 tgg cgc cga aac gcc aac ggg gac cct gtc tgc aac gcc tgt ggc ctc    1459
Trp Arg Arg Asn Ala Asn Gly Asp Pro Val Cys Asn Ala Cys Gly Leu
360             365             370             375 tac tac aag ctg cac aat gtt aac agg cca ctg acc atg aag aag gaa    1507
Tyr Tyr Lys Leu His Asn Val Asn Arg Pro Leu Thr Met Lys Lys Glu
            380             385             390 ggg atc cag act cgg aac cgg aag atg tcc aac aag tcc aag aag agc    1555
Gly Ile Gln Thr Arg Asn Arg Lys Met Ser Asn Lys Ser Lys Lys Ser
        395             400             405 aag aaa ggg gcg gag tgc ttc gag gag ctg tca aag tgc atg cag gag    1603
Lys Lys Gly Ala Glu Cys Phe Glu Glu Leu Ser Lys Cys Met Gln Glu
    410             415             420 aag tca tcc ccc ttc agt gca gct gcc ctg gct gga cac atg gca cct    1651
Lys Ser Ser Pro Phe Ser Ala Ala Ala Leu Ala Gly His Met Ala Pro
425             430             435 gtg ggc cac ctc ccg ccc ttc agc cac tcc gga cac atc ctg ccc act    1699
Val Gly His Leu Pro Pro Phe Ser His Ser Gly His Ile Leu Pro Thr
440             445             450             455 ccg acg ccc atc cac ccc tcc tcc agc ctc tcc ttc ggc cac ccc cac    1747
Pro Thr Pro Ile His Pro Ser Ser Ser Leu Ser Phe Gly His Pro His
            460             465             470 ccg tcc agc atg gtg acc gcc atg ggc tag ggaacagatg gacgtcgagg      1797
Pro Ser Ser Met Val Thr Ala Met Gly
        475             480 accgggcact cccgggatgg gtggaccaaa cccttagcag cccagcattt cccgaaggcc    1857
gacaccactc ctgccagccc ggctcggccc agcacccct ctcctggagg cgcccagca     1917 gcctgccagc agttactgtg aatgttcccc accgctgaga ggctgcctcc gcacctgacc    1977
gctgcccagg tggggtttcc tgcatggaca gttgtttgga gaacaacaag gacaacttta    2037
tgtagagaaa aggaggggac gggacagacg aaggcaacca tttttagaag gaaaaaggat    2097
taggcaaaaa taatttattt tgctcttgtt tctaacaagg acttggagac ttggtggtct    2157
gagctgtccc aagtcctccg gttcttcctc gggattggcg ggtccacttg ccagggctct    2217
gggggcagat ttgtggggac ctcagcctgc accctcttct cctctggctt ccctctctga    2277
```

```
aatagccgaa ctccaggctg ggctgagcca aagccagagt ggccacggcc cagggagggt    2337
gagctggtgc ctgctttgac gggccaggcc ctggagggca gagacaatca cgggcggtcc    2397
tgcacagatt cccaggccag ggctgggtca caggaaggaa acaacatttt cttgaaaggg    2457
gaaacgtctc ccagatcgct cccttggctt tgaggccgaa gctgctgtga ctgtgtcccc    2517
ttactgagcg caagccacag cctgtcttgt caggtggacc ctgtaaatac atcctttttc    2577
tgctaaccct tcaacccct cgcctcctac tctgagacaa agaaaaaat attaaaaaaa     2637 tgcataggct taactcgctg atgagttaat tgttttattt ttaaactctt tttgggtcca    2697
gttgattgta cgtagccaca ggagccctgc tatgaaagga ataaaaccta cacacaaggt    2757
tggagctttg caattctttt tggaaaagag ctgggatccc acagccctag tatgaaagct    2817
gggggtgggg aggggccttt gctgcccttg gtttctgggg gctggttggc atttgctggc    2877
ctggcagggg gtgaaggcag gagttggggg caggtcagga ccaggaccca gggagaggct    2937
gtgtccctgc tggggtctca ggtccagctt tactgtggct gtctggatcc ttcccaaggt    2997
acagctgtat ataaacgtgt cccgagctta gattctgtat gcggtgacgg cggggtgtgg    3057
tggcctgtga ggggcccctg gcccaggagg aggattgtgc tgatgtagtg accaagtgca    3117
atatgggcgg gcagtcgctg cagggagcac cacggccaga agtaacttat tttgtactag    3177
tgtccgcata agaaaaagaa tcggcagtat tttctgtttt tatgttttat ttggcttgtt    3237
ttattttgga ttagtgaact aagttattgt taattatgta caacatttat atattgtctg    3297
taaaaaatgt atgctatcct cttattcctt taaagtgagt actgttaaga ataataaaat    3357 acttttttgtg aatgcccaaa aaaaaa                                         3383
```

<210> SEQ ID NO 14
<211> LENGTH: 480
<212> TYPE: PRT
<213> ORGANISM: Homo sapiens

<400> SEQUENCE: 14

```
Met Glu Val Ala Pro Glu Gln Pro Arg Trp Met Ala His Pro Ala Val
1               5                   10                  15

Leu Asn Ala Gln His Pro Asp Ser His His Pro Gly Leu Ala His Asn
            20                  25                  30

Tyr Met Glu Pro Ala Gln Leu Leu Pro Pro Asp Glu Val Asp Val Phe
        35                  40                  45

Phe Asn His Leu Asp Ser Gln Gly Asn Pro Tyr Tyr Ala Asn Pro Ala
    50                  55                  60

His Ala Arg Ala Arg Val Ser Tyr Ser Pro Ala His Ala Arg Leu Thr
65                  70                  75                  80

Gly Gly Gln Met Cys Arg Pro His Leu Leu His Ser Pro Gly Leu Pro
                85                  90                  95

Trp Leu Asp Gly Gly Lys Ala Ala Leu Ser Ala Ala Ala His His
            100                 105                 110

His Asn Pro Trp Thr Val Ser Pro Phe Ser Lys Thr Pro Leu His Pro
        115                 120                 125

Ser Ala Ala Gly Gly Pro Gly Gly Pro Leu Ser Val Tyr Pro Gly Ala
    130                 135                 140

Gly Gly Gly Ser Gly Gly Gly Ser Gly Ser Ser Val Ala Ser Leu Thr
145                 150                 155                 160

Pro Thr Ala Ala His Ser Gly Ser His Leu Phe Gly Phe Pro Pro Thr
                165                 170                 175
```

Pro Pro Lys Glu Val Ser Pro Asp Pro Ser Thr Thr Gly Ala Ala Ser
            180                 185                 190

Pro Ala Ser Ser Ser Ala Gly Gly Ser Ala Ala Arg Gly Glu Asp Lys
        195                 200                 205

Asp Gly Val Lys Tyr Gln Val Ser Leu Thr Glu Ser Met Lys Met Glu
    210                 215                 220

Ser Gly Ser Pro Leu Arg Pro Gly Leu Ala Thr Met Gly Thr Gln Pro
225                 230                 235                 240

Ala Thr His His Pro Ile Pro Thr Tyr Pro Ser Tyr Val Pro Ala Ala
                245                 250                 255

Ala His Asp Tyr Ser Ser Gly Leu Phe His Pro Gly Gly Phe Leu Gly
            260                 265                 270

Gly Pro Ala Ser Ser Phe Thr Pro Lys Gln Arg Ser Lys Ala Arg Ser
        275                 280                 285

Cys Ser Glu Gly Arg Glu Cys Val Asn Cys Gly Ala Thr Ala Thr Pro
    290                 295                 300

Leu Trp Arg Arg Asp Gly Thr Gly His Tyr Leu Cys Asn Ala Cys Gly
305                 310                 315                 320

Leu Tyr His Lys Met Asn Gly Gln Asn Arg Pro Leu Ile Lys Pro Lys
                325                 330                 335

Arg Arg Leu Ser Ala Ala Arg Arg Ala Gly Thr Cys Cys Ala Asn Cys
            340                 345                 350

Gln Thr Thr Thr Thr Thr Leu Trp Arg Arg Asn Ala Asn Gly Asp Pro
        355                 360                 365

Val Cys Asn Ala Cys Gly Leu Tyr Tyr Lys Leu His Asn Val Asn Arg
    370                 375                 380

Pro Leu Thr Met Lys Lys Glu Gly Ile Gln Thr Arg Asn Arg Lys Met
385                 390                 395                 400

Ser Asn Lys Ser Lys Lys Ser Lys Lys Gly Ala Glu Cys Phe Glu Glu
                405                 410                 415

Leu Ser Lys Cys Met Gln Glu Lys Ser Ser Pro Phe Ser Ala Ala Ala
            420                 425                 430

Leu Ala Gly His Met Ala Pro Val Gly His Leu Pro Pro Phe Ser His
        435                 440                 445

Ser Gly His Ile Leu Pro Thr Pro Thr Pro Ile His Pro Ser Ser Ser
    450                 455                 460

Leu Ser Phe Gly His Pro His Pro Ser Ser Met Val Thr Ala Met Gly
465                 470                 475                 480

```
<210> SEQ ID NO 15
<211> LENGTH: 3070
<212> TYPE: DNA
<213> ORGANISM: Homo sapiens
<220> FEATURE:
<221> NAME/KEY: CDS
<222> LOCATION: (558)..(1892)

<400> SEQUENCE: 15
ggcgccgtct tgatactttc agaaagaatg cattccctgt aaaaaaaaaa aaaaaatact      60
gagagaggga gagagagaga gaagaagaga gagagacgg gggagagcga gacagagcga     120
gcaacgcaat ctgaccgagc aggtcgtacg ccgccgcctc ctcctcctct ctgctcttcg     180
ctacccaggt gacccgagga gggactccgc ctccgagcgg ctgaggaccc cggtgcagag     240
gagcctggct cgcagaattg cagagtcgtc gccccttttt acaacctggt cccgttttat     300
```

```
tctgccgtac ccagtttttg gattttttgtc ttccccttct tctctttgct aaacgacccc    360
tccaagataa ttttaaaaa accttctcct ttgctcacct ttgcttccca gccttcccat     420 cccccaccg aaagcaaatc attcaacgac cccgaccct ccgacggcag gagcccccg       480 acctcccagg cggaccgccc tccctccccg cgcgcgggtt ccgggcccgg cgagagggcg    540
cgagcacagc cgaggcc atg gag gtg acg gcg gac cag ccg cgc tgg gtg        590
                  Met Glu Val Thr Ala Asp Gln Pro Arg Trp Val
                   1               5                       10 agc cac cac cac ccc gcc gtg ctc aac ggg cag cac ccg gac acg cac       638
Ser His His His Pro Ala Val Leu Asn Gly Gln His Pro Asp Thr His
            15                  20                  25 cac ccg ggc ctc agc cac tcc tac atg gac gcg gcg cag tac ccg ctg       686
His Pro Gly Leu Ser His Ser Tyr Met Asp Ala Ala Gln Tyr Pro Leu
        30                  35                  40 ccg gag gag gtg gat gtg ctt ttt aac atc gac ggt caa ggc aac cac       734
Pro Glu Glu Val Asp Val Leu Phe Asn Ile Asp Gly Gln Gly Asn His
45                  50                  55 gtc ccg ccc tac tac gga aac tcg gtc agg gcc acg gtg cag agg tac       782
Val Pro Pro Tyr Tyr Gly Asn Ser Val Arg Ala Thr Val Gln Arg Tyr
60                  65                  70                  75 cct ccg acc cac cac ggg agc cag gtg tgc cgc ccg cct ctg ctt cat       830
Pro Pro Thr His His Gly Ser Gln Val Cys Arg Pro Pro Leu Leu His
            80                  85                  90 gga tcc cta ccc tgg ctg gac ggc ggc aaa gcc ctg ggc agc cac cac       878
Gly Ser Leu Pro Trp Leu Asp Gly Gly Lys Ala Leu Gly Ser His His
        95                  100                 105 acc gcc tcc ccc tgg aat ctc agc ccc ttc tcc aag acg tcc atc cac       926
Thr Ala Ser Pro Trp Asn Leu Ser Pro Phe Ser Lys Thr Ser Ile His
        110                 115                 120 cac ggc tcc ccg ggg ccc ctc tcc gtc tac ccc ccg gcc tcg tcc tcc       974
His Gly Ser Pro Gly Pro Leu Ser Val Tyr Pro Pro Ala Ser Ser Ser
        125                 130                 135 tcc ttg tcg ggg ggc cac gcc agc ccg cac ctc ttc acc ttc ccg ccc      1022
Ser Leu Ser Gly Gly His Ala Ser Pro His Leu Phe Thr Phe Pro Pro
140                 145                 150                 155 acc ccg ccg aag gac gtc tcc ccg gac cca tcg ctg tcc acc cca ggc      1070
Thr Pro Pro Lys Asp Val Ser Pro Asp Pro Ser Leu Ser Thr Pro Gly
            160                 165                 170 tcg gcc ggc tcg gcc cgg cag gac gag aaa gag tgc ctc aag tac cag      1118
Ser Ala Gly Ser Ala Arg Gln Asp Glu Lys Glu Cys Leu Lys Tyr Gln
        175                 180                 185 gtg ccc ctg ccc gac agc atg aag ctg gag tcg tcc cac tcc cgt ggc      1166
Val Pro Leu Pro Asp Ser Met Lys Leu Glu Ser Ser His Ser Arg Gly
        190                 195                 200 agc atg acc gcc ctg ggt gga gcc tcc tcg tcg acc cac cac ccc atc      1214
Ser Met Thr Ala Leu Gly Gly Ala Ser Ser Ser Thr His His Pro Ile
205                 210                 215 acc acc tac ccg ccc tac gtg ccc gag tac agc tcc gga ctc ttc ccc      1262
Thr Thr Tyr Pro Pro Tyr Val Pro Glu Tyr Ser Ser Gly Leu Phe Pro
220                 225                 230                 235 ccc agc agc ctg ctg ggc ggc tcc ccc acc ggc ttc gga tgc aag tcc      1310
Pro Ser Ser Leu Leu Gly Gly Ser Pro Thr Gly Phe Gly Cys Lys Ser
            240                 245                 250 agg ccc aag gcc cgg tcc agc aca gaa ggc agg gag tgt gtg aac tgt      1358
Arg Pro Lys Ala Arg Ser Ser Thr Glu Gly Arg Glu Cys Val Asn Cys
        255                 260                 265 ggg gca acc tcg acc cca ctg tgg cgg cga gat ggc acg gga cac tac      1406
Gly Ala Thr Ser Thr Pro Leu Trp Arg Arg Asp Gly Thr Gly His Tyr
        270                 275                 280
```

| | | |
|---|---|---|
| ctg tgc aac gcc tgc ggg ctc tat cac aaa atg aac gga cag aac cgg<br>Leu Cys Asn Ala Cys Gly Leu Tyr His Lys Met Asn Gly Gln Asn Arg<br>     285                      290                   295 | | 1454 |
| ccc ctc att aag ccc aag cga agg ctg tct gca gcc agg aga gca ggg<br>Pro Leu Ile Lys Pro Lys Arg Arg Leu Ser Ala Ala Arg Arg Ala Gly<br>300                   305                 310                 315 | | 1502 |
| acg tcc tgt gcg aac tgt cag acc acc aca acc aca ctc tgg agg agg<br>Thr Ser Cys Ala Asn Cys Gln Thr Thr Thr Thr Thr Leu Trp Arg Arg<br>                  320                      325                 330 | | 1550 |
| aat gcc aat ggg gac cct gtc tgc aat gcc tgt ggg ctc tac tac aag<br>Asn Ala Asn Gly Asp Pro Val Cys Asn Ala Cys Gly Leu Tyr Tyr Lys<br>                  335                      340                 345 | | 1598 |
| ctt cac aat att aac aga ccc ctg act atg aag aag gaa ggc atc cag<br>Leu His Asn Ile Asn Arg Pro Leu Thr Met Lys Lys Glu Gly Ile Gln<br>                  350                      355                 360 | | 1646 |
| acc aga aac cga aaa atg tct agc aaa tcc aaa aag tgc aaa aaa gtg<br>Thr Arg Asn Arg Lys Met Ser Ser Lys Ser Lys Lys Cys Lys Lys Val<br>                  365                      370                 375 | | 1694 |
| cat gac tca ctg gag gac ttc ccc aag aac agc tcg ttt aac ccg gcc<br>His Asp Ser Leu Glu Asp Phe Pro Lys Asn Ser Ser Phe Asn Pro Ala<br>380                   385                 390                 395 | | 1742 |
| gcc ctc tcc aga cac atg tcc tcc ctg agc cac atc tcg ccc ttc agc<br>Ala Leu Ser Arg His Met Ser Ser Leu Ser His Ile Ser Pro Phe Ser<br>                  400                      405                 410 | | 1790 |
| cac tcc agc cac atg ctg acc acg ccc acg ccg atg cac ccg cca tcc<br>His Ser Ser His Met Leu Thr Thr Pro Thr Pro Met His Pro Pro Ser<br>                  415                      420                 425 | | 1838 |
| agc ctg tcc ttt gga cca cac cac ccc tcc agc atg gtc acc gcc atg<br>Ser Leu Ser Phe Gly Pro His His Pro Ser Ser Met Val Thr Ala Met<br>                  430                      435                 440 | | 1886 |
| ggt tag agccctgctc gatgctcaca gggcccccag cgagagtccc tgcagtccct<br>Gly | | 1942 |
| ttcgacttgc attttgcag gagcagtatc atgaagccta aacgcgatgg atatatgttt | | 2002 |
| ttgaaggcag aaagcaaaat tatgtttgcc actttgcaaa ggagctcact gtggtgtctg | | 2062 |
| tgttccaacc actgaatctg gaccccatct gtgaataagc cattctgact catatcccct | | 2122 |
| atttaacagg gtctctagtg ctgtgaaaaa aaaaatgctg aacattgcat ataacttata | | 2182 |
| ttgtaagaaa tactgtacaa tgactttatt gcatctgggt agctgtaagg catgaaggat | | 2242 |
| gccaagaagt ttaaggaata tgggagaaat agtgtggaaa ttaagaagaa actaggtctg | | 2302 |
| atattcaaat ggacaaactg ccagttttgt ttcctttcac tggccacagt tgtttgatgc | | 2362 |
| attaaaagaa aataaaaaaa agaaaaaaga gaaagaaaa aaaagaaaa agttgtagg | | 2422 |
| cgaatcattt gttcaaagct gttggcctct gcaaaggaaa taccagttct gggcaatcag | | 2482 |
| tgttaccgtt caccagttgc cgttgagggt tcagagagc ttttctag gcctacatgc | | 2542 |
| tttgtgaaca agtccctgta attgttgttt gtatgtataa ttcaaagcac caaaataaga | | 2602 |
| aaagatgtag atttatttca tcatattata cagaccgaac tgttgtataa atttatttac | | 2662 |
| tgctagtcct aagaactgct ttctttcgtt tgtttgtttc aatattttcc ttctctctca | | 2722 |
| atttttggtt gaataaacta gattacattc agttggccta aggtggttgt gctcggaggg | | 2782 |
| tttcttgttt cttttccatt ttgttttggg atgatattta ttaaatagct tctaagagtc | | 2842 |
| cggcggcatc tgtcttgtcc ctattcctgc agcctgtgct gagggtagca gtgtatgagc | | 2902 |
| taccagcgtg catgtcagcg accctggccc gacaggccac gtcctgcaat cggcccggct | | 2962 |
| gcctcttcgc cctgtcgtgt tctgtgttag tgatcactgc ctttaataca gtctgttgga | | 3022 | ataatattat aagcataata ataaagtgaa aatattttaa aactacaa                3070

<210> SEQ ID NO 16
<211> LENGTH: 444
<212> TYPE: PRT
<213> ORGANISM: Homo sapiens

<400> SEQUENCE: 16

```
Met Glu Val Thr Ala Asp Gln Pro Arg Trp Val Ser His His Pro
1               5                   10                  15

Ala Val Leu Asn Gly Gln His Pro Asp Thr His His Pro Gly Leu Ser
                20                  25                  30

His Ser Tyr Met Asp Ala Ala Gln Tyr Pro Leu Pro Glu Glu Val Asp
            35                  40                  45

Val Leu Phe Asn Ile Asp Gly Gln Gly Asn His Val Pro Pro Tyr Tyr
    50                  55                  60

Gly Asn Ser Val Arg Ala Thr Val Gln Arg Tyr Pro Pro Thr His His
65                  70                  75                  80

Gly Ser Gln Val Cys Arg Pro Pro Leu Leu His Gly Ser Leu Pro Trp
                85                  90                  95

Leu Asp Gly Gly Lys Ala Leu Gly Ser His His Thr Ala Ser Pro Trp
                100                 105                 110

Asn Leu Ser Pro Phe Ser Lys Thr Ser Ile His Gly Ser Pro Gly
                115                 120                 125

Pro Leu Ser Val Tyr Pro Pro Ala Ser Ser Ser Leu Ser Gly Gly
    130                 135                 140

His Ala Ser Pro His Leu Phe Thr Phe Pro Pro Thr Pro Pro Lys Asp
145                 150                 155                 160

Val Ser Pro Asp Pro Ser Leu Ser Thr Pro Gly Ser Ala Gly Ser Ala
                165                 170                 175

Arg Gln Asp Glu Lys Glu Cys Leu Lys Tyr Gln Val Pro Leu Pro Asp
            180                 185                 190

Ser Met Lys Leu Glu Ser Ser His Ser Arg Gly Ser Met Thr Ala Leu
        195                 200                 205

Gly Gly Ala Ser Ser Ser Thr His His Pro Ile Thr Thr Tyr Pro Pro
    210                 215                 220

Tyr Val Pro Glu Tyr Ser Ser Gly Leu Phe Pro Pro Ser Ser Leu Leu
225                 230                 235                 240

Gly Gly Ser Pro Thr Gly Phe Gly Cys Lys Ser Arg Pro Lys Ala Arg
                245                 250                 255

Ser Ser Thr Glu Gly Arg Glu Cys Val Asn Cys Gly Ala Thr Ser Thr
            260                 265                 270

Pro Leu Trp Arg Arg Asp Gly Thr Gly His Tyr Leu Cys Asn Ala Cys
        275                 280                 285

Gly Leu Tyr His Lys Met Asn Gly Gln Asn Arg Pro Leu Ile Lys Pro
    290                 295                 300

Lys Arg Arg Leu Ser Ala Ala Arg Ala Gly Thr Ser Cys Ala Asn
305                 310                 315                 320

Cys Gln Thr Thr Thr Thr Thr Leu Trp Arg Arg Asn Ala Asn Gly Asp
                325                 330                 335

Pro Val Cys Asn Ala Cys Gly Leu Tyr Tyr Lys Leu His Asn Ile Asn
            340                 345                 350

Arg Pro Leu Thr Met Lys Lys Glu Gly Ile Gln Thr Arg Asn Arg Lys
        355                 360                 365
```

```
Met Ser Ser Lys Ser Lys Lys Cys Lys Lys Val His Asp Ser Leu Glu
    370             375             380
Asp Phe Pro Lys Asn Ser Ser Phe Asn Pro Ala Ala Leu Ser Arg His
385             390             395             400
Met Ser Ser Leu Ser His Ile Ser Pro Phe Ser His Ser Ser His Met
            405             410             415
Leu Thr Thr Pro Thr Pro Met His Pro Pro Ser Ser Leu Ser Phe Gly
            420             425             430
Pro His His Pro Ser Ser Met Val Thr Ala Met Gly
            435             440

<210> SEQ ID NO 17
<211> LENGTH: 1423
<212> TYPE: DNA
<213> ORGANISM: Homo sapiens
<220> FEATURE:
<221> NAME/KEY: CDS
<222> LOCATION: (224)..(1036)

<400> SEQUENCE: 17
gactatctcc cagcggcagg cccttcgata aaatcaggaa cttgtgctgg ccctgcaatg      60
tcaagggagg gggctcaccc agggctcctg tagctcaggg ggcaggcctg agccctgcac     120
ccgccccacg accgtccagc ccctgacggg gcaccccatc ctgaggggct ctgcattggc     180
ccccaccgag gcagggggatc tgaccgactc ggagcccggc tgg atg tta cag gcg     235
                                              Met Leu Gln Ala
                                                1 tgc aaa atg gaa ggg ttt ccc ctc gtc ccc cct cca tca gaa gac ctg      283
Cys Lys Met Glu Gly Phe Pro Leu Val Pro Pro Pro Ser Glu Asp Leu
  5              10              15              20 gtg ccc tat gac acg gat cta tac caa cgc caa acg cac gag tat tac      331
Val Pro Tyr Asp Thr Asp Leu Tyr Gln Arg Gln Thr His Glu Tyr Tyr
                25              30              35 ccc tat ctc agc agt gat ggg gag agc cat agc gac cat tac tgg gac      379
Pro Tyr Leu Ser Ser Asp Gly Glu Ser His Ser Asp His Tyr Trp Asp
            40              45              50 ttc cac ccc cac cac gtg cac agc gag ttc gag agc ttc gcc gag aac      427
Phe His Pro His His Val His Ser Glu Phe Glu Ser Phe Ala Glu Asn
        55              60              65 aac ttc acg gag ctc cag agc gtg cag ccc ccg cag ctg cag cag ctc      475
Asn Phe Thr Glu Leu Gln Ser Val Gln Pro Pro Gln Leu Gln Gln Leu
    70              75              80 tac cgc cac atg gag ctg gag cag atg cac gtc ctc gat acc ccc atg      523
Tyr Arg His Met Glu Leu Glu Gln Met His Val Leu Asp Thr Pro Met
85              90              95             100 gtg cca ccc cat ccc agt ctt ggc cac cag gtc tcc tac ctg ccc cgg      571
Val Pro Pro His Pro Ser Leu Gly His Gln Val Ser Tyr Leu Pro Arg
            105             110             115 atg tgc ctc cag tac cca tcc ctg tcc cca gcc cag ccc agc tca gat      619
Met Cys Leu Gln Tyr Pro Ser Leu Ser Pro Ala Gln Pro Ser Ser Asp
        120             125             130 gag gag gag ggc gag cgg cag agc ccc cca ctg gag gtg tct gac ggc      667
Glu Glu Glu Gly Glu Arg Gln Ser Pro Pro Leu Glu Val Ser Asp Gly
    135             140             145 gag gcg gat ggc ctg gag ccc ggg cct ggg ctc ctg cct ggg gag aca      715
Glu Ala Asp Gly Leu Glu Pro Gly Pro Gly Leu Leu Pro Gly Glu Thr
150             155             160 ggc agc aag aag aag atc cgc ctg tac cag ttc ctg ttg gac ctg ctc      763
Gly Ser Lys Lys Lys Ile Arg Leu Tyr Gln Phe Leu Leu Asp Leu Leu
```

```
cgc agc ggc gac atg aag gac agc atc tgg tgg gtg gac aag gac aag        811
Arg Ser Gly Asp Met Lys Asp Ser Ile Trp Trp Val Asp Lys Asp Lys
                185                 190                 195 ggc acc ttc cag ttc tcg tcc aag cac aag gag gcg ctg gcg cac cgc        859
Gly Thr Phe Gln Phe Ser Ser Lys His Lys Glu Ala Leu Ala His Arg
    200                 205                 210 tgg ggc atc cag aag ggc aac cgc aag aag atg acc tac cag aag atg        907
Trp Gly Ile Gln Lys Gly Asn Arg Lys Lys Met Thr Tyr Gln Lys Met
215                 220                 225 gcg cgc gcg ctg cgc aac tac ggc aag acg ggc gag gtc aag aag gtg        955
Ala Arg Ala Leu Arg Asn Tyr Gly Lys Thr Gly Glu Val Lys Lys Val
        230                 235                 240 aag aag aag ctc acc tac cag ttc agc ggc gaa gtg ctg ggc cgc ggg       1003
Lys Lys Lys Leu Thr Tyr Gln Phe Ser Gly Glu Val Leu Gly Arg Gly
245                 250                 255                 260 ggc ctg gcc gag cgg cgc cac ccg ccc cac tga gcccgcagcc ccgccgggc      1056
Gly Leu Ala Glu Arg Arg His Pro Pro His
                265                 270 cccgccaggc ctccccgctg gccatagcat taagccctcg cccggcccgg acacagggag     1116
gacgctcccg gggcccagag gcaggactgt ggcgggccgg gcctcgcctc acccgccccc     1176 tcccccact ccaggccccc tccacatccc gcttcgcctc cctccaggac tccaccccgg      1236
ctcccggacg ccagctgggc gtcagacccc accggggcaa ccttgcagag gacgacccgg     1296
ggtactgcct tgggagtctc aagtccgtat gtaaatcaga tctcccctct caccccctccc   1356 acccattaac ctcctcccaa aaacaagta aagttattct caatccatca aaaaaaaaaa     1416
aaaaaaa                                                              1423

<210> SEQ ID NO 18
<211> LENGTH: 270
<212> TYPE: PRT
<213> ORGANISM: Homo sapiens

<400> SEQUENCE: 18

Met Leu Gln Ala Cys Lys Met Glu Gly Phe Pro Leu Val Pro Pro Pro
1               5                   10                  15

Ser Glu Asp Leu Val Pro Tyr Asp Thr Asp Leu Tyr Gln Arg Gln Thr
            20                  25                  30

His Glu Tyr Tyr Pro Tyr Leu Ser Ser Asp Gly Glu Ser His Ser Asp
        35                  40                  45

His Tyr Trp Asp Phe His Pro His His Val His Ser Glu Phe Glu Ser
    50                  55                  60

Phe Ala Glu Asn Asn Phe Thr Glu Leu Gln Ser Val Gln Pro Pro Gln
65                  70                  75                  80

Leu Gln Gln Leu Tyr Arg His Met Glu Leu Glu Gln Met His Val Leu
                85                  90                  95

Asp Thr Pro Met Val Pro Pro His Pro Ser Leu Gly His Gln Val Ser
            100                 105                 110

Tyr Leu Pro Arg Met Cys Leu Gln Tyr Pro Ser Leu Ser Pro Ala Gln
        115                 120                 125

Pro Ser Ser Asp Glu Glu Gly Glu Arg Gln Ser Pro Pro Leu Glu
    130                 135                 140

Val Ser Asp Gly Glu Ala Asp Gly Leu Glu Pro Gly Pro Gly Leu Leu
145                 150                 155                 160

Pro Gly Glu Thr Gly Ser Lys Lys Lys Ile Arg Leu Tyr Gln Phe Leu
```

```
                    165                 170                 175
Leu Asp Leu Leu Arg Ser Gly Asp Met Lys Asp Ser Ile Trp Trp Val
            180                 185                 190

Asp Lys Asp Lys Gly Thr Phe Gln Phe Ser Ser Lys His Lys Glu Ala
        195                 200                 205

Leu Ala His Arg Trp Gly Ile Gln Lys Gly Asn Arg Lys Lys Met Thr
    210                 215                 220

Tyr Gln Lys Met Ala Arg Ala Leu Arg Asn Tyr Gly Lys Thr Gly Glu
225                 230                 235                 240

Val Lys Lys Val Lys Lys Leu Thr Tyr Gln Phe Ser Gly Glu Val
                245                 250                 255

Leu Gly Arg Gly Gly Leu Ala Glu Arg His Pro Pro His
            260                 265                 270

<210> SEQ ID NO 19
<211> LENGTH: 9
<212> TYPE: PRT
<213> ORGANISM: Artificial Sequence
<220> FEATURE:
<223> OTHER INFORMATION: Synthetic peptide

<400> SEQUENCE: 19

Arg Lys Lys Arg Arg Gln Arg Arg Arg
1               5

<210> SEQ ID NO 20
<211> LENGTH: 11
<212> TYPE: PRT
<213> ORGANISM: Artificial Sequence
<220> FEATURE:
<223> OTHER INFORMATION: Synthetic peptide

<400> SEQUENCE: 20

Tyr Gly Arg Lys Lys Arg Arg Gln Arg Arg Arg
1               5                   10

<210> SEQ ID NO 21
<211> LENGTH: 17
<212> TYPE: PRT
<213> ORGANISM: Artificial Sequence
<220> FEATURE:
<223> OTHER INFORMATION: Synthetic peptide

<400> SEQUENCE: 21

Ala Lys Ile Trp Phe Gln Asn Arg Arg Met Lys Trp Lys Lys Glu Asn
1               5                   10                  15
Asn

<210> SEQ ID NO 22
<211> LENGTH: 34
<212> TYPE: PRT
<213> ORGANISM: Artificial Sequence
<220> FEATURE:
<223> OTHER INFORMATION: Synthetic peptide

<400> SEQUENCE: 22

Asp Ala Ala Thr Ala Thr Arg Gly Arg Ser Ala Ser Arg Pro Thr
1               5                   10                  15

Glu Arg Pro Arg Ala Pro Ala Arg Ser Ala Ser Arg Pro Arg Arg Pro
                20                  25                  30

Val Glu
```

<210> SEQ ID NO 23
<211> LENGTH: 11
<212> TYPE: PRT
<213> ORGANISM: Artificial Sequence
<220> FEATURE:
<223> OTHER INFORMATION: Synthetic peptide

<400> SEQUENCE: 23

Tyr Ala Arg Lys Ala Arg Arg Gln Ala Arg Arg
1               5                   10

<210> SEQ ID NO 24
<211> LENGTH: 11
<212> TYPE: PRT
<213> ORGANISM: Artificial Sequence
<220> FEATURE:
<223> OTHER INFORMATION: Synthetic peptide

<400> SEQUENCE: 24

Tyr Ala Arg Ala Ala Arg Arg Ala Ala Arg Arg
1               5                   10

<210> SEQ ID NO 25
<211> LENGTH: 11
<212> TYPE: PRT
<213> ORGANISM: Artificial Sequence
<220> FEATURE:
<223> OTHER INFORMATION: Synthetic peptide

<400> SEQUENCE: 25

Tyr Ala Arg Ala Ala Arg Arg Ala Ala Arg Ala
1               5                   10

<210> SEQ ID NO 26
<211> LENGTH: 11
<212> TYPE: PRT
<213> ORGANISM: Artificial Sequence
<220> FEATURE:
<223> OTHER INFORMATION: Synthetic peptide

<400> SEQUENCE: 26

Tyr Ala Arg Ala Ala Ala Arg Gln Ala Arg Ala
1               5                   10

<210> SEQ ID NO 27
<211> LENGTH: 1490
<212> TYPE: DNA
<213> ORGANISM: Homo sapiens
<220> FEATURE:
<221> NAME/KEY: CDS
<222> LOCATION: (440)..(1468)

<400> SEQUENCE: 27

```
gcagataagc ccagcttagc ccagctgacc ccagaccctc tcccctcact cccccatgt      60 cgcaggatcg agaccctgag gcagacagcc cgttcaccaa gcccccgcc ccgccccat      120 caccccgtaa acttctccca gcctccgccc tgccctcacc cagcccgctg ttccccaagc    180
ctcgctccaa gccacgcca cccctgcagc agggcagccc cagaggccag cacctatccc     240
cgaggctggg gtcgaggctc ggccccgccc ctgcctctgc aacttgagcc tggctgcgac    300
ccctgctctg acgtctcgga aaattccccc ttgcccaggc ccttggggga ggggtgcat     360 ggtatgaaat ggggctgaga ccccccggctg ggggcagagg aacccgccag agaacattca   420
gaaggccttc atcgcatcc atg gac ctg tgg aac tgg gat gag gca tcc cca     472
                     Met Asp Leu Trp Asn Trp Asp Glu Ala Ser Pro
```

-continued

```
            1               5                  10
cag gaa gtg cct cca ggg aac aag ctg gca ggg ctt gaa gga gcc aaa       520
Gln Glu Val Pro Pro Gly Asn Lys Leu Ala Gly Leu Glu Gly Ala Lys
            15                  20                  25 tta ggc ttc tgt ttc cct gat ctg gca ctc caa ggg gac acg ccg aca       568
Leu Gly Phe Cys Phe Pro Asp Leu Ala Leu Gln Gly Asp Thr Pro Thr
            30                  35                  40 gcg aca gca gag aca tgc tgg aaa ggt aca agc tca tcc ctg gca agc       616
Ala Thr Ala Glu Thr Cys Trp Lys Gly Thr Ser Ser Ser Leu Ala Ser
        45                  50                  55 ttc cca cag ctg gac tgg ggc tcc gcg tta ctg cac cca gaa gtt cca       664
Phe Pro Gln Leu Asp Trp Gly Ser Ala Leu Leu His Pro Glu Val Pro
60                  65                  70                  75 tgg ggg gcg gag ccc gac tct cag gct ctt ccg tgg tcc ggg gac tgg       712
Trp Gly Ala Glu Pro Asp Ser Gln Ala Leu Pro Trp Ser Gly Asp Trp
                80                  85                  90 aca gac atg gcg tgc aca gcc tgg gac tct tgg agc ggc gcc tcg cag       760
Thr Asp Met Ala Cys Thr Ala Trp Asp Ser Trp Ser Gly Ala Ser Gln
                    95                  100                 105 acc ctg ggc ccc gcc cct ctc ggc ccg ggc ccc atc ccc gcc gcc ggc       808
Thr Leu Gly Pro Ala Pro Leu Gly Pro Gly Pro Ile Pro Ala Ala Gly
            110                 115                 120 tcc gaa ggc gcc gcg ggc cag aac tgc gtc ccc gtg gcg gga gag gcc       856
Ser Glu Gly Ala Ala Gly Gln Asn Cys Val Pro Val Ala Gly Glu Ala
            125                 130                 135 acc tcg tgg tcg cgc gcc cag gcc gcc ggg agc aac acc agc tgg gac       904
Thr Ser Trp Ser Arg Ala Gln Ala Ala Gly Ser Asn Thr Ser Trp Asp
140                 145                 150                 155 tgt tct gtg ggg ccc gac ggc gat acc tac tgg ggc agt ggc ctg ggc       952
Cys Ser Val Gly Pro Asp Gly Asp Thr Tyr Trp Gly Ser Gly Leu Gly
                    160                 165                 170 ggg gag ccg cgc acg gac tgt acc att tcg tgg ggc ggg ccc gcg ggc       1000
Gly Glu Pro Arg Thr Asp Cys Thr Ile Ser Trp Gly Gly Pro Ala Gly
            175                 180                 185 ccg gac tgt acc acc tcc tgg aac ccg ggg ctg cat gcg ggt ggc acc       1048
Pro Asp Cys Thr Thr Ser Trp Asn Pro Gly Leu His Ala Gly Gly Thr
            190                 195                 200 acc tct ttg aag cgg tac cag agc tca gct ctc acc gtt tgc tcc gaa       1096
Thr Ser Leu Lys Arg Tyr Gln Ser Ser Ala Leu Thr Val Cys Ser Glu
            205                 210                 215 ccg agc ccg cag tcg gac cgt gcc agt ttg gct cga tgc ccc aaa act       1144
Pro Ser Pro Gln Ser Asp Arg Ala Ser Leu Ala Arg Cys Pro Lys Thr
220                 225                 230                 235 aac cac cga ggt ccc att cag ctg tgg cag ttc ctc ctg gag ctg ctc       1192
Asn His Arg Gly Pro Ile Gln Leu Trp Gln Phe Leu Leu Glu Leu Leu
                    240                 245                 250 cac gac ggg gcg cgt agc agc tgc atc cgt tgg act ggc aac agc cgc       1240
His Asp Gly Ala Arg Ser Ser Cys Ile Arg Trp Thr Gly Asn Ser Arg
            255                 260                 265 gag ttc cag ctg tgc gac ccc aaa gag gtg gct cgg ctg tgg ggc gag       1288
Glu Phe Gln Leu Cys Asp Pro Lys Glu Val Ala Arg Leu Trp Gly Glu
            270                 275                 280 cgc aag aga aag ccg ggc atg aat tac gag aag ctg agc cgg ggc ctt       1336
Arg Lys Arg Lys Pro Gly Met Asn Tyr Glu Lys Leu Ser Arg Gly Leu
            285                 290                 295 cgc tac tac tat cgc cgc gac atc gtg cgc aag agc ggg gga cga aag       1384
Arg Tyr Tyr Tyr Arg Arg Asp Ile Val Arg Lys Ser Gly Gly Arg Lys
300                 305                 310                 315 tac acg tac cgc ttc ggg ggc cgc gtg ccc agc cta gcc tat ccg gac       1432
```

```
Tyr Thr Tyr Arg Phe Gly Gly Arg Val Pro Ser Leu Ala Tyr Pro Asp
            320                 325                 330 tgt gcg gga ggc gga cgg gga gca gag aca caa taa aaattcccgg                      1478
Cys Ala Gly Gly Gly Arg Gly Ala Glu Thr Gln
            335                 340 tcaaacctca aa                                                                   1490

<210> SEQ ID NO 28
<211> LENGTH: 342
<212> TYPE: PRT
<213> ORGANISM: Homo sapiens

<400> SEQUENCE: 28

Met Asp Leu Trp Asn Trp Asp Glu Ala Ser Pro Gln Glu Val Pro Pro
1               5                   10                  15

Gly Asn Lys Leu Ala Gly Leu Glu Gly Ala Lys Leu Gly Phe Cys Phe
            20                  25                  30

Pro Asp Leu Ala Leu Gln Gly Asp Thr Pro Thr Ala Thr Ala Glu Thr
            35                  40                  45

Cys Trp Lys Gly Thr Ser Ser Leu Ala Ser Phe Pro Gln Leu Asp
    50                  55                  60

Trp Gly Ser Ala Leu Leu His Pro Glu Val Pro Trp Gly Ala Glu Pro
65                  70                  75                  80

Asp Ser Gln Ala Leu Pro Trp Ser Gly Asp Trp Thr Asp Met Ala Cys
                85                  90                  95

Thr Ala Trp Asp Ser Trp Ser Gly Ala Ser Gln Thr Leu Gly Pro Ala
            100                 105                 110

Pro Leu Gly Pro Gly Pro Ile Pro Ala Ala Gly Ser Glu Gly Ala Ala
            115                 120                 125

Gly Gln Asn Cys Val Pro Val Ala Gly Glu Ala Thr Ser Trp Ser Arg
        130                 135                 140

Ala Gln Ala Ala Gly Ser Asn Thr Ser Trp Asp Cys Ser Val Gly Pro
145                 150                 155                 160

Asp Gly Asp Thr Tyr Trp Gly Ser Gly Leu Gly Gly Glu Pro Arg Thr
                165                 170                 175

Asp Cys Thr Ile Ser Trp Gly Gly Pro Ala Gly Pro Asp Cys Thr Thr
            180                 185                 190

Ser Trp Asn Pro Gly Leu His Ala Gly Gly Thr Thr Ser Leu Lys Arg
        195                 200                 205

Tyr Gln Ser Ser Ala Leu Thr Val Cys Ser Glu Pro Ser Pro Gln Ser
    210                 215                 220

Asp Arg Ala Ser Leu Ala Arg Cys Pro Lys Thr Asn His Arg Gly Pro
225                 230                 235                 240

Ile Gln Leu Trp Gln Phe Leu Leu Glu Leu Leu His Asp Gly Ala Arg
                245                 250                 255

Ser Ser Cys Ile Arg Trp Thr Gly Asn Ser Arg Glu Phe Gln Leu Cys
            260                 265                 270

Asp Pro Lys Glu Val Ala Arg Leu Trp Gly Glu Arg Lys Arg Lys Pro
            275                 280                 285

Gly Met Asn Tyr Glu Lys Leu Ser Arg Gly Leu Arg Tyr Tyr Tyr Arg
        290                 295                 300

Arg Asp Ile Val Arg Lys Ser Gly Gly Arg Lys Tyr Thr Tyr Arg Phe
305                 310                 315                 320

Gly Gly Arg Val Pro Ser Leu Ala Tyr Pro Asp Cys Ala Gly Gly Gly
                325                 330                 335
```

```
Arg Gly Ala Glu Thr Gln
            340

<210> SEQ ID NO 29
<211> LENGTH: 1801
<212> TYPE: DNA
<213> ORGANISM: Homo sapiens
<220> FEATURE:
<221> NAME/KEY: CDS
<222> LOCATION: (152)..(1144)

<400> SEQUENCE: 29
aaaaaggaga agtatctatt tgtgcaaaga gtcacacagt tgacagagtg gaggccagtc      60
ccgagagagg ctttgcagtt cccacctcgg gaagctccgg cagaacccag gcgagggaca     120
gctccggaca ggtgtggggt gcacactgaa a atg cca cgc tcc ttc ctg gtg       172
                                  Met Pro Arg Ser Phe Leu Val
                                   1               5 aag agc aag aag gct cac acc tac cac cag ccc cgt gtg cag gaa gat      220
Lys Ser Lys Lys Ala His Thr Tyr His Gln Pro Arg Val Gln Glu Asp
         10                  15                  20 gaa ccg ctc tgg cct cct gcc ctt acc ccg gtg ccc aga gac cag gct      268
Glu Pro Leu Trp Pro Pro Ala Leu Thr Pro Val Pro Arg Asp Gln Ala
     25                  30                  35 cca agc aac agc cct gtc ctt agc act cta ttc cca aac cag tgc ctg      316
Pro Ser Asn Ser Pro Val Leu Ser Thr Leu Phe Pro Asn Gln Cys Leu
 40                  45                  50                  55 gac tgg acc aac ctc aaa cga gag ccg gag ctg gag cag gac cag aac      364
Asp Trp Thr Asn Leu Lys Arg Glu Pro Glu Leu Glu Gln Asp Gln Asn
                 60                  65                  70 ttg gcc agg atg gcc ccg gca cca gag ggc ccc att gtg ctg tcc cga      412
Leu Ala Arg Met Ala Pro Ala Pro Glu Gly Pro Ile Val Leu Ser Arg
         75                  80                  85 ccc cag gat ggg gac tct cca ctg tcc gac tca ccc cca ttc tac aag      460
Pro Gln Asp Gly Asp Ser Pro Leu Ser Asp Ser Pro Pro Phe Tyr Lys
     90                  95                 100 cct agc ttc tcc tgg gac acc ttg gcc aca acc tat ggc cac agc tac      508
Pro Ser Phe Ser Trp Asp Thr Leu Ala Thr Thr Tyr Gly His Ser Tyr
105                 110                 115 cgg cag gcc ccc tcc acc atg cag tca gcc ttc ctg gag cac tcc gtc      556
Arg Gln Ala Pro Ser Thr Met Gln Ser Ala Phe Leu Glu His Ser Val
120                 125                 130                 135 agc ctg tac ggc agt cct ctt gtg ccc agc act gag ccc gcc ttg gac      604
Ser Leu Tyr Gly Ser Pro Leu Val Pro Ser Thr Glu Pro Ala Leu Asp
                140                 145                 150 ttc agc ctc cgc tac tcc cca ggc atg gat gcg tac cac tgt gtg aag      652
Phe Ser Leu Arg Tyr Ser Pro Gly Met Asp Ala Tyr His Cys Val Lys
        155                 160                 165 tgc aac aag gtc ttc tcc acc cct cac ggg ctc gaa gtg cat gtg cga      700
Cys Asn Lys Val Phe Ser Thr Pro His Gly Leu Glu Val His Val Arg
    170                 175                 180 cgc tcc cat agt ggg acc cgg ccc ttc gcc tgt gac atc tgc ggc aaa      748
Arg Ser His Ser Gly Thr Arg Pro Phe Ala Cys Asp Ile Cys Gly Lys
185                 190                 195 acc ttc ggc cac gct gtg agc ctg gag cag cac acg cac gtc cac tcc      796
Thr Phe Gly His Ala Val Ser Leu Glu Gln His Thr His Val His Ser
200                 205                 210                 215 cag gag cgc agc ttc gag tgc cgc atg tgc ggc aag gcc ttc aag cgc      844
Gln Glu Arg Ser Phe Glu Cys Arg Met Cys Gly Lys Ala Phe Lys Arg
                220                 225                 230
```

```
tcg tcc acg ctg tcc acc cac ctg ctc atc cac tca gac acg cgg ccc      892
Ser Ser Thr Leu Ser Thr His Leu Leu Ile His Ser Asp Thr Arg Pro
            235                 240                 245 tac ccc tgc cag ttc tgc ggc aag cgt ttc cac cag aag tcc gac atg      940
Tyr Pro Cys Gln Phe Cys Gly Lys Arg Phe His Gln Lys Ser Asp Met
        250                 255                 260 aag aag cac acc tac atc cac aca ggt gag aag ccg cac aag tgc cag      988
Lys Lys His Thr Tyr Ile His Thr Gly Glu Lys Pro His Lys Cys Gln
265                 270                 275 gtg tgc gga aag gcc ttc agc cag agc tcc aac ctc atc acc cac agc     1036
Val Cys Gly Lys Ala Phe Ser Gln Ser Ser Asn Leu Ile Thr His Ser
280                 285                 290                 295 cgc aag cac aca ggc ttc aag ccc ttc agc tgt gag ctg tgc acc aaa     1084
Arg Lys His Thr Gly Phe Lys Pro Phe Ser Cys Glu Leu Cys Thr Lys
            300                 305                 310 ggc ttc cag cgc aag gtg gac ctg cgg cgg cac cgc gag agc cag cac     1132
Gly Phe Gln Arg Lys Val Asp Leu Arg Arg His Arg Glu Ser Gln His
        315                 320                 325 aat ctc aag tga ggctgcgccg gctcccagct cctggccagc ctgccctgcg         1184
Asn Leu Lys
        330 gtcctgtcac ctggaggcca gcctcacatg cccaaatctc cagtctcctg gaggtgggac   1244 tggacaggag tctaccagct tgttttgaga ctcatgaaat tgctgtgtga ccttgggcaa   1304 gtcacttacc ctgtctggat caacatttct cctgctgcca agtgtgggag cctggctggg   1364 tctttctcag cagaagttgt ttccaggtgt gctcaagtgc cttcctctag cagagcacag   1424 aaagctagaa taccccagg gagacaggga tgccaagagt agaccagagc tgggacccac    1484 agacagaacc tccacctgcc tgctgcccac tgagctggga cctggtcacc ttggatttta   1544 gccggcctct ttctggctat aacaggcaga gtcggagctg cctcccaccc cagtcagaag   1604 cctggcaccc cctctgcttc ggccagatgt gctggctgac tccgacttcc gaccagcact   1664 cagctggcct ctggggattc tagctccaca accaggccgt gaggctggag aaactggcag   1724 ttattgctgt caaaagcctg ttctctcaac tgctgtcaat aaaattaaag atacagattt   1784 gctgccaaaa aaaaaaa                                                  1801

<210> SEQ ID NO 30
<211> LENGTH: 330
<212> TYPE: PRT
<213> ORGANISM: Homo sapiens

<400> SEQUENCE: 30

Met Pro Arg Ser Phe Leu Val Lys Ser Lys Lys Ala His Thr Tyr His
1               5                   10                  15

Gln Pro Arg Val Gln Glu Asp Glu Pro Leu Trp Pro Ala Leu Thr
            20                  25                  30

Pro Val Pro Arg Asp Gln Ala Pro Ser Asn Ser Pro Val Leu Ser Thr
        35                  40                  45

Leu Phe Pro Asn Gln Cys Leu Asp Trp Thr Asn Leu Lys Arg Glu Pro
    50                  55                  60

Glu Leu Glu Gln Asp Gln Asn Leu Ala Arg Met Ala Pro Ala Pro Glu
65                  70                  75                  80

Gly Pro Ile Val Leu Ser Arg Pro Gln Asp Gly Asp Ser Pro Leu Ser
                85                  90                  95

Asp Ser Pro Pro Phe Tyr Lys Ser Phe Ser Trp Asp Thr Leu Ala
            100                 105                 110
```

```
Thr Thr Tyr Gly His Ser Tyr Arg Gln Ala Pro Ser Thr Met Gln Ser
        115                 120                 125

Ala Phe Leu Glu His Ser Val Ser Leu Tyr Gly Ser Pro Leu Val Pro
        130                 135                 140

Ser Thr Glu Pro Ala Leu Asp Phe Ser Leu Arg Tyr Ser Pro Gly Met
145                 150                 155                 160

Asp Ala Tyr His Cys Val Lys Cys Asn Lys Val Phe Ser Thr Pro His
                165                 170                 175

Gly Leu Glu Val His Val Arg Arg Ser His Ser Gly Thr Arg Pro Phe
                180                 185                 190

Ala Cys Asp Ile Cys Gly Lys Thr Phe Gly His Ala Val Ser Leu Glu
        195                 200                 205

Gln His Thr His Val His Ser Gln Glu Arg Ser Phe Glu Cys Arg Met
    210                 215                 220

Cys Gly Lys Ala Phe Lys Arg Ser Ser Thr Leu Ser Thr His Leu Leu
225                 230                 235                 240

Ile His Ser Asp Thr Arg Pro Tyr Pro Cys Gln Phe Cys Gly Lys Arg
                245                 250                 255

Phe His Gln Lys Ser Asp Met Lys Lys His Thr Tyr Ile His Thr Gly
            260                 265                 270

Glu Lys Pro His Lys Cys Gln Val Cys Gly Lys Ala Phe Ser Gln Ser
        275                 280                 285

Ser Asn Leu Ile Thr His Ser Arg Lys His Thr Gly Phe Lys Pro Phe
    290                 295                 300

Ser Cys Glu Leu Cys Thr Lys Gly Phe Gln Arg Lys Val Asp Leu Arg
305                 310                 315                 320

Arg His Arg Glu Ser Gln His Asn Leu Lys
                325                 330

<210> SEQ ID NO 31
<211> LENGTH: 2303
<212> TYPE: DNA
<213> ORGANISM: Homo sapiens
<220> FEATURE:
<221> NAME/KEY: CDS
<222> LOCATION: (831)..(1514)

<400> SEQUENCE: 31
gaattcgtcc aaactgagga tcacaagtct ccacattctg gtaggagga tgagggtctg      60 agttaggatt tgggtcctgc agggcttgct aaggaatccc ctgatggcct aggattccac    120
gcagagcaca tctggtgtga gagagctcgc tgcaagggtg aaggctccgc cctatcagat    180
agacaaccag gccaccaaga ggcccagccc tccaaaccct ggatttgcaa catcctcaaa    240
gaacagcaac gggccttgag cagaattgag aaggaaatac ccccacctgc cctcagccgt    300
taagtgggct ttgctattca caagggcctc tgggtgtcct ggcagagagg ggagatggca    360
caggcaccag gtgctagggt gccagggcct cccgagaagg aacaggtgca aagcaggcaa    420
ttagcccaga aggtatccgt ggggcaggca gcctagatct gatggggaa gccaccagga    480 ttacatcatc tgctgtaaca actgctctga aaagaagata ttttttcaacc tgaacttgca    540 gtagctagtg gagaggcagg aaaaaggaaa tgaaaccaga gacagaggga agctgagcga    600
aaatagacct tcccgagaga ggaggaagcc cggagagaga cgcacggtcc cctccccgcc    660
cctaggccgc cgcccctct ctgccctcgg cggcgagcag cgcgccgcga cccgggccga    720
aggtgcgagg ggctccgggc ggccgggcgg gcgcacacca tccccgcggg cggcgcggag    780
```

```
ccggcgacag cgcgcgagag ggaccgggcg gtggcggcgg cgggaccggg atg gaa       836
                                                        Met Glu
                                                        1 ggg agc gcg gtg act gtc ctt gag cgc gga ggg gcg agc tcg ccg gcg      884
Gly Ser Ala Val Thr Val Leu Glu Arg Gly Gly Ala Ser Ser Pro Ala
          5                  10                  15 gag cgc cgg agc aag cgg agg cgc agg agc ggc ggc gac ggc ggc ggc      932
Glu Arg Arg Ser Lys Arg Arg Arg Arg Ser Gly Gly Asp Gly Gly Gly
         20                  25                  30 ggc ggc ggc gcc cga gca ccc gag ggg gtc cga gcc ccg gca gcc ggc      980
Gly Gly Gly Ala Arg Ala Pro Glu Gly Val Arg Ala Pro Ala Ala Gly
 35                  40                  45                  50 cag ccc cgc gcc aca aag gga gcg ccc ccg ccc ggc acc ccg cct         1028
Gln Pro Arg Ala Thr Lys Gly Ala Pro Pro Pro Gly Thr Pro Pro
                     55                  60                  65 ccc tcc cca atg tcc tcg gcc atc gaa agg aag agc ctg gac cct tca     1076
Pro Ser Pro Met Ser Ser Ala Ile Glu Arg Lys Ser Leu Asp Pro Ser
                 70                  75                  80 gag gaa cca gtg gat gag gtg ctg cag atc ccc cca tcc ctg ctg aca     1124
Glu Glu Pro Val Asp Glu Val Leu Gln Ile Pro Pro Ser Leu Leu Thr
             85                  90                  95 tgc ggc ggc tgc cag cag aac att ggg gac cgc tac ttc ctg aag gcc     1172
Cys Gly Gly Cys Gln Gln Asn Ile Gly Asp Arg Tyr Phe Leu Lys Ala
        100                 105                 110 atc gac cag tac tgg cac gag gac tgc ctg agc tgc gac ctc tgt ggc     1220
Ile Asp Gln Tyr Trp His Glu Asp Cys Leu Ser Cys Asp Leu Cys Gly
115                 120                 125                 130 tgc cgg ctg ggt gag gtg ggg cgg cgc ctc tac tac aaa ctg ggc cgg     1268
Cys Arg Leu Gly Glu Val Gly Arg Arg Leu Tyr Tyr Lys Leu Gly Arg
                135                 140                 145 aag ctc tgc cgg aga gac tat ctc agg ctt ttt ggg caa gac ggt ctc     1316
Lys Leu Cys Arg Arg Asp Tyr Leu Arg Leu Phe Gly Gln Asp Gly Leu
            150                 155                 160 tgc gca tcc tgt gac aag cgg att cgt gcc tat gag atg aca atg cgg     1364
Cys Ala Ser Cys Asp Lys Arg Ile Arg Ala Tyr Glu Met Thr Met Arg
        165                 170                 175 gtg aaa gac aaa gtg tat cac ctg gaa tgt ttc aaa tgc gcc gcc tgt     1412
Val Lys Asp Lys Val Tyr His Leu Glu Cys Phe Lys Cys Ala Ala Cys
    180                 185                 190 cag aag cat ttc tgt gta ggt gac aga tac ctc ctc atc aac tct gac     1460
Gln Lys His Phe Cys Val Gly Asp Arg Tyr Leu Leu Ile Asn Ser Asp
195                 200                 205                 210 ata gtg tgc gaa cag gac atc tac gag tgg act aag atc aat ggg atg     1508
Ile Val Cys Glu Gln Asp Ile Tyr Glu Trp Thr Lys Ile Asn Gly Met
                215                 220                 225 ata tag gcccgagtcc ccgggcatct ttggggaggt gttcactgaa gacgccgtct     1564
Ile ccatggcatc ttcgtcttca ctcttaggca ctttgggggt ttgagggtgg ggtaagggat   1624
ttcttagggg atggtagacc tttattgggt atcaagacat agcatccaag tggcataatt   1684
caggggctga cacttcaagg tgacagaagg accagcccct gagggagaac ttatggccac   1744
agcccatcca tagtaactga catgattagc agaagaaagg aacatttagg ggcaagcagg   1804
cgctgtgcta tcatgatgga atttcatatc tacagataga gagttgttgt gtacagactt   1864
gttgtgactt tgacgcttgc gaactagaga tgtgcaattg atttcttttc ttcctggctt   1924
tttaactccc ctgtttcaat cactgtcctc cacacaaggg aaggacagaa aggagagtgg   1984
ccattctttt tttcttggcc cccttcccaa ggccttaagc tttggaccca aggaaaactg   2044
```

```
catggagacg catttcggtt gagaatggaa accacaactt ttaaccaaac aattatttaa    2104
agcaatgctg atgaatcact gtttttagac accttcattt tgagggagg agttccacag    2164 attgtttcta tacaaatata aatcttaaaa agttgttcaa ctattttatt atcctagatt    2224
atatcaaagt atttgtcgtg tgtagaaaaa aaaacagctc tgcaggctta ataaaaatga    2284
cagactgaaa aaaaaaaaa                                                 2303
```

<210> SEQ ID NO 32
<211> LENGTH: 227
<212> TYPE: PRT
<213> ORGANISM: Homo sapiens

<400> SEQUENCE: 32

```
Met Glu Gly Ser Ala Val Thr Val Leu Glu Arg Gly Gly Ala Ser Ser
1               5                   10                  15

Pro Ala Glu Arg Arg Ser Lys Arg Arg Arg Ser Gly Gly Asp Gly
            20                  25                  30

Gly Gly Gly Gly Ala Arg Ala Pro Glu Gly Val Arg Ala Pro Ala
        35                  40                  45

Ala Gly Gln Pro Arg Ala Thr Lys Gly Ala Pro Pro Pro Gly Thr
    50                  55                  60

Pro Pro Pro Ser Pro Met Ser Ser Ala Ile Glu Arg Lys Ser Leu Asp
65                  70                  75                  80

Pro Ser Glu Glu Pro Val Asp Glu Val Leu Gln Ile Pro Pro Ser Leu
                85                  90                  95

Leu Thr Cys Gly Gly Cys Gln Gln Asn Ile Gly Asp Arg Tyr Phe Leu
                100                 105                 110

Lys Ala Ile Asp Gln Tyr Trp His Glu Asp Cys Leu Ser Cys Asp Leu
            115                 120                 125

Cys Gly Cys Arg Leu Gly Glu Val Gly Arg Arg Leu Tyr Tyr Lys Leu
        130                 135                 140

Gly Arg Lys Leu Cys Arg Arg Asp Tyr Leu Arg Leu Phe Gly Gln Asp
145                 150                 155                 160

Gly Leu Cys Ala Ser Cys Asp Lys Arg Ile Arg Ala Tyr Glu Met Thr
                165                 170                 175

Met Arg Val Lys Asp Lys Val Tyr His Leu Glu Cys Phe Lys Cys Ala
            180                 185                 190

Ala Cys Gln Lys His Phe Cys Val Gly Asp Arg Tyr Leu Leu Ile Asn
        195                 200                 205

Ser Asp Ile Val Cys Glu Gln Asp Ile Tyr Glu Trp Thr Lys Ile Asn
    210                 215                 220

Gly Met Ile
225
```

HEMATOPOIETIC PRECURSOR CELL PRODUCTION BY PROGRAMMING

PRIORITY CLAIM

This application is a national phase application under 35 U.S.C. §371 of International Application No. PCT/US2012/024098, filed Feb. 7, 2012, which claims priority to U.S. Application No. 61/440,619, filed Feb. 8, 2011, the entire contents of each of which are hereby incorporated by reference.

BACKGROUND OF THE INVENTION

1. Field of the Invention

The present invention relates generally to the field of molecular biology, stem cells, and differentiated cells. More particularly, it concerns programming of somatic cells and undifferentiated cells toward specific cell lineages, particularly hematopoietic cells and precursors of hematopoietic cells.

2. Description of Related Art

Hematopoietic cells or blood cells are in great demand for clinical applications and for laboratory use. In the clinic, hematopoietic stem cells (HSCs) can be used to reconstitute hematopoiesis in patients that have undergone a therapy that suppresses hematopoiesis, such as an anti-cancer therapy, or in patients that have inherited hematological diseases. In addition, red blood cells, platelets, and neutrophil granulocytes can be used in blood transfusions and in the treatment of certain hematological disorders. In the lab, blood cells can be used for many applications including drug screening.

Currently, blood cells for such clinical and laboratory applications are obtained from living donors. However, the limited supply of donor blood, especially when a genetically-compatible donor is required, limits therapeutic applications and drug screening. Thus, there remains a need to develop sources of blood cells other than donor blood. For example, there is a need for an unlimited supply of well-characterized functional blood cell types, including patient-specific HSCs for therapeutic applications.

SUMMARY OF THE INVENTION

The present invention overcomes a major deficiency in the art by providing hematopoietic cells and precursors of hematopoietic cells by programming, such as forward programming or transdifferentiation. For example, the methods disclosed herein may provide an unlimited supply of hematopoietic cells or precursors of hematopoietic cells. Such methods may be particularly useful in providing an unlimited supply of patient-specific hematopoietic precursors and hematopoietic cells.

Methods disclosed herein provide hematopoietic cells or hematopoietic precursor cells by programming a variety of cell types. In certain aspects, programming methods include culturing pluripotent stem cells or somatic cells under conditions that increase the expression level of one or more genes that, when expressed alone or in combination with other programming factor genes, are capable of promoting programming to the hematopoietic lineage. Such genes are termed "programming factor genes." Programming factor genes that promote programming to hematopoietic precursor cells are called hematopoietic precursor programming factor genes. Programming factor genes that promote programming to differentiated hematopoietic cells are called hematopoietic cell programming factor genes. Hematopoietic cell or hematopoietic precursor programming factor genes useful in the invention may include any genes that, alone or in combination, directly impose hematopoietic fate upon non-hematopoietic cells and may include transcription factor genes or other genes that are important in hematopoietic or endothelial cell differentiation or function.

The process of programming alters the type of progeny a cell can produce and includes the distinct processes of forward programming and transdifferentiation. In some embodiments, forward programming of multipotent cells or pluripotent cells provides hematopoietic cells or hematopoietic precursor cells. In other embodiments, transdifferentiation of non-hematopoietic somatic cells provides hematopoietic cells or hematopoietic precursor cells. In certain aspects, programming may comprise increasing the expression level of a sufficient number of hematopoietic precursor programming factor genes or hematopoietic cell programming factor genes to cause forward programming or transdifferentiation of non-hematopoietic cells to hematopoietic precursor cells or hematopoietic cells.

Sources of cells suitable for hematopoietic precursor or hematopoietic cell programming may include any stem cells or non-hematopoietic somatic cells. For example, the stem cells may be pluripotent stem cells or any non-pluripotent stem cells. As used herein, a "pluripotent cell" or "pluripotent stem cell" is a cell that has the capacity to differentiate into essentially any fetal or adult cell type. Exemplary types of pluripotent stem cells may include, but are not limited to, embryonic stem cells and induced pluripotent stem cells (or iPS cells). Such a pluripotent stem cell may be a mammalian pluripotent stem cell. In certain embodiments, the pluripotent stem cell is a human pluripotent stem cell. Sources of cells suitable for programming of hematopoietic precursors or hematopoietic cells by transdifferentiation may include any non-hematopoietic somatic cells. Such somatic cells may be any cells forming the body of an organism. In a particular aspect, the somatic cells may be immortalized to provide an unlimited supply of cells, for example, by increasing the level of telomerase reverse transcriptase (TERT). For example, the level of TERT can be increased by increasing the transcription of TERT from the endogenous gene, or by introducing a transgene through any gene delivery method or system.

Pluripotent stem cells useful in the invention may be induced pluripotent stem cells, embryonic stem cells, or pluripotent stem cells derived by nuclear transfer or cell fusion. The stem cells may also include multipotent stem cells, oligopotent stem cells, or unipotent stem cells. The stem cells may also include fetal stem cells or adult stem cells, such as hematopoietic stem cells, mesenchymal stem cells, neural stem cells, epithelial stem cells, or skin stem cells. In certain aspects, the stem cells may be isolated from umbilical tissue, placenta, amniotic fluid, chorion villi, blastocysts, bone marrow, adipose tissue, brain, peripheral blood, cord blood, menstrual blood, blood vessels, skeletal muscle, skin or liver.

A "progenitor cell" or "precursor cell" refers to a lineage-committed cell derived from a pluripotent stem cell. Thus, progenitor cells or precursor cells are more differentiated than pluripotent stem cells, but still have the capacity to differentiate into more than one type of cell. For example, hematopoietic precursor cells provided by methods disclosed herein may be able to differentiate into one or more of the three hematopoietic lineages—lymphoid, myeloid, or erythro-megakaryocytic. Hematopoietic cells provided by methods disclosed herein may be mature hematopoietic cells.

In certain embodiments, hematopoietic precursor cells are provided by forward programming of pluripotent stem cells or transdifferentiation of somatic cells. Such a method may comprise providing the hematopoietic precursor cells by culturing the pluripotent stem cells or somatic cells under conditions to increase the expression level of one or more hematopoietic precursor programming factor genes capable of causing forward programming of the pluripotent stem cells or transdifferentiation of the somatic cells into hematopoietic precursor cells, thereby forward programming the pluripotent stem cells or transdifferentiating the somatic cells into hematopoietic precursor cells.

As a skilled artisan would understand, methods for increasing the expression of the hematopoietic precursor and hematopoietic cell programming factor genes in the cells to be programmed may include any method known in the art, for example, by induction of expression of one or more expression cassettes previously introduced into the cells, or by introduction of nucleic acids such as DNA or RNA, polypeptides, or small molecules to the cells. Increasing the expression of certain endogenous but transcriptionally repressed programming factor genes may also comprise reversing the silencing or inhibitory effect on the expression of these programming factor genes by regulating the upstream transcription factor expression or epigenetic modulation.

In certain aspects, hematopoietic precursor cells are provided by forward programming of pluripotent stem cells. Such pluripotent stem cells may be induced pluripotent stem cells. In other aspects, hematopoietic precursor cells are provided by transdifferentiation of somatic cells. In some embodiments, the somatic cells are human somatic cells such as skin fibroblasts, adipose tissue-derived cells and human umbilical vein endothelial cells (HUVEC). Somatic cells useful for transdifferentiation may be immortalized somatic cells.

Hematopoietic precursor cells may be provided by forward programming of pluripotent stem cells or transdifferentiation of somatic cells that comprise at least one exogenous expression cassette. The expression cassette may comprise one or more hematopoietic precursor programming factor genes. In some aspects, pluripotent stem cells or somatic cells are contacted with one or more such hematopoietic precursor programming factors comprising gene products of the one or more hematopoietic precursor programming factor genes in an amount sufficient to cause forward programming of the pluripotent cells or transdifferentiation of the somatic cells into hematopoietic precursor cells. In some embodiments, the one or more gene products are polypeptide products of one or more hematopoietic precursor programming factor genes. In certain aspects, the one or more hematopoietic precursor programming factors include a protein transduction domain to facilitate intracellular entry of polypeptides of the hematopoietic precursor programming factor genes. Such protein transduction domains are well known in the art, such as an HIV TAT protein transduction domain, HSV VP22 protein transduction domain, *Drosophila* Antennapedia homeodomain, or variants thereof. In other embodiments, the one or more gene products are RNA transcripts of one or more hematopoietic precursor programming factor genes.

Hematopoietic precursor or hematopoietic cell programming factor genes useful in the invention may include any of the genes listed in Table I. One, two, three, four, five, six, seven, eight, nine, ten, or more of the provided hematopoietic precursor or hematopoietic cell programming factor genes may be used for forward programming or transdifferentiation.

In some embodiments, at least one hematopoietic precursor programming factor gene is an endothelial differentiation factor. Examples of useful endothelial differentiation factors include but are not limited to ERG (v-ets erythroblastosis virus E26 oncogene homolog (avian)), FLI-1 (Friend leukemia virus integration 1), or ETV2 (ets variant 2), or any isoform or variant thereof. In particular aspects, at least one endothelial differentiation factor gene is ERG, meaning that the endothelial differentiation factor gene may be any isoform or variant of ERG. In even more particular aspects, the ERG that is used is ERG-3 (ERG isoform 3) or ERG-2 (ERG isoform 2).

In other aspects, at least one hematopoietic precursor programming factor gene is GFI1 (growth factor independent 1 transcription repressor), GFI1B (growth factor independent 1B transcription repressor), TAL1 (T-cell acute lymphocytic leukemia), LYL1 (lymphoblastic leukemia derived sequence 1), LMO2 (LIM domain only 2 (rhombotin-like 1)), GATA2 (GATA binding protein 2), GATA3 (GATA binding protein 3), or SPI1 (spleen focus forming virus (SFFP) proviral integration oncogene spi1), or any isoform or variant thereof.

In certain aspects, the pluripotent stem cells or somatic cells are cultured under conditions to increase the expression level of two or more hematopoietic precursor programming factor genes capable of causing forward programming of the pluripotent stem cells or transdifferentiation of the somatic cells into hematopoietic precursor cells, thereby forward programming the pluripotent stem cells or transdifferentiating the somatic cells into hematopoietic precursor cells. In certain aspects, the at least two or more hematopoietic precursor programming factor genes include ERG, GFI1, GATA2, SPI1, TAL1, or LMO2. In other aspects, one of the hematopoietic precursor programming factor genes may be an endothelial differentiation factor, which may be, for example, ERG, FLI-1, or ETV2. The second such hematopoietic precursor programming factor gene may be GFI1, GFI1B, TAL1, LYL1, LMO2, GATA2, GATA3, or SPI1. In some embodiments, the at least two or more hematopoietic precursor programming factor genes include ERG and GFI1. For example, the at least two or more hematopoietic precursor programming factor genes may include ERG (e.g., ERG-3) and GFI1. In other embodiments, the at least two or more hematopoietic precursor programming factor genes include ERG and GATA2. For example, the at least two or more hematopoietic precursor programming factor genes may include ERG (e.g., ERG-3) and GATA2. In yet other embodiments, the at least two or more hematopoietic precursor programming factor genes include ERG, GATA2, and SPI1. For example, the at least two or more hematopoietic precursor programming factor genes may include ERG (e.g., ERG-3), GATA2, and SPI1.

Exogenous expression cassettes for use in forward programming or transdifferentiation may include one or more externally inducible transcriptional regulatory elements for inducible expression of the one or more hematopoietic precursor programming factor genes. For example, an exogenous expression cassette useful in the invention may contain an inducible promoter, such as a promoter that includes a tetracycline response element. In some aspects, the exogenous expression cassette is comprised in a gene delivery system. Many gene delivery systems are known to those of ordinary skill in the art, and non-limiting examples of useful gene delivery systems include a transposon system, a viral gene delivery system, an episomal gene delivery system, an mRNA delivery system, or a protein delivery system. A viral gene delivery system useful in the invention may be an RNA-based or DNA-based viral vector. An episomal gene delivery system useful in the invention may be a plasmid, an Epstein-Barr virus (EBV)-based episomal vector, a yeast-based vector, an adenovirus-based vector, a simian virus 40 (SV40)-based episomal vector, a bovine papilloma virus (BPV)-based vector, or the like. In certain aspects, an expression cassette for use in forward programming or transdifferentiation may include a hematopoietic precursor-specific transcriptional regulatory element operably linked to a reporter gene.

In some embodiments, the hematopoietic precursor cells derived by methods disclosed herein have one or more characteristics of hematopoietic precursor cells. Such characteristics of hematopoietic precursor cells may include one or more of the following: (i) expression of one or more hematopoietic precursor markers; (ii) lack of expression of one or more pluripotent stem cell markers or somatic cells markers; (iii) one or more hematopoietic precursor functional features; (iv) and one or more hematopoietic precursor morphological features. The one or more hematopoietic precursor markers of (i) may include any marker of hematopoietic precursor cells known in the art. Non-limiting examples of hematopoietic precursor markers include CD43, CD33, CD34, CD45, CD235a, CD41a, CD38, and CD74. In particular aspects, the one or more hematopoietic precursor markers include CD43, CD45, and/or CD34. The one or more pluripotent stem cell markers or somatic cell markers of (ii) may include any marker of pluripotent stem cells or somatic cells known in the art. Non-limiting examples of pluripotent stem cell markers or somatic cell markers include TRA-1-60, TRA-1-81, CD166, and CD140b. The one or more hematopoietic precursor functional features of (iii) may include the ability to differentiate into two or more cell types selected from the group consisting of plasma cell, natural killer cell, macrophage, mast cell, megakaryocyte, erythrocyte, granulocyte, lymphocyte, monocyte, leukocyte, and thrombocyte. In certain aspects, the one or more hematopoietic precursor functional features includes the ability to differentiate into cells of the myeloid lineage, lymphoid lineage, or erythro-megakaryocytic lineage. In yet other certain aspects, the one or more hematopoietic precursor functional features includes the ability to differentiate into cells of the lymphoid, myeloid, and erythro-megakaryocytic lineages. The one or more hematopoietic precursor morphological features of (iv) may include any known morphological feature characteristic of hematopoietic precursor cells in nature. For example, hematopoietic precursor cells typically appear as cell clusters producing round non-adherent cells.

Methods of providing hematopoietic precursor cells may further include selecting or enriching for hematopoietic precursor cells, wherein the selected or enriched hematopoietic precursor cells comprise one or more of the characteristics of hematopoietic precursor cells described herein. In other embodiments, the selected or enriched hematopoietic precursor cells may express a reporter gene that is operably linked to a hematopoietic precursor cell specific transcriptional regulatory element.

Pluripotent stem cells or somatic cells used for forward programming or transdifferentiation may be cultured in a medium comprising one or more growth factors. Such growth factors may include, but are not limited to, fibroblast growth factor (FGF), vascular endothelial growth factor (VEGF), stem cell factor (SCF), thrombopoietin (TPO), FLT-3-Ligand (FLT3L), interleukin-3 (IL-3), interleukin-6 (IL-6), granulocyte colony-stimulating factor (G-CSF), or interleukin-9 (IL-9). In certain aspects, the pluripotent stem cells, somatic cells, or progeny of the pluripotent stem cells or somatic cells are cultured in a medium comprising SCF, TPO, FLT3L, IL-3, and IL-6.

Hematopoietic precursor cells provided by methods disclosed herein may be provided at least, about, or up to 3, 4, 5, 6, 7, 8, 9, 10, 11, 12, 13, 14, 15, 16, 17, 18, 19, 20 days (or any range derivable therein) after the increased expression of programming factor genes or culturing in the presence or absence of growth factors. In some embodiments, the provided hematopoietic precursor cells are obtained after up to ten days of the increased expression of the one or more hematopoietic precursor programming factor genes. In other embodiments, the provided hematopoietic precursor cells are obtained after up to six days of the increased expression. In yet other embodiments, the provided hematopoietic precursor cells are obtained after up to four days of the increased expression.

In certain aspects, methods of providing hematopoietic precursor cells or hematopoietic cells include one or more additional steps wherein cell groupings are dispersed into essentially individual cells. The dispersing may be performed, for example, at least about 24 hours after the increased expression of programming factor genes. In some embodiments, the dispersing is performed at least 1, 2, 3, 4, or more days after the increased expression. Dispersing of cell groupings may be performed by mechanical or enzymatic means. For example, the cells may be dispersed by treatment with an effective amount of one or more enzymes, such as trypsin or trypLE, or a mixture of enzymes such as Accutase®. The methods may also include one or more steps wherein the essentially individual cells are dispersed onto a surface coated with a matrix component. For example, the surface may be coated with fibronectin, collagen, poly-d-lysine, matrigel, or an RGD peptide.

Also disclosed are methods of providing erythro-megakaryocytic (EMk) precursor cells by forward programming of pluripotent stem cells or transdifferentiation of somatic cells, comprising: providing the EMk precursor cells by culturing the pluripotent stem cells or somatic cells under conditions to increase the expression level of one or more EMk precursor programming factor genes capable of causing forward programming of the pluripotent cells or transdifferentiation of the somatic cells into EMk precursor cells, thereby forward programming the pluripotent stem cells or transdifferentiating the somatic cells into EMk precursor cells. In some aspects, the pluripotent stem cells or somatic cells include at least one exogenous expression cassette, and the expression cassette comprises one or more EMk precursor programming factor genes.

In some embodiments, the at least one EMk precursor programming factor gene may, for example, include GATA2, TAL1, LMO2, or ERG. In certain aspects, the pluripotent stem cells or somatic cells are cultured under conditions to increase the expression level of two or more EMk precursor programming factor genes capable of causing forward programming of the pluripotent stem cells or transdifferentiation of the somatic cells into EMk precursor cells, thereby forward programming the pluripotent stem cells or transdifferentiating the somatic cells into EMk precursor cells. The two or more EMk precursor programming factor genes may, for example, include ERG, GATA2, TAL1, or LMO2. In certain embodiments, the two or more EMk precursor programming factor genes are ERG, GATA2, and TAL1. In other certain embodiments, the two or more EMk precursor programming factor genes are ERG, GATA2, and LMO2. In yet other aspects, the two or more EMk precursor programming factor genes are ERG, GATA2, TAL1, and LMO2. EMk precursor cells provided by methods disclosed herein may have the ability to differentiate into erythroid or megakaryocytic cells.

Hematopoietic precursor cells, hematopoietic cells, or EMk precursor cells may be provided by using one or more of the nucleic acid or polypeptide sequences that are disclosed or described herein. In certain aspects, the nucleic acid or polypeptide is 50, 55, 60, 65, 70, 75, 80, 81, 82, 83, 84, 85, 86, 87, 88, 89, 90, 91, 92, 93, 94, 95, 96, 97, 98, 99, or 100%, or any range derivable therein, identical to or homologous with any sequence disclosed or described herein, including those sequences that are described by identifying their database accession numbers.

Hematopoietic precursor cells, hematopoietic cells, or EMk precursor cells provided herein may be used in any methods and applications currently known in the art for such cells, including clinical or screening applications. For example, disclosed herein are methods of assessing a compound for an effect on a hematopoietic precursor cell or an EMk precursor cell. In certain embodiments, the method includes (a) contacting the hematopoietic precursor provided by a method disclosed herein with the compound; and (b) assaying an effect of the compound on the hematopoietic precursor. The effect of the compound on the hematopoietic precursor may be, for example, a pharmacological or toxicological effect.

Also provided are methods for treating a subject. For example, the subject may have or be at risk of developing a hematological disorder. The hematological disorder may be any such disorder known in the art including, for example, a hemoglobinopathy or anemia. In some embodiments, the subject has or is at risk of developing a disease characterized by decreased numbers of hematopoietic cells (such as, for example, myelodysplastic syndrome, myelofibrosis, neutropenia, agranulocytosis, Glanzmann's thrombasthenia, thrombocytopenia, and acquired immune deficiency syndrome). In particular aspects, the method comprises administering to the subject a therapeutically effective amount of hematopoietic precursor cells obtained by a method disclosed herein.

In some aspects, a method for treating a subject having a neoplastic disease is provided. A neoplastic disease includes any disease marked by an abnormal mass of tissue, typically having a growth that exceeds and is uncoordinated with that of normal tissue. A neoplastic growth may occur in, for example, the lung, skin, muscle, liver, kidney, colon, prostate, breast, brain, bladder, small intestine, large intestine, cervix, stomach, pancreas, testes, ovaries, bone, marrow, or spine. In certain embodiments, the neoplastic disease is a cancer. The method for treating a subject having a neoplastic disease may include administering to the subject a therapeutically effective amount of hematopoietic precursor cells obtained by a method disclosed herein. In certain aspects, the subject having the neoplastic disease has received a therapy that suppresses hematopoiesis. For example, the subject may have undergone or is likely to undergo chemotherapy, radiation therapy, or administration of an immunosuppressant drug.

Methods for treating a subject in need of hematopoietic cells or blood cells are also provided. Such a method may include administering to the subject a therapeutically effective amount of hematopoietic precursor cells obtained by a method disclosed herein. In certain aspects, the subject is a subject that is in need of a blood transfusion. For example, the subject may have suffered an injury or has a disorder marked by a deficiency in hematopoietic cells or blood cells. In certain aspects, the subject has or is at risk of developing anemia, hemolytic anemia, or any other hematological disorder.

Also provided are methods for treating a subject in need of erythroid and/or megakaryocytic cells. Such a method may comprise administering to the subject a therapeutically effective amount of EMk precursor cells obtained by a method disclosed herein. These methods may be employed on any subject in need of EMk precursor cells including, but not limited to, a subject in need of erythrocytes, a subject in need of a blood transfusion, a subject having or at risk of developing anemia or hemolytic anemia, a subject in need of megakaryocytic cells or megakaryocytes (e.g., a subject having or at risk of developing megakaryocytopenia), a subject in need of thrombocytes, or a subject that has suffered a tissue injury or is likely to suffer a tissue injury.

In certain aspects, hematopoietic precursor cells are provided that have been produced by a process in accordance with any of the methods disclosed herein for producing such cells. In other aspects, EMk precursor cells are provided that have been produced by a process in accordance with any of the methods disclosed herein for producing such cells.

In certain embodiments, a cell populations is provided. Such a cell population may comprise hematopoietic precursor cells, hematopoietic cells, or EMk precursor cells. The population may also include stem cells or progeny of stem cells, hematopoietic precursor cells, hematopoietic cells, or EMk precursor cells. For example, the cell population may consist of hematopoietic precursor cells, wherein at least 1, 5, 10, 15, 20, 25, 30, 35, 40, 45, 50, 60, 70, 80, 90, 99% of the hematopoietic precursor cells, or any range derivable therein, carry an exogenous expression cassette that includes one or more hematopoietic precursor programming factor genes. In some aspects, the provided cell population includes hematopoietic precursor cells, and at least 80% of the hematopoietic precursor cells include an exogenous expression cassette that comprises one or more hematopoietic precursor programming factor genes. In other aspects, the cell population may consist of EMk precursor cells, wherein at least 1, 5, 10, 15, 20, 25, 30, 35, 40, 45, 50, 60, 70, 80, 90, 99% of the EMk precursor cells, or any range derivable therein, carry an exogenous expression cassette that includes one or more EMk precursor programming factor genes. For example, the provided cell population may include EMk precursor cells, and at least 80% of the EMk precursor cells include an exogenous expression cassette that comprises one or more EMk precursor programming factor genes.

Embodiments discussed in the context of methods and/or compositions of the invention may be employed with respect to any other method or composition described herein. Thus, an embodiment pertaining to one method or composition may be applied to other methods and compositions of the invention as well.

As used herein the terms "encode" or "encoding" with reference to a nucleic acid are used to make the invention readily understandable by the skilled artisan; however, these terms may be used interchangeably with "comprise" or "comprising" respectively.

As used herein the specification, "a" or "an" may mean one or more. As used herein in the claim(s), when used in conjunction with the word "comprising," the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the team "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Any embodiment of any of the present methods and compositions may consist of or consist essentially of— rather than comprise/include/contain/have—the described features and/or steps. Thus, in any of the claims, the term "consisting of" or "consisting essentially of" may be substituted for any of the open-ended linking verbs recited above, in order to change the scope of a given claim from what it would otherwise be using the open-ended linking verb.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 4A. A two-vector PiggyBac transposon gene expression system. Ptight is an rtTET-responsive inducible promoter; pEF is the eukaryotic elongation factor 1α promoter; hPBase is the coding region for the PiggyBac transposase with codons optimized for expression in human cells. FIG. 4B. EGFP induction in human ESC inducible lines. Images are shown of human ESC inducible lines after 2 days induction with or without Doxycycline (1 µg/ml). FIG. 4C. Flow cytometric analysis of EGFP expression in human ESC inducible lines after 4 days induction with or without Doxycycline (1 µg/ml). Gray lines are human ESC inducible lines without transfection of the EGFP vector; black lines are human ESC Rd lines with stable PiggyBac transposon integration after 4 days induction with or without Doxycycline.

FIGS. 5A, 5B, 5C. Forward programming of multipotent hematopoietic precursors from human ESCs/iPSCs through ERG and GATA2 expression. FIG. 5A. Percentages of erythro-megakaryocytic (EMk; D43+CD235a+CD41a+) and multipotent lineage negative (Lin–) CD43+CD45–/+ precursors and absolute numbers of colony-forming cells (CFCs) in cultures transfected with the indicated gene combinations. FIG. 5B. Bright-field images of human ESCs transfected with the indicated gene combinations. FIG. 5C. Flow cytometric analysis of human ESC cultures transfected with the indicated gene combinations after 6 days of Doxycycline induction.

FIG. 6A. The percentages of EMk (CD43+CD235a+CD41a+) and multipotent lineage negative (Lin–) CD43+CD45–/+ precursors, and absolute numbers of colony-forming cells (CFCs) in cultures transfected with indicated gene combinations. FIG. 6B. Bright-field images of human ESCs transfected with ERG and GFI1. FIG. 6C. Flow cytometric analysis of ERG/GFI1-transfected human ESC cultures after 6 days of Doxycycline induction.

DESCRIPTION OF ILLUSTRATIVE EMBODIMENTS

Figure 1:
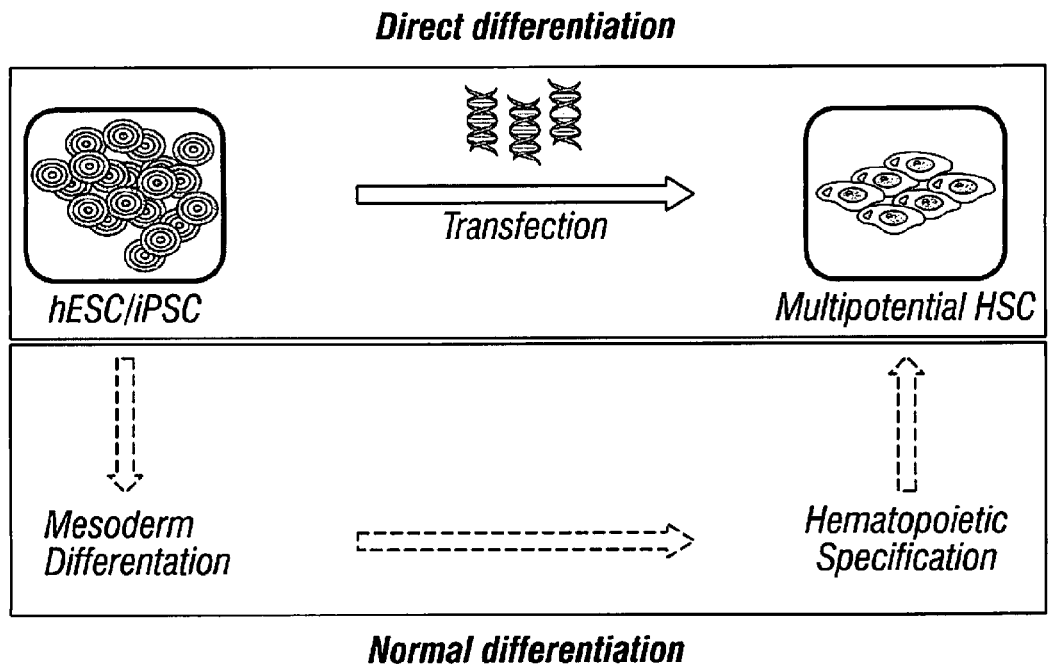
FIG. 1. Alternative approaches for differentiation of hematopoietic precursor cells (also called multipotential hematopoietic stem cells) from human ESCs/iPSCs.

Human embryonic stem cells (ESCs) and induced pluripotent stem cells (iPSCs) are capable of unlimited proliferation in vitro, while retaining the potential to differentiate into all somatic cell types. Human ESCs and iPSCs, therefore, could potentially provide an unlimited supply of patient-specific functional blood cells for laboratory use (e.g., drug development) or clinical use (e.g., therapeutic use). Somatic cells, such as immortalized somatic cell lines, could also potentially provide such an unlimited supply of blood cells and hematopoietic precursor cells. The inventors have identified a strategy for promoting forward programming of human ESCs/iPSCs or somatic cells to cells of hematopoietic lineages in vitro. The strategy bypasses the normal in vivo development including the stages of mesoderm induction and specification of multipotent hematopoietic precursors (see FIG. 1).

I. DEFINITIONS

"Programming" is a process that alters the type of progeny a cell can produce. For example, a cell has been programmed when it has been altered so that it can form progeny of at least one new cell type, either in culture or in vivo, as compared to what it would have been able to form under the same conditions without programming. This means that after sufficient proliferation, a measurable proportion of progeny having phenotypic characteristics of the new cell type are observed, if essentially no such progeny could form before programming; alternatively, the proportion having characteristics of the new cell type is measurably more than before programming. This process includes differentiation, dedifferentiation and transdifferentiation. "Differentiation" is the process by which a less specialized cell becomes a more specialized cell type. "Dedifferentiation" is a cellular process in which a partially or terminally differentiated cell reverts to an earlier developmental stage, such as pluripotency or multipotency. "Transdifferentiation" is a process of transforming one differentiated cell type into another differentiated cell type. Typically, transdifferentiation by programming occurs without the cells passing through an intermediate pluripotency stage—i.e., the cells are programmed directly from one differentiated cell type to another differentiated cell type. Under certain conditions, the proportion of progeny with characteristics of the new cell type may be at least about 1%, 5%, 25% or more in order of increasing preference.

The term "hematopoietic precursor programming factor gene" is a gene that, when expressed alone or in combination with another programming factor gene, is capable of causing direct differentiation of pluripotent cells or non-hematopoietic somatic cells into hematopoietic precursor cells. The term "hematopoietic cell programming factor gene" is a gene that, when expressed alone or in combination with another programming factor gene, is capable of causing direct differentiation of pluripotent cells or non-hematopoietic somatic cells into differentiated hematopoietic cells.

The term "forward programming" refers to the programming of a multipotent or pluripotent cell, as opposed to a differentiated somatic cell that has no pluripotency, by the provision of one or more specific lineage-determining genes or gene products to the multipotent or pluripotent cell. For example, forward programming may describe the process of programming ESCs or iPSCs to hematopoietic precursor cells or other precursor cells, or to hematopoietic cells or other differentiated somatic cells.

The term "exogenous," when used in relation to a protein, gene, nucleic acid, or polynucleotide in a cell or organism refers to a protein, gene, nucleic acid, or polynucleotide that has been introduced into the cell or organism by artificial or natural means; or in relation to a cell, the term refers to a cell that was isolated and subsequently introduced to other cells or to an organism by artificial or natural means. An exogenous nucleic acid may be from a different organism or cell, or it may be one or more additional copies of a nucleic acid that occurs naturally within the organism or cell. An exogenous cell may be from a different organism, or it may be from the same organism. By way of a non-limiting example, an exogenous nucleic acid is one that is in a chromosomal location different from where it would be in natural cells, or is otherwise flanked by a different nucleic acid sequence than that found in nature.

By "expression construct" or "expression cassette" is meant a nucleic acid molecule that is capable of directing transcription. An expression construct includes, at a minimum, one or more transcriptional control elements (such as promoters, enhancers or a structure functionally equivalent thereof) that direct gene expression in one or more desired cell types, tissues or organs. Additional elements, such as a transcription termination signal, may also be included.

A "vector" or "construct" (sometimes referred to as a gene delivery system or gene transfer "vehicle") refers to a macromolecule or complex of molecules comprising a polynucleotide to be delivered to a host cell, either in vitro or in vivo.

A "plasmid," a common type of a vector, is an extra-chromosomal DNA molecule separate from the chromosomal DNA that is capable of replicating independently of the chromosomal DNA. In certain cases, it is circular and double-stranded.

An "origin of replication" ("ori") or "replication origin" is a DNA sequence, e.g., in a lymphotrophic herpes virus, that when present in a plasmid in a cell is capable of maintaining linked sequences in the plasmid and/or a site at or near where DNA synthesis initiates. As an example, an on for EBV includes FR sequences (20 imperfect copies of a 30 bp repeat), and preferably DS sequences; however, other sites in EBV bind EBNA-1, e.g., Rep* sequences can substitute for DS as an origin of replication (Kirshmaier and Sugden, 1998). Thus, a replication origin of EBV includes FR, DS or Rep* sequences or any functionally equivalent sequences through nucleic acid modifications or synthetic combination derived therefrom. For example, the present invention may also use genetically engineered replication origin of EBV, such as by insertion or mutation of individual elements, as specifically described in Lindner, et. al., 2008.

The term "corresponds to" is used herein to mean that a polynucleotide sequence is homologous (i.e., is identical, not strictly evolutionarily related) to all or a portion of a reference polynucleotide sequence, or that a polypeptide sequence is identical to a reference polypeptide sequence. In contradistinction, the term "complementary to" is used herein to mean that the complementary sequence is homologous to all or a portion of a reference polynucleotide sequence. For illustration, the nucleotide sequence "TATAC" corresponds to a reference sequence "TATAC" and is complementary to a reference sequence "GTATA."

A "gene," "polynucleotide," "coding region," "sequence," "segment," "fragment," or "transgene" that "encodes" a particular protein, is a nucleic acid molecule that is transcribed and optionally also translated into a gene product, e.g., a polypeptide, in vitro or in vivo when placed under the control of appropriate regulatory sequences. The coding region may be present in either a cDNA, genomic DNA, or RNA form. When present in a DNA form, the nucleic acid molecule may be single-stranded (i.e., the sense strand) or double-stranded. The boundaries of a coding region are determined by a start codon at the 5' (amino) terminus and a translation stop codon at the 3' (carboxy) terminus. A gene can include, but is not limited to, cDNA from prokaryotic or eukaryotic mRNA, genomic DNA sequences from prokaryotic or eukaryotic DNA, and synthetic DNA sequences. A transcription termination sequence will usually be located 3' to the gene sequence.

The term "control elements" refers collectively to promoter regions, polyadenylation signals, transcription termination sequences, upstream regulatory domains, origins of replication, internal ribosome entry sites (IRES), enhancers, splice junctions, and the like, which collectively provide for the replication, transcription, post-transcriptional processing, and translation of a coding sequence in a recipient cell. Not all of these control elements need be present so long as the selected coding sequence is capable of being replicated, transcribed, and translated in an appropriate host cell.

The term "promoter" is used herein in its ordinary sense to refer to a nucleotide region comprising a DNA regulatory sequence, wherein the regulatory sequence is derived from a gene that is capable of binding RNA polymerase and initiating transcription of a downstream (3' direction) coding sequence.

By "enhancer" is meant a nucleic acid sequence that, when positioned proximate to a promoter, confers increased transcription activity relative to the transcription activity resulting from the promoter in the absence of the enhancer domain.

By "operably linked" with reference to nucleic acid molecules is meant that two or more nucleic acid molecules (e.g., a nucleic acid molecule to be transcribed, a promoter, and an enhancer element) are connected in such a way as to permit transcription of the nucleic acid molecule. "Operably linked" with reference to peptide and/or polypeptide molecules means that two or more peptide and/or polypeptide molecules are connected in such a way as to yield a single polypeptide chain, i.e., a fusion polypeptide, having at least one property of each peptide and/or polypeptide component of the fusion. The fusion polypeptide is preferably chimeric, i.e., composed of heterologous molecules.

"Homology" refers to the percent of identity between two polynucleotides or two polypeptides. The correspondence between one sequence and another can be determined by techniques known in the art. For example, homology can be determined by a direct comparison of the sequence information between two polypeptide molecules by aligning the sequence information and using readily available computer programs. Alternatively, homology can be determined by hybridization of polynucleotides under conditions that promote the formation of stable duplexes between homologous regions, followed by digestion with single strand-specific nuclease(s), and size determination of the digested fragments. Two DNA, or two polypeptide, sequences are "substantially homologous" to each other when at least about 80%, preferably at least about 90%, and most preferably at least about 95% of the nucleotides, or amino acids, respectively match over a defined length of the molecules, as determined using the methods above.

The term "cell" is herein used in its broadest sense in the art and refers to a living body that is a structural unit of tissue of a multicellular organism, is surrounded by a membrane structure that isolates it from the outside, has the capability of self-replicating, and has genetic information and a mechanism for expressing it. Cells used herein may be naturally-occurring cells or artificially modified cells (e.g., fusion cells, genetically modified cells, etc.).

As used herein, the terms "stem cell" or "multipotent cell" refer to a cell capable of giving rising to at least one type of a more specialized cell. A stem cells has the ability to self-renew, i.e., to go through numerous cycles of cell division while maintaining the undifferentiated state, and has potency, i.e., the capacity to differentiate into specialized cell types. Typically, stem cells can regenerate an injured tissue. Stem cells herein may be, but are not limited to, embryonic stem (ES) cells, induced pluripotent stem cells, or tissue stem cells (also called tissue-specific stem cells, or somatic stem cells). Any artificially produced cell having the above-described abilities (e.g., fusion cells, reprogrammed cells, or the like used herein) may be a stem cell.

"Embryonic stem (ES) cells" are pluripotent stem cells derived from early embryos. An ES cell was first established in 1981, which has also been applied to production of knockout mice since 1989. In 1998, a human ES cell was established, which is currently becoming available for regenerative medicine.

Unlike ES cells, tissue stem cells have a limited differentiation potential. Tissue stem cells are present at particular locations in tissues and have an undifferentiated intracellular structure. Therefore, the pluripotency of tissue stem cells is typically low. Tissue stem cells have a higher nucleus/cytoplasm ratio and have few intracellular organelles. Most tissue stem cells have low pluripotency, a long cell cycle, and proliferative ability beyond the life of the individual. Tissue stem cells are separated into categories, based on the sites from which the cells are derived, such as the dermal system, the digestive system, the bone marrow system, the nervous system, and the like. Tissue stem cells in the dermal system include epidermal stem cells, hair follicle stem cells, and the like. Tissue stem cells in the digestive system include pancreatic (common) stem cells, liver stem cells, and the like. Tissue stem cells in the bone marrow system include hematopoietic stem cells, mesenchymal stem cells, and the like. Tissue stem cells in the nervous system include neural stem cells, retinal stem cells, and the like.

"Induced pluripotent stem cells," commonly abbreviated as iPS cells or iPSCs, refer to a type of pluripotent stem cell artificially prepared from a non-pluripotent cell, typically an adult somatic cell, or terminally differentiated cell, such as a fibroblast, a hematopoietic cell, a myocyte, a neuron, an epidermal cell, or the like, by inserting certain genes, referred to as reprogramming factors.

"Pluripotency" refers to a stem cell that has the potential to differentiate into all cells constituting one or more tissues or organs, or preferably, any of the three germ layers: endoderm (interior stomach lining, gastrointestinal tract, the lungs), mesoderm (muscle, bone, blood, urogenital), or ectoderm (epidermal tissues and nervous system). The term "pluripotent stem cells" used herein refers to cells that can differentiate into essentially any fetal or adult cell type such as cells derived from any of the three germ layers, for example, direct descendants of totipotent cells or induced pluripotent cells.

As used herein "totipotent stem cells" refers to cells having the ability to differentiate into all cells constituting an organism, such as cells that are produced from the fusion of an egg and sperm cell. Cells produced by the first few divisions of the fertilized egg are also totipotent. These cells can differentiate into embryonic and extraembryonic cell types. Pluripotent stem cells can give rise to any fetal or adult cell type. However, alone they cannot develop into a fetal or adult animal because they lack the potential to contribute to extraembryonic tissue, such as the placenta.

In contrast, progenitor cells (also referred to herein as precursor cells) are multipotent stem cells, i.e., they are capable of differentiating into a limited number of cell fates. A "progenitor cell" or "precursor cell" refers to a lineage-committed cell derived from a pluripotent stem cell. Thus, progenitor cells are more differentiated than pluripotent stem cells, but still have the capacity to differentiate into more than one type of cell. Multipotent progenitor cells can give rise to more than one other cell type, but those types are limited in number. An example of a multipotent stem cell is a hematopoietic stem cell—a blood stem cell that can develop into several types of blood cells, but cannot develop into brain cells or certain other types of cells. At the end of the long series of cell divisions that form the embryo are cells that are terminally differentiated, or that are considered to be permanently committed to a specific function. An example of a type of precursor cell is a hematopoietic precursor cell that may be provided by methods disclosed herein and may be able to differentiate into one or more of the three hematopoietic lineages—lymphoid, myeloid, or erythro-megakaryocytic.

As used herein, the term "somatic cell" refers to any cell other than a germ cell, such as an egg, a sperm, or the like, that does not directly transfer its DNA to the next generation. Typically, somatic cells have limited or no pluripotency. Somatic cells used herein may be naturally-occurring or genetically modified.

Cells are "substantially free" of certain undesired cell types, as used herein, when they have less that 10% of the undesired cell types, and are "essentially free" of certain cell types when they have less than 1% of the undesired cell types. However, even more desirable are cell populations wherein less than 0.5% or less than 0.1% of the total cell population comprise the undesired cell types. Thus, cell populations wherein less than 0.1% to 1% (including all intermediate percentages) of the cells of the population comprise undesirable cell types are essentially free of these cell types. A medium is "essentially free" of certain reagents, as used herein, when there is no external addition of such agents. More preferably, these agents are absent or present at an undetectable amount.

II. CELLS INVOLVED IN HEMATOPOIETIC CELL PROGRAMMING

In certain embodiments of the invention, there are disclosed methods and compositions for providing hematopoietic cells or precursors of hematopoietic cells by forward programming of pluripotent cells that are not hematopoietic cells, or by transdifferentiation of somatic cells that are not hematopoietic cells. Also provided are cells that comprise exogenous expression cassettes including one or more hematopoietic precursor programming factor genes and/or reporter expression cassettes specific for hematopoietic cell or hematopoietic precursor cell identification. In some embodiments, the cells may be stem cells, including but not limited to, embryonic stem cells, fetal stem cells, or adult stem cells. In further embodiments, the cells may be any somatic cells.

A. Stem Cells

Stem cells are cells found in most, if not all, multi-cellular organisms. They are characterized by the ability to renew themselves through mitotic cell division and the ability to differentiate into a diverse range of specialized cell types. The two broad types of mammalian stem cells are: embryonic stem cells that are found in blastocysts, and adult stem cells that are found in adult tissues. In a developing embryo, stem cells can differentiate into all of the specialized embryonic tissues. In adult organisms, stem cells and progenitor cells act as a repair system for the body, replenishing specialized cells, and also maintain the normal turnover of regenerative organs, such as blood, skin or intestinal tissues.

Human embryonic stem cells (ESCs) and induced pluripotent stem cells (iPSCs) are capable of long-term proliferation in vitro, while retaining the potential to differentiate into all cell types of the body, including hematopoietic cells and hematopoietic precursor cells. Thus these cells could potentially provide an unlimited supply of patient-specific functional hematopoietic cells and hematopoietic precursor cells for both drug development and therapeutic uses. The differentiation of human ESCs/iPSCs to hematopoietic cells and hematopoietic precursor cells in vitro recapitulates normal in vivo development; i.e. they undergo the normal sequential developmental stages including mesoderm differentiation and hematopoietic specification (FIG. 1). That sequential developmental process requires the addition of different growth factors at different stages of differentiation. Certain aspects of the invention provide fully functional hematopoietic precursor cells by forward programming from human ESCs/iPSCs or transdifferentiation from somatic cells via expression of a combination of transcription factors important for hematopoietic cell differentiation/function, similar to the generation of iPSCs, bypassing most—if not all—normal developmental stages (FIG. 1). This approach may be more time- and cost-efficient, and generate hematopoietic precursor cells and hematopoietic cells with functions highly similar, if not identical, to human adult hematopoietic cells and precursors of hematopoietic cells. In addition, human ESC/iPSCs, with their unlimited proliferation ability, may be advantageous over somatic cells as the starting cell population for hematopoietic precursor cell differentiation.

1. Embryonic Stem Cells

Embryonic stem cell lines (ES cell lines) are cultures of cells derived from the epiblast tissue of the inner cell mass (ICM) of a blastocyst or earlier morula stage embryos. A blastocyst is an early stage embryo—approximately four to five days old in humans and consisting of 50-150 cells. ES cells are pluripotent and give rise during development to all derivatives of the three primary germ layers: ectoderm, endoderm and mesoderm. In other words, they can develop into each of the more than 200 cell types of the adult body when given sufficient and necessary stimulation for a specific cell type. They do not contribute to the extra-embryonic membranes or the placenta.

Most research to date used mouse embryonic stem cells (mES) or human embryonic stem cells (hES). Both have the essential stem cell characteristics, yet they require very different environments in order to maintain an undifferentiated state. Mouse ES cells may be grown on a layer of gelatin and require the presence of Leukemia Inhibitory Factor (LIF). Human ES cells could be grown on a feeder layer of mouse embryonic fibroblasts (MEFs) and often require the presence of basic Fibroblast Growth Factor (bFGF or FGF-2). Without optimal culture conditions or genetic manipulation (Chambers et al., 2003), embryonic stem cells will rapidly differentiate.

A human embryonic stem cell may also be defined by the presence of several transcription factors and cell surface proteins. The transcription factors Oct-4, Nanog, and Sox-2 form the core regulatory network that ensures the suppression of genes that lead to differentiation and the maintenance of pluripotency (Boyer et al., 2005). The cell surface antigens most commonly used to identify hES cells include the glycolipids SSEA3 and SSEA4 and the keratan sulfate antigens Tra-1-60 and Tra-1-81.

Methods for obtaining mouse ES cells are well known. In one method, a preimplantation blastocyst from the 129 strain of mice is treated with mouse antiserum to remove the trophoectoderm, and the inner cell mass is cultured on a feeder cell layer of chemically inactivated mouse embryonic fibroblasts in medium containing fetal calf serum. Colonies of undifferentiated ES cells that develop are subcultured on mouse embryonic fibroblast feeder layers in the presence of fetal calf serum to produce populations of ES cells. In some methods, mouse ES cells can be grown in the absence of a feeder layer by adding the cytokine leukemia inhibitory factor (LIF) to serum-containing culture medium (Smith, 2000). In other methods, mouse ES cells can be grown in serum-free medium in the presence of bone morphogenetic protein and LIF (Ying et al., 2003).

Human ES cells can be obtained from blastocysts using previously described methods (Thomson et al., 1995; Thomson et al., 1998; Thomson and Marshall, 1998; Reubinoff et al, 2000.) In one method, day-5 human blastocysts are exposed to rabbit anti-human spleen cell antiserum, then exposed to a 1:5 dilution of Guinea pig complement to lyse trophectoderm cells. After removing the lysed trophectoderm cells from the intact inner cell mass, the inner cell mass is cultured on a feeder layer of gamma-inactivated mouse embryonic fibroblasts and in the presence of fetal bovine serum. After 9 to 15 days, clumps of cells derived from the inner cell mass can be chemically (i.e. exposed to trypsin) or mechanically dissociated and replated in fresh medium containing fetal bovine serum and a feeder layer of mouse embryonic fibroblasts. Upon further proliferation, colonies having undifferentiated morphology are selected by micropipette, mechanically dissociated into clumps, and replated (see U.S. Pat. No. 6,833,269). ES-like morphology is characterized as compact colonies with apparently high nucleus to cytoplasm ratio and prominent nucleoli. Resulting ES cells can be routinely passaged by brief trypsinization or by selection of individual colonies by micropipette. In some methods, human ES cells can be grown without serum by culturing the ES cells on a feeder layer of fibroblasts in the presence of basic fibroblast growth factor (Amit et al., 2000). In other methods, human ES cells can be grown without a feeder cell layer by culturing the cells on a protein matrix such as matrigel or laminin in the presence of "conditioned" medium containing basic fibroblast growth factor (Xu et al., 2001). The medium is previously conditioned by coculturing with fibroblasts.

Methods for the isolation of rhesus monkey and common marmoset ES cells are also known (Thomson, and Marshall, 1998; Thomson et al., 1995; Thomson and Odorico, 2000).

Another source of ES cells are established ES cell lines. Various mouse cell lines and human ES cell lines are known and conditions for their growth and propagation have been defined. For example, the mouse CGR8 cell line was established from the inner cell mass of mouse strain 129 embryos, and cultures of CGR8 cells can be grown in the presence of LIF without feeder layers. As a further example, human ES cell lines H1, H7, H9, H13 and H14 were established by Thompson et al. In addition, subclones H9.1 and H9.2 of the H9 line have been developed. It is anticipated that virtually any ES or stem cell line known in the art may be used with the present invention, such as, e.g., those described in Yu and Thompson, 2008, which is incorporated herein by reference.

The source of ES cells for use in connection with the present invention can be a blastocyst, cells derived from culturing the inner cell mass of a blastocyst, or cells obtained from cultures of established cell lines. Thus, as used herein, the term "ES cells" can refer to inner cell mass cells of a blastocyst, ES cells obtained from cultures of inner mass cells, and ES cells obtained from cultures of ES cell lines.

2. Induced Pluripotent Stem Cells

Induced pluripotent stem (iPS) cells are cells that have the characteristics of ES cells but are obtained by the reprogramming of differentiated somatic cells. Induced pluripotent stem cells have been obtained by various methods. In one method, adult human dermal fibroblasts are transfected with transcription factors Oct4, Sox2, c-Myc and Klf4 using retroviral transduction (Takahashi et al., 2007). The transfected cells are plated on SNL feeder cells (a mouse cell fibroblast cell line that produces LIF) in medium supplemented with basic fibroblast growth factor (bFGF). After approximately 25 days, colonies resembling human ES cell colonies appear in culture. The ES cell-like colonies are picked and expanded on feeder cells in the presence of bFGF.

Based on cell characteristics, cells of the ES cell-like colonies are induced pluripotent stem cells. The induced pluripotent stem cells are morphologically similar to human ES cells, and express various human ES cell markers. Also, when grown under conditions that are known to result in differentiation of human ES cells, the induced pluripotent stem cells differentiate accordingly. For example, the induced pluripotent stem cells can differentiate into cells having hematopoietic cell structures and hematopoietic cell markers. It is anticipated that virtually any iPS cells or cell lines may be used with the present invention, including, e.g., those described in Yu and Thompson, 2008.

In another method, human fetal or newborn fibroblasts are transfected with four genes, Oct4, Sox2, Nanog and Lin28 using lentivirus transduction (Yu et al., 2007). At 12-20 days post infection, colonies with human ES cell morphology become visible. The colonies are picked and expanded. The induced pluripotent stem cells making up the colonies are morphologically similar to human ES cells, express various human ES cell markers, and form teratomas having neural tissue, cartilage, and gut epithelium after injection into mice.

Methods of preparing induced pluripotent stem cells from mouse are also known (Takahashi and Yamanaka, 2006). Induction of iPS cells typically require the expression of or exposure to at least one member from Sox family and at least one member from Oct family. Sox and Oct are thought to be central to the transcriptional regulatory hierarchy that specifies ES cell identity. For example, Sox may be Sox-1, Sox-2, Sox-3, Sox-15, or Sox-18; Oct may be Oct-4. Additional factors may increase the reprogramming efficiency, like Nanog, Lin28, Klf4, or c-Myc; specific sets of reprogramming factors may be a set comprising Sox-2, Oct-4, Nanog and, optionally, Lin-28; or comprising Sox-2, Oct4, Klf and, optionally, c-Myc.

iPS cells, like ES cells, have characteristic antigens that can be identified or confirmed by immunohistochemistry or flow cytometry, using antibodies for SSEA-1, SSEA-3 and SSEA-4 (Developmental Studies Hybridoma Bank, National Institute of Child Health and Human Development, Bethesda Md.), and TRA-1-60 and TRA-1-81 (Andrews et al., 1987). Pluripotency of embryonic stem cells can be confirmed by injecting approximately $0.5-10 \times 10^6$ cells into the rear leg muscles of 8-12 week old male SCID mice. Teratomas develop that demonstrate at least one cell type of each of the three germ layers.

In certain aspects of the present invention, iPS cells are made from reprogramming somatic cells using reprogramming factors comprising an Oct family member and a Sox family member, such as Oct4 and Sox2 in combination with Klf or Nanog as described above. The somatic cell for reprogramming may be any somatic cell that can be induced to pluripotency, such as a fibroblast, a keratinocyte, a hematopoietic cell, a mesenchymal cell, a liver cell, a stomach cell, or a β cell. In a certain aspect, T cells may also be used as source of somatic cells for reprogramming (see U.S. Application No. 61/184,546, incorporated herein by reference).

Reprogramming factors may be expressed from expression cassettes comprised in one or more vectors, such as an integrating vector or an episomal vector, e.g., an EBV element-based system (see U.S. Application No. 61/058, 858, incorporated herein by reference; Yu et al., 2009). In a further aspect, reprogramming proteins could be introduced directly into somatic cells by protein transduction (see U.S. Application No. 61/172,079, incorporated herein by reference).

3. Embryonic Stem Cells Derived by Somatic Cell Nuclear Transfer

Pluripotent stem cells can be prepared by means of somatic cell nuclear transfer, in which a donor nucleus is transferred into a spindle-free oocyte. Stem cells produced by nuclear transfer are genetically identical to the donor nuclei. In one method, donor fibroblast nuclei from skin fibroblasts of a rhesus macaque are introduced into the cytoplasm of spindle-free, mature metaphase II rhesus macaque ooctyes by electrofusion (Byrne et al., 2007). The fused oocytes are activated by exposure to ionomycin, then incubated until the blastocyst stage. The inner cell mass of selected blastocysts are then cultured to produce embryonic stem cell lines. The embryonic stem cell lines show normal ES cell morphology, express various ES cell markers, and differentiate into multiple cell types both in vitro and in vivo. As used herein, the term "ES cells" refers to embryonic stem cells derived from embryos containing fertilized nuclei. ES cells are distinguished from embryonic stem cells produced by nuclear transfer, which are referred to as "embryonic stem cells derived by somatic cell nuclear transfer."

4. Other Stem Cells

Fetal stem cells are cells with self-renewal capability and pluripotent differentiation potential. They can be isolated and expanded from fetal cytotrophoblast cells (European Patent EP0412700) and chorionic villi, amniotic fluid and the placenta (WO12003/042405). These references are hereby incorporated by reference in their entirety. Cell surface markers of fetal stem cells include $CD117/c-kit^+$, $SSEA3^+$, $SSEA4^+$ and $SSEA1^-$.

Somatic stem cells have been identified in most organ tissues. The best characterized is the hematopoietic stem cell, which is a type of hematopoietic precursor cell. A hematopoietic stem cell is a mesoderm-derived cell that has been purified based on cell surface markers and functional characteristics. The hematopoietic stem cell, isolated from bone marrow, blood, cord blood, fetal liver and yolk sac, is the progenitor cell that reinitiates hematopoiesis for the life of a recipient and generates multiple hematopoietic lineages (see U.S. Pat. Nos. 5,635,387; 5,460,964; 5,677,136; 5,750,397; 5,759,793; 5,681,599; 5,716,827; Hill et al., 1996; all of which are hereby incorporated by reference in their entirety). When transplanted into lethally irradiated animals or humans, hematopoietic stem cells can repopulate the erythroid, neutrophil-macrophage, megakaryocyte and lymphoid hematopoietic cell pool. In vitro, hematopoietic stem cells can be induced to undergo at least some self-renewing cell divisions and can be induced to differentiate to the same lineages as is seen in vivo. Therefore, this cell fulfills the criteria of a stem cell.

The next best characterized is the mesenchymal stem cells (MSC), originally derived from the embryonic mesoderm and isolated from adult bone marrow, can differentiate to form muscle, bone, cartilage, fat, marrow stroma, and tendon. During embryogenesis, the mesoderm develops into limb-bud mesoderm, tissue that generates bone, cartilage, fat, skeletal muscle and possibly endothelium. Mesoderm also differentiates to visceral mesoderm, which can give rise to cardiac muscle, smooth muscle, or blood islands consisting of endothelium and hematopoietic progenitor cells. Primitive mesodermal or mesenchymal stem cells, therefore, could provide a source for a number of cell and tissue types. A number of mesenchymal stem cells have been isolated (see, for example, U.S. Pat. Nos. 5,486,359; 5,827,735; 5,811,094; 5,736,396; U.S. Pat. Nos. 5,837,539; 5,837,670; 5,827,740; Jaiswal et al., 1997; Cassiede et al., 1996; Johnstone et al., 1998; Yoo et al., 1998; Gronthos, 1994; Makino et al., 1999, all of which are hereby incorporated by reference in their entirety). Of the many mesenchymal stem cells that have been described, all have demonstrated limited differentiation to form only those differentiated cells generally considered to be of mesenchymal origin. To date, the most multipotent mesenchymal stem cell expresses the $SH2^+$ $SH4^+$ $CD29^+$ $CD44^+$ $CD71^+$ $CD90^+$ $CD106^+$ $CD120a^+$ $CD124^+$ $CD14^-$ $CD34^-$ $CD45^-$ phenotype.

Other stem cells have been identified, including gastrointestinal stem cells, epidermal stem cells, neural and hepatic stem cells, also termed oval cells (Potten, 1998; Watt, 1997; Alison et al, 1998).

In some embodiments, the stem cells useful for methods described herein include, but are not limited to, embryonic stem cells, induced plurpotent stem cells, mesenchymal stem cells, bone-marrow derived stem cells, hematopoietic stem cells, chrondrocyte progenitor cells, epidermal stem cells, gastrointestinal stem cells, neural stem cells, hepatic stem cells, adipose-derived mesenchymal stem cells, pancreatic progenitor cells, hair follicular stem cells, endothelial progenitor cells, and smooth muscle progenitor cells.

In some embodiments, the stem cells used for methods described herein are isolated from umbilical cord, placenta, amniotic fluid, chorion villi, blastocysts, bone marrow, adipose tissue, brain, peripheral blood, the gastrointestinal tract, cord blood, blood vessels, skeletal muscle, skin, liver, and menstrual blood. Stem cells prepared in the menstrual blood are called endometrial regenerative cells (available from Medistem, Inc.).

One ordinarily skilled in the art can locate, isolate, and expand such stem cells. The detailed procedures for the isolation of human stem cells from various sources are described in Current Protocols in Stem Cell Biology (2007), which is hereby incorporated by reference in its entirety. Alternatively, commercial kits and isolation systems can be used—e.g., the BD FACSAria cell sorting system, BD IMag magnetic cell separation system, and BD IMag mouse hematopoietic progenitor cell enrichment set from BD Biosciences. Methods of isolating and culturing stem cells from various sources are also described in U.S. Pat. Nos. 5,486,359, 6,991,897, 7,015,037, 7,422,736, 7,410,798, 7,410,773, 7,399,632; and these are hereby incorporated by reference in their entirety.

B. Somatic Cells

In certain aspects of the invention, there may also be provided methods of transdifferentiation, i.e., the direct conversion of one somatic cell type into another, e.g., deriving hematopoietic precursor cells or hematopoietic cells from non-hematopoietic somatic cells. However, human somatic cells may be limited in supply, especially those from living donors. In certain aspects, to provide an unlimited supply of starting cells for programming, somatic cells may be immortalized by introduction of immortalizing genes or proteins, such as hTERT or oncogenes. The immortalization of cells may be reversible (e.g., using removable expression cassettes) or inducible (e.g., using inducible promoters).

Somatic cells in certain aspects of the invention may be primary cells (non-immortalized cells), such as those freshly isolated from an animal, or may be derived from a cell line (immortalized cells). The cells may be maintained in cell culture following their isolation from a subject. In certain embodiments, the cells are passaged once or more than once (e.g., between 2-5, 5-10, 10-20, 20-50, 50-100 times, or more) prior to their use in a method of the invention. In some embodiments the cells will have been passaged no more than 1, 2, 5, 10, 20, or 50 times prior to their use in a method of the invention. They may be frozen, thawed, etc.

The somatic cells used or described herein may be native somatic cells, or engineered somatic cells, i.e., somatic cells which have been genetically altered. Somatic cells of the present invention are typically mammalian cells, such as, for example, human cells, primate cells or mouse cells. They may be obtained by well-known methods and can be obtained from any organ or tissue containing live somatic cells, e.g., blood, bone marrow, skin, lung, pancreas, liver, stomach, intestine, heart, reproductive organs, bladder, kidney, urethra and other urinary organs, etc.

Mammalian somatic cells useful in the present invention include, but are not limited to, Sertoli cells, endothelial cells, granulosa cells, neurons, pancreatic islet cells, epidermal cells, epithelial cells, hepatocytes, hair follicle cells, keratinocytes, hematopoietic cells, melanocytes, chondrocytes, lymphocytes (B and T lymphocytes), erythrocytes, macrophages, monocytes, mononuclear cells, cardiac muscle cells, and other muscle cells, etc.

In some embodiments, cells are selected based on their expression of an endogenous marker known to be expressed only or primarily in a desired cell type. For example, vimentin is a fibroblast marker. Other useful markers include various keratins, cell adhesion molecules such as cadherins, fibronectin, CD molecules, etc. The population of somatic cells may have an average cell cycle time of between 18 and 96 hours, e.g., between 24-48 hours, between 48-72 hours, etc. In some embodiments, at least 90%, 95%, 98%, 99%, or more of the cells would be expected to divide within a predetermined time such as 24, 48, 72, or 96 hours.

Methods described herein may be used to program one or more somatic cells, e.g., colonies or populations of somatic cells into hematopoietic precursor cells. In some embodiments, a population of cells of the present invention is substantially uniform in that at least 90% of the cells display a phenotype or characteristic of interest. In some embodiments at least 95%, 96%, 97%, 98%, 99%, 99.5%, 99.8%, 99.9, 99.95% or more of the cells display a phenotype or characteristic of interest. In certain embodiments of the invention the somatic cells have the capacity to divide, i.e., the somatic cells are not post-mitotic.

Somatic cells may be partially or completely differentiated. Differentiation is the process by which a less specialized cell becomes a more specialized cell type. Cell differentiation can involve changes in the size, shape, polarity, metabolic activity, gene expression and/or responsiveness to signals of the cell. For example, hematopoietic stem cells differentiate to give rise to all the blood cell types including myeloid (monocytes and macrophages, neutrophils, basophils, eosinophils, erythrocytes, megakaryocytes/platelets, dendritic cells), erythro-megakaryocytic (erythrocytes, megakaryocytes, thrombocytes), and lymphoid lineages (T-cells, B-cells, natural killer (NK) cells). During progression along the path of differentiation, the ultimate fate of a cell becomes more fixed. As described herein, both partially differentiated somatic cells and fully differentiated somatic cells can be programmed as described herein to produce desired cell types such as hematopoietic cells and hematopoietic precursor cells.

III. HEMATOPOIETIC PRECURSOR CELL PROGRAMMING FACTORS

Certain aspects of the invention provide hematopoietic precursor cell programming factors for hematopoietic programming. The hematopoietic cells or hematopoietic precursor cells could be produced directly from other cell sources by increasing the level of hematopoietic precursor programming factors in cells. The numerous functions of hematopoietic precursor cells could be controlled at the transcriptional level by the concerted actions of a limited number of hematopoietic cell-enriched transcription factors. Any transcription factors important for hematopoietic cell or hematopoietic precursor differentiation or function may be used herein, like hematopoietic cell-enriched transcription factors or hematopoietic precursor cell-enriched transcription factors, particularly the genes thereof listed in this section. The inventors also contemplate that all isoforms and variants of the genes listed in this section are included in this invention, and non-limiting examples of accession numbers for certain isoforms or variants are provided.

Table 1 provides a list of genes for forward programming of human ESCs or iPSCs—or for transdifferentiation of somatic cells—to hematopoietic cells or hematopoietic precursor cells. All of the gene sequence and related information provided by the listed Gene ID and Accession numbers is hereby incorporated by reference as of the filing date of this application.

TABLE 1

Genes for forward programming of human ESCs/iPSCs to hematopoietic cells or hematopoietic precursor cells

| # | Symbol | Gene ID | Accession | Full name |
|---|--------|---------|-----------|-----------|
| Genes involved in specification of hematopoietic cells | | | | |
| 1 | CEBPA | 1050 | NM_004364 | CCAAT/enhancer binding protein (C/EBP), alpha |
| 2 | ERG | 2078 | NM_004449 | v-ets erythroblastosis virus E26 oncogene homolog (avian) |
|   |       |      | NM_001136154 | |
|   |       |      | NM_001136155 | |
|   |       |      | NM_001243438 | |
|   |       |      | NM_001243429 | |
|   |       |      | NM_001243432 | |
|   |       |      | NM_182918 | |
| 3 | ETV2 | 2116 | NM_014209 | Ets variant 2 |
| 4 | FLI1 | 2313 | NM_002017 | Friend leukemia virus integration 1 |
|   |       |      | NM_001167681 | |
| 5 | GATA2 | 2624 | NM_032638 | GATA binding protein 2 |
|   |       |      | NM_001145661 | |
|   |       |      | NM_001145662 | |
| 6 | GATA3 | 2625 | NM_001002295 | GATA binding protein 3 |
|   |       |      | NM_002051 | |

TABLE 1-continued

Genes for forward programming of human ESCs/iPSCs to hematopoietic cells or hematopoietic precursor cells

| # | Symbol | Gene ID | Accession | Full name |
|---|---|---|---|---|
| 7 | GFI1 | 2672 | NM_005263<br>NM_001127215<br>NM_001127216 | Growth factor independent 1 transcription repressor |
| 8 | GFI1B | 8328 | NM_004188<br>NM_001135031 | Growth factor independent 1B transcription repressor |
| 9 | IKZF1 | 10320 | NM_006060 | IKAROS family zinc finger 1 (Ikaros) |
| 10 | LMO2 | 4005 | NM_005574<br>NM_001142315 | LIM domain only 2 (rhombotin-like 1) |
| 11 | LYL1 | 4066 | NM_005583 | Lymphoblastic leukemia derived sequence 1 |
| 12 | MLLT3 | 4300 | NM_004529 | myeloid/lymphoid or mixed-lineage leukemia (trithorax homolog, *Drosophila*); translocated to, 3 |
| 13 | NFE2 | 4778 | NM_006163 | Nuclear factor (erythroid-derived 2), 45 kDa |
| 14 | RUNX1 | 861 | NM_001122607<br>NM_001001890<br>NM_001754 | Runt-related transcription factor 1 |
| 15 | SPI1 | 6688 | NM_003120 | Spleen focus forming virus (SFFV) proviral integration oncogene spi1 |
| 16 | TAL1 | 6886 | NM_003189 | T-cell acute lymphocytic leukemia 1 |

Genes involved in maintenance/proliferation of hematopoietic cells

| # | Symbol | Gene ID | Accession | Full name |
|---|---|---|---|---|
| 17 | BMI1 | 648 | NM_005180 | BMI1 polycomb ring finger oncogene |
| 18 | CBFA2T3 | 863 | NM_005187<br>NM_175931 | Core-binding factor, runt domain, alpha subunit 2; translocated to, 3 |
| 19 | EZH2 | 2146 | NM_001203247<br>NM_001203248<br>NM_001203249<br>NM_004456<br>NM_152998 | Enhancer of zeste homolog 2 |
| 20 | FOSB | 2354 | NM_006732<br>NM_001114171 | FBJ murine osteosarcoma viral oncogene homolog B |
| 21 | HLF | 3131 | NM_002126 | Hepatic leukemia factor |
| 22 | HOXA10 | 3206 | NM_018951<br>NM_153715 | Homeobox A10 |
| 23 | HOXA4 | 3201 | NM_002141 | Homeobox A4 |
| 24 | HOXA5 | 3202 | NM_019102 | Homeobox A5 |
| 25 | HOXA6 | 3203 | NM_024014 | Homeobox A6 |
| 26 | HOXA7 | 3204 | NM_006896 | Homeobox A7 |
| 27 | HOXA9 | 3205 | NM_152739 | Homeobox A9 |
| 28 | HOXB4 | 3214 | NM_024015 | Homeobox B4 |
| 29 | JUNB | 3726 | NM_002229 | Jun B proto-oncogene |
| 30 | LHX2 | 9355 | NM_004789 | LIM homeobox 2 |
| 31 | MECOM(EVI1) | 2122 | NM_001105077<br>NM_001105078<br>NM_001163999<br>NM_001164000<br>NM_001205194<br>NM_004991<br>NM_005241 | MDS1 and EVI1 complex locus |
| 32 | MYB | 4602 | NM_005375<br>NM_001161660<br>NM_001161659<br>NM_001161658<br>NM_001161657<br>NM_001161656<br>NM_001130173<br>NM_001130172 | v-myb myeloblastosis viral oncogene homolog (avian) |
| 33 | MYC | 4609 | NM_002467 | |
| 34 | PRDM16 | 63976 | NM_022114<br>NM_199454 | PR domain containing 16 |

Other genes expressed in hematopoietic cells

| # | Symbol | Gene ID | Accession | Full name |
|---|---|---|---|---|
| 35 | ARID5A | 10865 | NM_212481 | AT rich interactive domain 5A (MRF1-like) |
| 36 | KLF4 | 9314 | NM_004235 | Kruppel-like factor 4 (gut) |
| 37 | ZBED3 | 84327 | NM_032367 | zinc finger, BED-type containing 3 |
| 38 | ZEB2 | 9839 | NM_014795<br>NM_001171653 | zinc finger E-box binding homeobox 2 |
| 39 | ZFX | 7543 | NM_003410 | zinc finger protein, X-linked |
| 40 | ZNF429 | 353088 | NM_001001415 | zinc finger protein 429 |
| 41 | ZNF514 | 84874 | NM_032788 | zinc finger protein 514 |
| 42 | ZNF547 | 284306 | NM_173631 | zinc finger protein 547 |
| 43 | ZNF562 | 54811 | NM_001130031<br>NM_001130032<br>NM_017656 | zinc finger protein 562 |
| 44 | ZNF595 | 152687 | NM_182524 | zinc finger protein 595 |

For example, by effecting expression of transcription factors disclosed herein, the differentiation into hematopoietic precursor cells from pluripotent stem cells or somatic cells may bypass most, if not all, normal developmental stages.

In certain embodiments, a hematopoietic precursor programming factor is a factor that is an endothelial differentiation factor, meaning that it is important for initial differentiation of pluripotent cells to endothelial cells. For example, a hematopoietic precursor factor may be the endothelial differentiation factor called ERG (Gene ID 2078 in Table I), which is also known as: transcriptional regulator ERG, ets-related transforming protein ERG, TMPRSS2-ERG prostate cancer specific, v-ets erythroblastosis virus E26 oncogene like, v-ets avian erythroblastosis virus E26 oncogene related, or transforming protein ERG. The ERG used may be any isoform or variant of ERG including, for example, those provided in Table 1. In some embodiments, a hematopoietic precursor programming factor is a particular isoform of ERG, such as ERG isoform 2 (ERG-2) (SEQ ID NOs:1 and 2, Accession No. NM_004449) or ERG isoform 3 (ERG-3) (SEQ ID NOs:3 and 4, Accession No. NM_001136154). In particular embodiments, a hematopoietic precursor programming factor is ERG isoform 3. In other aspects, a hematopoietic precursor programming factor may any other factor provided in Table 1, or any isoform or variant thereof. For example, the hematopoietic precursor programming factor may be FLI-1 (Friend leukemia virus integration 1) (e.g. SEQ ID NOs:5 and 6, Gene ID 2313; Accession No. NM_002017), or ETV2 (ets variant 2, also called ER71, Etsrp71) (SEQ ID NOs:27 and 28, Gene ID 2116; Accession No. NM_014209). In yet other aspects, a hematopoietic precursor programming factor is v-ets erythroblastosis virus E26 oncogene homolog 1 (avian) (ETS1), V-ets erythroblastosis virus E26 oncogene homolog 2 (avian) (ETS2), ELF-1, TEL, TAL1 (SCL), GATA2, FOXC2, FOXO1, FOXO3, FOXF1, SOX7, or SOX18.

In some embodiments, a hematopoietic precursor programming factor is any one of the genes included in Table 1, which includes genes involved in the specification of hematopoietic cells, genes involved in the maintenance and/or proliferation of hematopoietic cells, and genes expressed in hematopoietic cells.

In certain embodiments, two or more hematopoietic precursor programming factors are used in combination for forward programming or transdifferentiation to provide hematopoietic cells or hematopoietic precursor cells. For example, at least one hematopoietic precursor programming factor, such as an endothelial differentiation factor (e.g., ERG, FLI-1, ETV2, or any of the other such factors listed in this section) can be combined with one or more additional hematopoietic precursor factors. In particular embodiments, forward programming or transdifferentiation to provide hematopoietic precursor cells includes one or more hematopoietic precursor programming factors selected from ERG, FLI-1, or ETV2, in combination with one or more hematopoietic precursor programming factor genes selected from GFI1 (e.g., SEQ ID NOs:7 and 8, Gene ID 2672, Accession No. NM_005263), GFI1B (e.g., SEQ ID NOs: 29 and 30, Gene ID 8328, Accession No. NM_004188), LMO2 (e.g., SEQ ID NOs: 31 and 32, Gene ID 4005, Accession No. NM_005574); TAL1 (SEQ ID NOs:9 and 10, Gene ID 6886, Accession No. NM_003189), LYL1 (SEQ ID NOs:11 and 12, Gene ID 4066, Acc. No. NM_005583), GATA2 (e.g., SEQ ID NOs:13 and 14, Gene ID 2624, Accession No. NM_032638), GATA3 (e.g., SEQ ID NOs:15 and 16, Gene ID 2625, Accession No. NM_001002295), or SPI1 (SEQ ID NOs:17 and 18, Gene ID 6688, Accession No. NM_003120).

For example, in certain aspects, forward programming or transdifferentiation may be accomplished by using ERG in combination with one or more other hematopoietic precursor programming factors listed in Table 1. In some embodiments, forward programming or transdifferentiation may be accomplished by using ERG (e.g., ERG-3) in combination with GFI1, by using ERG (e.g., ERG-3) in combination with GATA2, or by using GATA2 in combination with TAL1 and LMO2.

In some embodiments, forward programming or transdifferentiation to provide hematopoietic cells or hematopoietic precursor cells may be accomplished by increasing the expression of any one or more of the hematopoietic precursor programming factors described in this section.

IV. DELIVERY OF GENES OR GENE PRODUCTS

In certain embodiments, vectors for delivery of nucleic acids encoding hematopoietic precursor or hematopoietic cell programming or differentiation factors may be constructed to express those factors in cells. Details of components of such vectors and delivery methods are disclosed below. In addition, protein transduction compositions or methods may be used to effect expression of the programming factors.

In a further aspect, the following systems and methods may also be used in delivery of a reporter expression cassette for identification of desired cell types, such as hematopoietic precursor cells. In particular, a regulatory element specific for hematopoietic cells or hematopoietic precursors may be used to drive expression of a reporter gene. Therefore hematopoietic cells or precursors derived from programming may be characterized, selected, or enriched via use of the reporter.

A. Nucleic Acid Delivery Systems

One of skill in the art would be well-equipped to construct a vector through standard recombinant techniques (see, for example, Sambrook et al., 2001 and Ausubel et al., 1996, both incorporated herein by reference). Vectors include but are not limited to, plasmids, cosmids, viruses (bacteriophage, animal viruses, and plant viruses), and artificial chromosomes (e.g., YACs), such as retroviral vectors (e.g. derived from Moloney murine leukemia virus vectors (MoMLV), MSCV, SFFV, MPSV, SNV etc), lentiviral vectors (e.g. derived from HIV-1, HIV-2, SIV, BIV, FIV etc.), adenoviral (Ad) vectors including replication competent, replication deficient and gutless forms thereof, adeno-associated viral (AAV) vectors, simian virus 40 (SV-40) vectors, bovine papilloma virus vectors, Epstein-Barr virus vectors, herpes virus vectors, vaccinia virus vectors, Harvey murine sarcoma virus vectors, murine mammary tumor virus vectors, Rous sarcoma virus vectors.

1. Viral Vectors

In generating recombinant viral vectors, non-essential genes are typically replaced with a gene or coding sequence for a heterologous (or non-native) protein. A viral vector is a kind of expression construct that utilizes viral sequences to introduce nucleic acid and possibly proteins into a cell. The ability of certain viruses to infect cells or enter cells via receptor-mediated endocytosis, and to integrate into host cell genomes and express viral genes stably and efficiently have made them attractive candidates for the transfer of foreign nucleic acids into cells (e.g., mammalian cells).

Non-limiting examples of virus vectors that may be used to deliver a nucleic acid of certain aspects of the present invention are described below.

Retroviruses have promise as gene delivery vectors due to their ability to integrate their genes into the host genome, transfer a large amount of foreign genetic material, infect a broad spectrum of species and cell types, and be packaged in special cell-lines (Miller, 1992).

In order to construct a retroviral vector, a nucleic acid is inserted into the viral genome in place of certain viral sequences to produce a virus that is replication-defective. In order to produce virions, a packaging cell line containing the gag, pol, and env genes—but without the LTR and packaging components—is constructed (Mann et al., 1983). When a recombinant plasmid containing a cDNA, together with the retroviral LTR and packaging sequences, is introduced into a special cell line (e.g., by calcium phosphate precipitation), the packaging sequence allows the RNA transcript of the recombinant plasmid to be packaged into viral particles, which are then secreted into the culture medium (Nicolas and Rubenstein, 1988; Temin, 1986; Mann et al., 1983). The medium containing the recombinant retroviruses is then collected, optionally concentrated, and used for gene transfer. Retroviral vectors are able to infect a broad variety of cell types. However, integration and stable expression require the division of host cells (Paskind et al., 1975).

Lentiviruses are complex retroviruses, which, in addition to the common retroviral genes gag, pol, and env, contain other genes with regulatory or structural function. Lentiviral vectors are well known in the art (see, for example, Naldini et al., 1996; Zufferey et al., 1997; Blomer et al., 1997; U.S. Pat. Nos. 6,013,516 and 5,994,136).

Recombinant lentiviral vectors are capable of infecting non-dividing cells and can be used for both in vivo and ex vivo gene transfer and expression of nucleic acid sequences. For example, recombinant lentivirus capable of infecting a non-dividing cell—wherein a suitable host cell is transfected with two or more vectors carrying the packaging functions, namely gag, pol and env, as well as rev and tat—is described in U.S. Pat. No. 5,994,136, incorporated herein by reference.

2. Episomal Vectors

The use of plasmid- or liposome-based extra-chromosomal (i.e., episomal) vectors may be also provided in certain aspects of the invention. Such episomal vectors may include, e.g., oriP-based vectors, and/or vectors encoding a derivative of EBNA-1. These vectors may permit large fragments of DNA to be introduced unto a cell and maintained extra-chromosomally, replicated once per cell cycle, partitioned to daughter cells efficiently, and elicit substantially no immune response.

In particular, EBNA-1, the only viral protein required for the replication of the oriP-based expression vector, does not elicit a cellular immune response because it has developed an efficient mechanism to bypass the processing required for presentation of its antigens on MHC class 1 molecules (Levitskaya et al., 1997). Further, EBNA-1 can act in trans to enhance expression of the cloned gene, inducing expression of a cloned gene up to 100-fold in some cell lines (Langle-Rouault et al., 1998; Evans et al., 1997). Finally, the manufacture of such oriP-based expression vectors is inexpensive.

Other extra-chromosomal vectors include other lymphotrophic herpes virus-based vectors. Lymphotrophic herpes virus is a herpes virus that replicates in a lymphoblast (e.g., a human B lymphoblast) and becomes a plasmid for a part of its natural life-cycle. Herpes simplex virus (HSV) is not a "lymphotrophic" herpes virus. Exemplary lymphotrophic herpes viruses include, but are not limited to EBV, Kaposi's sarcoma herpes virus (KSHV); Herpes virus saimiri (HS) and Marek's disease virus (MDV). Other sources of episome-base vectors are also contemplated, such as yeast ARS, adenovirus, SV40, or BPV.

One of skill in the art would be well-equipped to construct a vector through standard recombinant techniques (see, for example, Maniatis et al., 1988 and Ausubel et al., 1994, both incorporated herein by reference).

Vectors can also comprise other components or functionalities that further modulate gene delivery and/or gene expression, or that otherwise provide beneficial properties to the targeted cells. Such other components include, for example, components that influence binding or targeting to cells (including components that mediate cell-type or tissue-specific binding); components that influence uptake of the vector nucleic acid by the cell; components that influence localization of the polynucleotide within the cell after uptake (such as agents mediating nuclear localization); and components that influence expression of the polynucleotide.

Such components also may include markers, such as detectable and/or selection markers that can be used to detect or select for cells that have taken up and are expressing the nucleic acid delivered by the vector. Such components can be provided as a natural feature of the vector (such as the use of certain viral vectors that have components or functionalities mediating binding and uptake), or vectors can be modified to provide such functionalities. A large variety of such vectors are known in the art and are generally available. When a vector is maintained in a host cell, the vector can either be stably replicated by the cells during mitosis as an autonomous structure, incorporated within the genome of the host cell, or maintained in the host cell's nucleus or cytoplasm.

3. Transposon-Based System

According to a particular embodiment the introduction of nucleic acids may use a transposon-transposase system. The used transposon-transposase system could be the well known Sleeping Beauty, the Frog Prince transposon-transposase system (for a description of the latter, see, e.g., EP1507865), or the TTAA-specific transposon piggyBac system.

Transposons are sequences of DNA that can move around to different positions within the genome of a single cell, a process called transposition. In the process, they can cause mutations and change the amount of DNA in the genome. Transposons were also once called jumping genes, and are examples of mobile genetic elements.

There are a variety of mobile genetic elements, and they can be grouped based on their mechanism of transposition. Class I mobile genetic elements, or retrotransposons, copy themselves by first being transcribed to RNA, then reverse transcribed back to DNA by reverse transcriptase, and then being inserted at another position in the genome. Class II mobile genetic elements move directly from one position to another using a transposase to "cut and paste" them within the genome.

4. mRNA Delivery

One of skill in the art would be well-equipped to deliver to a cell any mRNA useful in the invention. For example, such techniques are provided in Yamamoto et al., 2009.

5. Homologous Recombination

In certain aspects of the invention, nucleic acid molecules can be introduced into cells in a specific manner for genome engineering, for example, via homologous recombination. As discussed above, some approaches to express genes in cells involve the use of viral vectors or transgenes that integrate randomly in the genome. These approaches, however, have the drawback of integration occurring either at sites that are unable to effectively mediate expression from the integrated nucleic or that result in the disruption of native genes. Problems associated with random integration could be partially overcome by homologous recombination to a specific locus in the target genome, e.g., Rosa26 locus.

Homologous recombination (HR), also known as general recombination, is a type of genetic recombination used in all forms of life in which nucleotide sequences are exchanged between two similar or identical strands of DNA. The technique has been the standard method for genome engineering in mammalian cells since the mid 1980s. The process involves several steps of physical breaking and the eventual rejoining of DNA. This process is most widely used to repair potentially lethal double-strand breaks in DNA. In addition, homologous recombination produces new combinations of DNA sequences during meiosis, the process by which eukaryotes make germ cells like sperm and ova. These new combinations of DNA represent genetic variation in offspring which allow populations to evolutionarily adapt to changing environmental conditions over time. Homologous recombination is also used in horizontal gene transfer to exchange genetic material between different strains and species of bacteria and viruses. Homologous recombination is also used as a technique in molecular biology for introducing genetic changes into target organisms.

Homologous recombination can be used as targeted genome modification. The efficiency of standard HR in mammalian cells is only 10-6 to 10-9 of cells treated (Capecchi, 1990). The use of meganucleases, or homing endonucleases, such as I-SceI have been used to increase the efficiency of HR. Both natural meganucleases as well as engineered meganucleases with modified targeting specificities have been utilized to increase HR efficiency (Pingoud and Silva, 2007; Chevalier et al., 2002).

On the path toward increasing the efficiency of HR has been to engineer chimeric endonucleases with programmable DNA specificity domains (Silva et al., 2011). Zinc-finger nucleases (ZFN) are one example of such a chimeric molecule in which Zinc-finger DNA binding domains are fused with the catalytic domain of a Type IIS restriction endonuclease such as FokI (as reviewed in Durai et al., 2005; PCT/US2004/030606).

Another class of such specificity molecules includes Transcription Activator Like Effector (TALE) DNA binding domains fused to the catalytic domain of a Type IIS restriction endonuclease such as FokI (Miller et al., 2011; PCT/IB2010/000154). TALENs can be designed for site-specific genome modification at virtually any given site of interest (Cermak et al., 2011; Christian et al., 2010; Li et al., 2011; Miller et al., 2011; Weber et al., 2011; Zhang et al., 2011). The site-specific DNA binding domain is expressed as a fusion protein with a DNA cleavage enzyme such as Fok I. The DNA binding domain is a scaffold of repeating amino acids; linking each of the repeats are two variable amino acids that bind to a single nucleotide in the DNA. For example, Asn-Asn binds guanosine, Asn-Ile binds adenosine, Asn-Gly bind thymidine, and His-Asp binds Cytosine. These two amino acids are known as the Repeat Variable Diresidue or RVD. There are many different RVD's and they can be engineered into the TAL Effector/Fok1 protein construct to create a specific TALEN. The RNA encoding the recombinant TALEN can then be purified and transfected into a cell for site-specific genome modification. Once the TALEN introduces the double strand DNA break, the DNA can be modified by non-homologous end joining (NHEJ) or by homologous directed repair (HDR). This allows DNA mutagenesis, deletions, or additions depending on what additional sequences are present during the DNA repair.

B. Regulatory Elements

Eukaryotic expression cassettes included in vectors useful in the invention preferably contain (in a 5'-to-3' direction) a eukaryotic transcriptional promoter operably linked to a protein-coding sequence, splice signals including intervening sequences, and a transcriptional termination/polyadenylation sequence.

1. Promoter/Enhancers

A "promoter" is a control sequence that is a region of a nucleic acid sequence at which initiation and rate of transcription are controlled. It may contain genetic elements at which regulatory proteins and molecules may bind, such as RNA polymerase and other transcription factors, to initiate the specific transcription of a nucleic acid sequence. The phrases "operatively positioned," "operatively linked," "under control," and "under transcriptional control" mean that a promoter is in a correct functional location and/or orientation in relation to a nucleic acid sequence to control transcriptional initiation and/or expression of that sequence.

A promoter generally comprises a sequence that functions to position the start site for RNA synthesis. The best known example of this is the TATA box, but in some promoters lacking a TATA box, such as, for example, the promoter for the mammalian terminal deoxynucleotidyl transferase gene and the promoter for the SV40 late genes, a discrete element overlying the start site itself helps to fix the place of initiation. Additional promoter elements regulate the frequency of transcriptional initiation. Typically, these are located in the region 30-110 bp upstream of the start site, although a number of promoters have been shown to contain functional elements downstream of the start site as well. To bring a coding sequence "under the control of" a promoter, one positions the 5' end of the transcription initiation site of the transcriptional reading frame "downstream" of (i.e., 3' of) the chosen promoter. The "upstream" promoter stimulates transcription of the DNA and promotes expression of the encoded RNA.

The spacing between promoter elements frequently is flexible, so that promoter function is preserved when elements are inverted or moved relative to one another. In the tk promoter, the spacing between promoter elements can be increased to 50 bp apart before activity begins to decline. Depending on the promoter, it appears that individual elements can function either cooperatively or independently to activate transcription. A promoter may or may not be used in conjunction with an "enhancer," which refers to a cis-acting regulatory sequence involved in the transcriptional activation of a nucleic acid sequence.

A promoter may be one naturally associated with a nucleic acid sequence, as may be obtained by isolating the 5' non-coding sequences located upstream of the coding segment and/or exon. Such a promoter can be referred to as "endogenous." Similarly, an enhancer may be one naturally associated with a nucleic acid sequence, located either downstream or upstream of that sequence. Alternatively, certain advantages will be gained by positioning the coding nucleic acid segment under the control of a recombinant or heterologous promoter, which refers to a promoter that is not normally associated with a nucleic acid sequence in its natural environment. A recombinant or heterologous enhancer refers also to an enhancer not normally associated with a nucleic acid sequence in its natural environment. Such promoters or enhancers may include promoters or enhancers of other genes, and promoters or enhancers isolated from any other virus, or prokaryotic or eukaryotic cell, and promoters or enhancers not "naturally occurring," i.e., containing different elements of different transcriptional regulatory regions, and/or mutations that alter expression. For example, promoters that are most commonly used in recombinant DNA construction include the β-lactamase (penicillinase), lactose and tryptophan (trp) promoter systems. In addition to producing nucleic acid sequences of promoters and enhancers synthetically, sequences may be produced using recombinant cloning and/or nucleic acid amplification technology, including PCR™, in connection with the compositions disclosed herein (see U.S. Pat. Nos. 4,683,202 and 5,928,906, each incorporated herein by reference). Furthermore, it is contemplated that the control sequences that direct transcription and/or expression of sequences within non-nuclear organelles such as mitochondria, chloroplasts, and the like, can be employed as well.

Naturally, it will be important to employ a promoter and/or enhancer that effectively directs the expression of the DNA segment in the organelle, cell type, tissue, organ, or organism chosen for expression. Those of skill in the art of molecular biology generally know the use of promoters, enhancers, and cell type combinations for protein expression, (see, for example Sambrook et al. 1989, incorporated herein by reference). The promoters employed may be constitutive, tissue-specific, inducible, and/or useful under the appropriate conditions to direct high level expression of the introduced DNA segment, such as is advantageous in the large-scale production of recombinant proteins and/or peptides. The promoter may be heterologous or endogenous.

Additionally any promoter/enhancer combination (as per, for example, the Eukaryotic Promoter Data Base EPDB, through world wide web at epd.isb-sib.ch/) could also be used to drive expression. Use of a T3, T7 or SP6 cytoplasmic expression system is another possible embodiment. Eukaryotic cells can support cytoplasmic transcription from certain bacterial promoters if the appropriate bacterial polymerase is provided, either as part of the delivery complex or as an additional genetic expression construct.

Non-limiting examples of promoters include early or late viral promoters, such as, SV40 early or late promoters, cytomegalovirus (CMV) immediate early promoters, Rous Sarcoma Virus (RSV) early promoters; eukaryotic cell promoters, such as, e.g., beta actin promoter (Ng, 1989; Quitsche et al., 1989), GADPH promoter (Alexander et al., 1988, Ercolani et al., 1988), metallothionein promoter (Karin et al., 1989; Richards et al., 1984); and concatenated response element promoters, such as cyclic AMP response element promoters (cre), serum response element promoter (sre), phorbol ester promoter (TPA) and response element promoters (tre) near a minimal TATA box. It is also possible to use human growth hormone promoter sequences (e.g., the human growth hormone minimal promoter described at Genbank, accession no. X05244, nucleotide 283-341) or a mouse mammary tumor promoter (available from the ATCC, Cat. No. ATCC 45007). A specific example could be a phosphoglycerate kinase (PGK) promoter.

Tissue-specific transgene expression, especially for reporter gene expression in hematopoietic cells and precursors of hematopoietic cells derived from programming, may be desirable as a way to identify derived hematopoietic cells and precursors. To increase both specificity and activity, the use of cis-acting regulatory elements has been contemplated. For example, a hematopoietic cell-specific promoter may be used. Many such hematopoietic cell-specific promoters are known in the art, such as promoters of the hematopoietic genes provided in Table 1.

In certain aspects, methods of the invention also concern enhancer sequences, i.e., nucleic acid sequences that increase a promoter's activity and that have the potential to act in cis, and regardless of their orientation, even over relatively long distances (up to several kilobases away from the target promoter). However, enhancer function is not necessarily restricted to such long distances as they may also function in close proximity to a given promoter.

Many hematopoietic cell promoter and enhancer sequences have been identified, and may be useful in methods of the invention. See, e.g., U.S. Pat. No. 5,556,954; U.S. Patent App. 20020055144; U.S. Patent App. 20090148425.

2. Initiation Signals and Internal Ribosome Binding Sites

A specific initiation signal also may be used for efficient translation of coding sequences. These signals include the ATG initiation codon or adjacent sequences. Exogenous translational control signals, including the ATG initiation codon, may need to be provided. One of ordinary skill in the art would readily be capable of determining this and providing the necessary signals. It is well known that the initiation codon must be "in-frame" with the reading frame of the desired coding sequence to ensure translation of the entire insert. The exogenous translational control signals and initiation codons can be either natural or synthetic. The efficiency of expression may be enhanced by the inclusion of appropriate transcription enhancer elements.

In certain embodiments of the invention, the use of internal ribosome entry sites (IRES) elements are used to create multigene, or polycistronic, messages. IRES elements are able to bypass the ribosome scanning model of 5' methylated Cap dependent translation and begin translation at internal sites (Pelletier and Sonenberg, 1988). IRES elements from two members of the picornavirus family (polio and encephalomyocarditis) have been described (Pelletier and Sonenberg, 1988), as well an IRES from a mammalian message (Macejak and Sarnow, 1991). IRES elements can be linked to heterologous open reading frames. Multiple open reading frames can be transcribed together, each separated by an IRES, creating polycistronic messages. By virtue of the IRES element, each open reading frame is accessible to ribosomes for efficient translation. Multiple genes can be efficiently expressed using a single promoter/enhancer to transcribe a single message (see U.S. Pat. Nos. 5,925,565 and 5,935,819, each herein incorporated by reference).

3. Origins of Replication

In order to propagate a vector in a host cell, it may contain one or more origins of replication sites (often termed "ori"), for example, a nucleic acid sequence corresponding to oriP of EBV as described above or a genetically engineered oriP with a similar or elevated function in programming, which is a specific nucleic acid sequence at which replication is initiated. Alternatively a replication origin of other extrachromosomally replicating virus as described above or an autonomously replicating sequence (ARS) can be employed.

4. Selection and Screenable Markers

In certain embodiments of the invention, cells containing a nucleic acid construct of the present invention may be identified in vitro or in vivo by including a marker in the expression vector. Such markers would confer an identifiable change to the cell permitting easy identification of cells containing the expression vector. Generally, a selection marker is one that confers a property that allows for selection. A positive selection marker is one in which the presence of the marker allows for its selection, while a negative selection marker is one in which its presence prevents its selection. An example of a positive selection marker is a drug resistance marker.

Usually the inclusion of a drug selection marker aids in the cloning and identification of transformants, for example, genes that confer resistance to neomycin, puromycin, hygromycin, DHFR, GPT, zeocin and histidinol are useful selection markers. In addition to markers conferring a phenotype that allows for the discrimination of transformants based on the implementation of conditions, other types of markers including screenable markers such as GFP, whose basis is colorimetric analysis, are also contemplated. Alternatively, screenable enzymes as negative selection markers such as herpes simplex virus thymidine kinase (tk) or chloramphenicol acetyltransferase (CAT) may be utilized. One of skill in the art would also know how to employ immunologic markers, possibly in conjunction with FACS analysis. The marker used is not believed to be important, so long as it is capable of being expressed simultaneously with the nucleic acid encoding a gene product. Further examples of selection and screenable markers are well known to one of skill in the art. One feature of the present invention includes using selection and screenable markers to select for hematopoietic cells or precursors thereof after the programming factors have effected a desired programming change in those cells.

C. Nucleic Acid Delivery

Introduction of a nucleic acid, such as DNA or RNA, into cells to be programmed with the current invention may use any suitable methods for nucleic acid delivery for transformation of a cell, as described herein or as would be known to one of ordinary skill in the art. Such methods include, but are not limited to, direct delivery of DNA such as by ex vivo transfection (Wilson et al., 1989, Nabel et al, 1989), by injection (U.S. Pat. Nos. 5,994,624, 5,981,274, 5,945,100, 5,780,448, 5,736,524, 5,702,932, 5,656,610, 5,589,466 and 5,580,859, each incorporated herein by reference), including microinjection (Harland and Weintraub, 1985; U.S. Pat. No. 5,789,215, incorporated herein by reference); by electroporation (U.S. Pat. No. 5,384,253, incorporated herein by reference; Tur-Kaspa et al., 1986; Potter et al., 1984); by calcium phosphate precipitation (Graham and Van Der Eb, 1973; Chen and Okayama, 1987; Rippe et al., 1990); by using DEAE-dextran followed by polyethylene glycol (Gopal, 1985); by direct sonic loading (Fechheimer et al., 1987); by liposome mediated transfection (Nicolau and Sene, 1982; Fraley et al., 1979; Nicolau et al., 1987; Wong et al., 1980; Kaneda et al., 1989; Kato et al., 1991) and receptor-mediated transfection (Wu and Wu, 1987; Wu and Wu, 1988); by microprojectile bombardment (PCT Application Nos. WO 94/09699 and 95/06128; U.S. Pat. Nos. 5,610,042; 5,322, 783 5,563,055, 5,550,318, 5,538,877 and 5,538,880, and each incorporated herein by reference); by agitation with silicon carbide fibers (Kaeppler et al., 1990; U.S. Pat. Nos. 5,302,523 and 5,464,765, each incorporated herein by reference); by *Agrobacterium*-mediated transformation (U.S. Pat. Nos. 5,591,616 and 5,563,055, each incorporated herein by reference); by desiccation/inhibition-mediated DNA uptake (Potrykus et al., 1985), and any combination of such methods. Through the application of techniques such as these, organelle(s), cell(s), tissue(s) or organism(s) may be stably or transiently transformed.

1. Liposome-Mediated Transfection

In a certain embodiment of the invention, a nucleic acid may be entrapped in a lipid complex, such as, for example, a liposome. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, 1991). Also contemplated is a nucleic acid complexed with Lipofectamine (Gibco BRL) or Superfect (Qiagen). The amount of liposomes used may vary based upon the nature of the liposome as well as the cell used, for example, about 5 to about 20 µg vector DNA per 1 to 10 million of cells may be contemplated.

Liposome-mediated nucleic acid delivery and expression of foreign DNA in vitro has been very successful (Nicolau and Sene, 1982; Fraley et al., 1979; Nicolau et al., 1987). The feasibility of liposome-mediated delivery and expression of foreign DNA in cultured chick embryo, HeLa and hepatoma cells has also been demonstrated (Wong et al., 1980).

In certain embodiments of the invention, a liposome may be complexed with a hemagglutinating virus (HVJ). This has been shown to facilitate fusion with the cell membrane and promote cell entry of liposome-encapsulated DNA (Kaneda et al., 1989). In other embodiments, a liposome may be complexed or employed in conjunction with nuclear non-histone chromosomal proteins (HMG-1) (Kato et al., 1991). In yet further embodiments, a liposome may be complexed or employed in conjunction with both HVJ and HMG-1. In other embodiments, a delivery vehicle may comprise a ligand and a liposome.

2. Electroporation

In certain embodiments of the present invention, a nucleic acid is introduced into an organelle, a cell, a tissue or an organism via electroporation. Electroporation involves the exposure of a suspension of cells and DNA to a high-voltage electric discharge. Recipient cells can be made more susceptible to transformation by mechanical wounding. Also the amount of vectors used may vary upon the nature of the cells used, for example, about 5 to about 20 µg vector DNA per 1 to 10 million of cells may be contemplated.

Transfection of eukaryotic cells using electroporation has been quite successful. Mouse pre-B lymphocytes have been transfected with human kappa-immunoglobulin genes (Potter et al., 1984), and rat hepatocytes have been transfected with the chloramphenicol acetyltransferase gene (Tur-Kaspa et al., 1986) in this manner.

3. Calcium Phosphate

In other embodiments of the present invention, a nucleic acid is introduced to the cells using calcium phosphate precipitation. Human KB cells have been transfected with adenovirus 5 DNA (Graham and Van Der Eb, 1973) using this technique. Also in this manner, mouse L(A9), mouse C127, CHO, CV-1, BHK, NIH3T3 and HeLa cells were transfected with a neomycin marker gene (Chen and Okayama, 1987), and rat hepatocytes were transfected with a variety of marker genes (Rippe et al., 1990).

4. DEAE-Dextran

In another embodiment, a nucleic acid is delivered into a cell using DEAE-dextran followed by polyethylene glycol. In this manner, reporter plasmids were introduced into mouse myeloma and erythroleukemia cells (Gopal, 1985).

5. Sonication Loading

Additional embodiments of the present invention include the introduction of a nucleic acid by direct sonic loading. LTK⁻ fibroblasts have been transfected with the thymidine kinase gene by sonication loading (Fechheimer et al., 1987).

6. Microprojectile Bombardment

Microprojectile bombardment techniques can be used to introduce a nucleic acid into at least one, organelle, cell, tissue or organism (U.S. Pat. No. 5,550,318; U.S. Pat. No. 5,538,880; U.S. Pat. No. 5,610,042; and PCT Application WO 94/09699; each of which is incorporated herein by reference). This method depends on the ability to accelerate DNA-coated microprojectiles to a high velocity allowing them to pierce cell membranes and enter cells without killing them (Klein et al., 1987). There are a wide variety of microprojectile bombardment techniques known in the art, many of which are applicable to the invention.

In this microprojectile bombardment, one or more particles may be coated with at least one nucleic acid and delivered into cells by a propelling force. Several devices for accelerating small particles have been developed. One such device relies on a high voltage discharge to generate an electrical current, which in turn provides the motive force (Yang et al., 1990). The microprojectiles used have consisted of biologically inert substances such as tungsten or gold particles or beads. Exemplary particles include those comprised of tungsten, platinum, and preferably, gold. It is contemplated that in some instances DNA precipitation onto metal particles would not be necessary for DNA delivery to a recipient cell using microprojectile bombardment. However, it is contemplated that particles may contain DNA rather than be coated with DNA. DNA-coated particles may increase the level of DNA delivery via particle bombardment but are not, in and of themselves, necessary.

For the bombardment, cells in suspension are concentrated on filters or solid culture medium. Alternatively, immature embryos or other target cells may be arranged on solid culture medium. The cells to be bombarded are positioned at an appropriate distance below the macroprojectile stopping plate.

7. Transfection of mRNA

Gene delivery may also be achieved by transfection of mRNA, rather than DNA. In principle, unlike DNA transfection, introducing mRNA may have no permanent effect on the genetic structure of the cell, at least in the absence of rare reverse transcription events. Methods for transfecting mRNA are known in the art (see e.g., Seaboe-Larssen et al., 2002; Boczkowski et al., 2001; Elango et al., 2005; U.S. Patent App. 20080260706; U.S. Patent App. 20040235175).

B. Protein Transduction

In certain aspects of the present invention, the cells to be programmed into hematopoietic cells or hematopoietic precursor cells may be contacted with hematopoietic precursor programming factors comprising polypeptides of hematopoietic cell transcription factor genes at a sufficient amount for forward programming or transdifferentiation. Protein transduction has been used as a method for enhancing the delivery of macromolecules into cells. Protein transduction domains may be used to introduce hematopoietic precursor programming polypeptides or functional fragments thereof directly into cells. Research by many groups has shown that a region of the TAT protein which is derived from the HIV Tat protein can be fused to a target protein allowing the entry of the target protein into the cell. A particular exemplary protein sequence of this domain is RKKRRQRRR (SEQ ID NO:19) where R encodes Arginine, K encodes Lysine and Q encodes Glutamine. This sequence has been shown to enable the entry of a protein fusion both as an N-terminal or C-terminal fusion. The mechanism of TAT mediated entry is thought to be by macropinocytosis (Gump and Dowdy).

A "protein transduction domain" or "PTD" is an amino acid sequence that can cross a biological membrane, particularly a cell membrane. When attached to a heterologous polypeptide, a PTD can enhance the translocation of the heterologous polypeptide across a biological membrane. The PTD is typically covalently attached (e.g., by a peptide bond) to the heterologous DNA binding domain. For example, the PTD and the heterologous DNA binding domain can be encoded by a single nucleic acid, e.g., in a common open reading frame or in one or more exons of a common gene. An exemplary PTD can include between 10-30 amino acids and may form an amphipathic helix. Many PTDs are basic in character. For example, a basic PTD can include at least 4, 5, 6 or 8 basic residues (e.g., arginine or lysine). A PTD may be able to enhance the translocation of a polypeptide into a cell that lacks a cell wall or a cell from a particular species, e.g., a mammalian cell, such as a human, simian, murine, bovine, equine, feline, or ovine cell.

A PTD can be linked to an artificial transcription factor, for example, using a flexible linker. Flexible linkers can include one or more glycine residues to allow for free rotation. For example, the PTD can be spaced from a DNA binding domain of the transcription factor by at least 10, 20, or 50 amino acids. A PTD can be located N- or C-terminal relative to a DNA binding domain. Being located N- or C-terminal to a particular domain does not require being adjacent to that particular domain. For example, a PTD N-terminal to a DNA binding domain can be separated from the DNA binding domain by a spacer and/or other types of domains. A PTD can be chemically synthesized then conjugated chemically to a separately prepared DNA binding domain with or without a linker peptide. An artificial transcription factor can also include a plurality of PTDs, e.g., a plurality of different PTDs or at least two copies of one PTD.

Several proteins and small peptides have the ability to transduce or travel through biological membranes independent of classical receptor- or endocytosis-mediated pathways. Examples of these proteins include the HIV-1 TAT protein, the herpes simplex virus 1 (HSV-1) DNA-binding protein VP22, and the *Drosophila* Antennapedia (Antp) homeotic transcription factor. The small protein transduction domains (PTDs) from these proteins can be fused to other macromolecules, peptides, or proteins to successfully transport them into a cell. Sequence alignments of the transduction domains from these proteins show a high basic amino acid content (Lys and Arg) which may facilitate interaction of these regions with negatively charged lipids in the membrane. Secondary structure analyses show no consistent structure between all three domains.

The advantages of using fusions of these transduction domains is that protein entry is rapid, concentration-dependent, and appears to work with difficult cell types.

The Tat protein from human immunodeficiency virus type I (HIV-1) has the remarkable capacity to enter cells when added exogenously (Frankel and Pabo, 1988; Mann and Frankel, 1991; Fawell et al., 1994). A particular example of a Tat PTD may include residues 47-57 of the human immunodeficiency virus Tat protein: YGRKKRRQRRR (SEQ ID NO:20). This peptide sequence is referred to as "TAT" herein. This peptide has been shown to successfully mediate the introduction of heterologous peptides and proteins in excess of 100 kDa into mammalian cells in vitro and in vivo (Ho et al., 2001). Schwarze et al. showed that when the 120 kDa β-galactosidase protein fused with TAT was injected into mouse intraperitoneally, the fusion proteins were found in all types of cells and tissues even including brain, which has been thought to be difficult because of the blood-brain-barrier (Schwarze et al., 1999).

The antennapedia homeodomain also includes a peptide that is a PTD (Derossi et al., 1994). This peptide, also referred to as "Penetratin", includes the amino acid sequence: AKIWFQNRRMKWKKENN (SEQ ID NO:21).

The HSV VP22 protein also includes a PTD. This PTD is located at the VP22 C-terminal 34 amino acid residues: DAATATRGRSAASRPTERPRAPARSASRPRRPVE (SEQ ID NO:22). See, e.g., Elliott and O'Hare (1997) and U.S. Pat. No. 6,184,038.

In one embodiment, the PTD is obtained from a human or other mammalian protein. Exemplary mammalian PTDs are described in WO 03/059940 (human SIM-2) and WO 03/059941 (Mph). In certain embodiments, the PTD could be a synthetic PTD. The minimal Tat PTD (aa 47-57) was modified to optimize protein transduction potential (Ho et al., 2001). A FITC coupled with series of synthetic PTDs was tested with cultured T lymphocytes. Some synthetic PTDs showed enhanced protein transduction compared to Tat PTD. These PTD include: YARKARRQARR (SEQ ID NO:23); YARAARRAARR (SEQ ID NO:24); YARAAR-RAARA (SEQ ID NO:25); YARAAARQARA (SEQ ID NO:26). Especially, the FITC conjugated with synthetic PTD YARAAARQARA (SEQ ID NO:26); showed enhanced uptake by whole blood cells when the mice were i.p. injected.

The poly-arginine peptides composed of about 6-12 arginine residues also can mediate protein transduction in some cases. For additional information about poly-arginine, see, e.g., Rothbard et al. (2000); Wender et al. (2000).

For additional information about PTDs, see also U.S. 2003/0082561; U.S. 2002/0102265; U.S. 2003/0040038; Schwarze et al. (1999); Derossi et al. (1996); Hancock et al. (1991); Buss et al. (1988); Derossi et al. (1998); Lindgren et al. (2000); Kilic et al. (2003); Asoh et al. (2002); and Tanaka et al. (2003).

In addition to PTDs, cellular uptake signals can be used. Such signals include amino acid sequences that are specifically recognized by cellular receptors or other surface proteins. Interaction between the cellular uptake signal and the cell causes internalization of the artificial transcription factor that includes the cellular uptake signal. Some PTDs may also function by interaction with cellular receptors or other surface proteins.

A number of assays are available to determine if an amino acid sequence can function as a PTD. For example, the amino acid sequence can be fused to a reporter protein such as β-galactosidase to form a fusion protein. This fusion protein is contacted with culture cells. The cells are washed and then assayed for reporter activity. Another assay detects the presence of a fusion protein that includes the amino acid sequence in question and another detectable sequence, e.g., an epitope tag. This fusion protein is contacted with culture cells. The cells are washed and then analyzed by Western or immunofluorescence to detect presence of the detectable sequence in cells. Still other assays can be used to detect transcriptional regulatory activity of a fusion protein that includes the putative PTD, a DNA binding domain, and optionally an effector domain. For example, cells contacted with such fusion proteins can be assayed for the presence or amount of mRNA or protein, e.g., using microarrays, mass spectroscopy, and high-throughput techniques.

V. CELL CULTURING

Generally, cells of the present invention are cultured in a culture medium, which is a nutrient-rich buffered solution capable of sustaining cell growth.

Culture media suitable for isolating, expanding and differentiating stem cells into hematopoietic precursor cells and hematopoietic cells according to the method described herein include but not limited to high glucose Dulbecco's Modified Eagle's Medium (DMEM), DMEM/F-15, Liebovitz L-15, RPMI 1640, Iscove's modified Dubelcco's media (IMDM), and Opti-MEM SFM (Invitrogen Inc.). Chemically Defined Medium comprises a minimum essential medium such as Iscove's Modified Dulbecco's Medium (IMDM) (Gibco), supplemented with human serum albumin, human Ex Cyte lipoprotein, transferrin, insulin, vitamins, essential and non essential amino acids, sodium pyruvate, glutamine and a mitogen is also suitable. As used herein, a mitogen refers to an agent that stimulates division of a cell. An agent can be a chemical, usually some form of a protein that encourages a cell to commence cell division, triggering mitosis. In one embodiment, serum free media such as those described in U.S. Ser. No. 08/464,599 and WO96/39487, and the "complete media" as described in U.S. Pat. No. 5,486,359 are contemplated for use with methods described herein. In some embodiments, the culture medium is supplemented with 10% Fetal Bovine Serum (FBS), human autologous serum, human AB serum or platelet rich plasma supplemented with heparin (2 U/ml). Cell cultures may be maintained in a $CO_2$ atmosphere, e.g., 5% to 12%, to maintain pH of the culture fluid, incubated at 37° C. in a humid atmosphere and passaged to maintain a confluence below 85%.

Pluripotent stem cells to be differentiated into hematopoietic cells and their precursors may be cultured in a medium sufficient to maintain the pluripotency. Culturing of induced pluripotent stem (iPS) cells generated in certain aspects of this invention can use various media and techniques developed to culture primate pluripotent stem cells, more specially, embryonic stem cells, as described in U.S. Pat. App. 20070238170 and U.S. Pat. App. 20030211603. For example, like human embryonic stem (hES) cells, iPS cells can be maintained in 80% DMEM/F12 (Gibco #11330032 or #11320082), 20% KnockOut serum replacement, 1% non-essential amino acids, 1 mM L-glutamine, 0.1 mM β-mercaptoethanol, and bFGF (4-100 ng/mL) (PCT Appln. WO 99/20741). Alternatively, human ES cells and iPS cells can be maintained in chemically defined serum-free medium, such as mTeSR1.

Hematopoietic cells and their precursors can be generated by culturing pluripotent stem cells or other non-hematopoietic cells in a medium under conditions that increase the intracellular level of hematopoietic cell and/or hematopoietic precursor programming factors to be sufficient to promote programming of the cells into hematopoietic cells or their precursors. The medium may also contain one or more hematopoietic cell differentiation and maturation agents, like various kinds of growth factors. However, by increasing the intracellular level of hematopoietic cell and/or hematopoietic precursor programming transcription factors, aspects of the present invention bypass most stages toward hematopoietic precursor cells and hematopoietic cells without the need to change the medium for each of the stages. Therefore, in view of the advantages provided by the present invention, in particular aspects, the medium for culturing cells under hematopoietic programming may be essentially free of one or more of the hematopoietic cell and hematopoietic precursor differentiation and maturation agents, or may not undergo serial change with media containing different combinations of such agents.

These agents may either help induce cells to commit to a more mature phenotype—or preferentially promote survival of the mature cells—or have a combination of both these effects. Hematopoietic precursor cell and hematopoietic cell differentiation and maturation agents illustrated in this disclosure may include soluble growth factors (peptide hormones, cytokines, ligand-receptor complexes, and other compounds) that are capable of promoting the growth of cells of the hematopoietic cell lineage. Non-limiting examples of such agents include but are not limited to hematopoietic or endothelial growth factors such as fibroblast growth factor (FGF), vascular endothelial growth factor (VEGF), stem cell factor (SCF), thrombopoietin (TPO), FLT-3 ligand (FLT3L), interleukin-3 (IL-3), interleukin-6 (IL-6), interleukin-9 (IL-9), or granulocyte colony-stimulating factor (G-CSF), or isoforms or variants thereof.

VI. HEMATOPOIETIC PRECURSOR AND HEMATOPOIETIC CELL CHARACTERISTICS

Cells can be characterized according to a number of phenotypic criteria. The criteria include but are not limited to the detection or quantitation of expressed cell markers, functional activity, and the characterization of morphological features and intercellular signaling. In other aspects, cells to be programmed may comprise a reporter gene expression cassette comprising tissue- or cell-specific transcriptional regulatory elements, like hematopoietic cell-specific promoters for hematopoietic cell identification.

Hematopoietic precursor cells embodied in certain aspects of this invention have morphological features characteristic of hematopoietic precursor cells in nature. The features are readily appreciated by those skilled in evaluating such things, and include the detection of cell clusters producing round non-adherent cells. In addition, hematopoietic precursor cells have a rounded shape and a low cytoplasm-to-nucleus ratio.

Cells of this invention can also be characterized according to whether they express certain markers characteristic of cells of the hematopoietic cell lineage. Non-limiting examples of cell markers useful in distinguishing hematopoietic cells and precursors of hematopoietic cells include: CD43, CD33, CD34, CD45, CD235a, CD38, CD90, CD133, CD105, CD117 (c-kit; the receptor for SCF), CD74, and CD41a. To identify cells that have differentiated from multipotent starting cells, such as ESCs or iPSCs, it may be useful to identify cells that do not express certain markers that are present on pluripotent stem cells or somatic cells, such as TRA-1-60, TRA-1-81, CD166, or CD140b. To identify cells that have transdifferentiated from somatic cells to hematopoietic cells or hematopoietic precursor cells, it may be useful to determine whether the transdifferentiated cells express certain markers characteristic of hematopoietic cells, such as those listed above, and do not express non-hematopoietic markers that are expressed by the somatic cells that have not undergone programming.

Assessment of the level of expression of such markers can be determined in comparison with other cells. Positive controls for the markers of hematopoietic precursor cells or hematopoietic cells include adult hematopoietic cells or hematopoietic stem cells of the species of interest, and established hematopoietic cell lines. The reader is cautioned that permanent cell lines or long-term hematopoietic cells cultures may be metabolically altered, and fail to express certain characteristics of primary hematopoietic cells and hematopoietic precursor cells. Negative controls include cells of a separate lineage, such as an adult fibroblast cell line, adult mesenchymal stem cells, or retinal pigment epithelial (RPE) cells. Undifferentiated stem cells are positive for some of the markers listed above, but negative for certain markers of hematopoietic cells and hematopoietic precursor cells, as illustrated in the examples below.

Hematopoietic-specific protein and oligosaccharide determinants listed in this disclosure can be detected using any suitable immunological technique—such as flow immunocytochemistry for cell-surface markers, immunohistochemistry (for example, of fixed cells or tissue sections) for intracellular or cell-surface markers, Western blot analysis of cellular extracts, and enzyme-linked immunoassay, for cellular extracts or products secreted into the medium. Expression of an antigen by a cell is said to be "antibody-detectable" if a significantly detectable amount of antibody will bind to the antigen in a standard immunocytochemistry or flow cytometry assay, optionally after fixation of the cells, and optionally using a labeled secondary antibody or other conjugate (such as a biotin-avidin conjugate) to amplify labeling.

The expression of specific (e.g., hematopoietic precursor cell-specific) markers can also be detected at the mRNA level by Northern blot analysis, dot-blot hybridization analysis, or by real time polymerase chain reaction (RT-PCR) using sequence-specific primers in standard amplification methods (U.S. Pat. No. 5,843,780). Sequence data for the particular markers listed in this disclosure can be obtained from public databases such as GenBank. Expression at the mRNA level is said to be "detectable" according to one of the assays described in this disclosure if the performance of the assay on cell samples according to standard procedures in a typical controlled experiment results in clearly discernable hybridization or amplification product within a standard time window. Unless otherwise required, expression of a particular marker is indicated if the corresponding mRNA is detectable by RT-PCR. Expression of specific markers as detected at the protein or mRNA level is considered positive if the level is at least 2-fold, and preferably more than 10- or 50-fold above that of a control cell, such as an undifferentiated pluripotent stem cell, a fibroblast, or other unrelated cell type.

Cells can also be characterized according to whether they display a functional activity that is characteristic of cells of the hematopoietic lineage. For example, hematopoietic precursor cells have the ability to self-renew and can give rise to more than one type of hematopoietic cell. In particular embodiments, the hematopoietic precursor cells obtained can give rise to lymphoid cells (such as, for example, T cells, B cells, and NK cells), erythro-megakaryocytic cells (such as, for example, erythrocytes and thrombocytes), and myeloid cells (such as, for example, granulocytes and monocytes) in vitro, and are capable of long-term engraftment in immunodeficient mice.

The skilled reader will readily appreciate that an advantage of programming-derived hematopoietic precursor cells and hematopoietic cells is that they will be essentially free of other cell types that may typically contaminate primary cultures of hematopoietic cells and hematopoietic precursor cells isolated from adult or fetal tissue, such as stromal cells and non-hematopoietic cells of mesodermal origin. Programming-derived hematopoietic cells and precursors thereof can be characterized as essentially free of some or all of contaminant cell types if less than 0.1% (preferably less than 100 or 10 ppm) bear markers or other features of the undesired cell type, as determined by immunostaining and fluorescence-activated quantitation, or other appropriate techniques.

Hematopoietic precursor cells and hematopoietic cells provided by programming according to this invention can have a number of the features of the stage of cell they are intended to represent. The more of these features that are present in a particular cell, the more it can be characterized as a cell of the hematopoietic cell lineage. Cells having at least 2, 3, 5, 7, or 9 of these features are increasingly more preferred. In reference to a particular cell population as may be present in a culture vessel or a preparation for administration, uniformity between cells in the expression of these features is often advantageous. In this circumstance, populations in which at least about 40%, 60%, 80%, 90%, 95%, or 98% of the cells have the desired features are increasingly more preferred.

VII. USES OF HEMATOPOIETIC CELLS AND PRECURSORS THEREOF

The hematopoietic cells and hematopoietic precursor cells provided by methods and compositions of certain aspects of the invention can be used in a variety of applications. These include but are not limited to transplantation or implantation of the hematopoietic cells and hematopoietic precursor in vivo; screening cytotoxic compounds, carcinogens, mutagens growth/regulatory factors, pharmaceutical compounds, etc., in vitro; elucidating the mechanism of hematological diseases and injuries; studying the mechanism by which drugs and/or growth factors operate; diagnosing and monitoring cancer in a patient; gene therapy; and the production of biologically active products, to name but a few.

A. Test Compound Screening

Programming-derived hematopoietic and hematopoietic precursor cells of this invention can be used to screen for factors (such as solvents, small molecule drugs, peptides, and polynucleotides) or environmental conditions (such as culture conditions or manipulation) that affect the characteristics of hematopoietic cells provided herein.

In some applications, stem cells (differentiated or undifferentiated) are used to screen factors that promote maturation of cells along the hematopoietic cell lineage, or promote proliferation and maintenance of such cells in long-term culture. For example, candidate hematopoietic cell maturation factors or growth factors are tested by adding them to stem cells in different wells, and then determining any phenotypic change that results, according to desirable criteria for further culture and use of the cells.

Particular screening applications of this invention relate to the testing of pharmaceutical compounds in drug research. The reader is referred generally to the standard textbook *In vitro Methods in Pharmaceutical Research*, Academic Press, 1997, and U.S. Pat. No. 5,030,015). In certain aspects of this invention, cells programmed to the hematopoietic lineage play the role of test cells for standard drug screening and toxicity assays, as have been previously performed on hematopoietic cells and precursors in short-term culture. Assessment of the activity of candidate pharmaceutical compounds generally involves combining the hematopoietic cells or precursors provided in certain aspects of this invention with the candidate compound, determining any change in the morphology, marker phenotype, or metabolic activity of the cells that is attributable to the compound (compared with untreated cells or cells treated with an inert compound), and then correlating the effect of the compound with the observed change. The screening may be done either because the compound is designed to have a pharmacological effect on hematopoietic cells or precursors, or because a compound designed to have effects elsewhere may have unintended effects on hematopoietic cells or precursors. Two or more drugs can be tested in combination (by combining with the cells either simultaneously or sequentially), to detect possible drug-drug interaction effects.

In some applications, compounds may be screened for toxicity to hematopoietic cells or hematopoietic precursor cells.

B. Hematopoietic Cell Therapy

This invention also provides for the use of hematopoietic cells and hematopoietic precursor cells provided herein to restore a degree of function to a subject needing such therapy, perhaps due to a hematological disease or disorder or an injury. For example, hematopoietic cells and hematopoietic precursor cells derived by methods disclosed herein may be used to treat hematological diseases and disorders such as hemoglobinopathies, anemias, etc. In addition, hematopoietic cells and their precursors may be useful in supplying blood or blood cells (such as, for example, red blood cells, platelets, and neutrophil granulocytes) to subjects in need thereof (such as, for example, subjects in need of a blood transfusion or subjects having a hematological disorder). Such cells may be useful for the treatment of hematopoietic cell deficiencies caused by cell-suppressive therapies, such as chemotherapy.

To determine the suitability of hematopoietic cells and precursors provided herein for therapeutic applications, the cells can first be tested in a suitable animal model. At one level, cells are assessed for their ability to survive and maintain their phenotype in vivo. Programmed cells provided herein are administered to immunodeficient animals (such as NOG mice, or animals rendered immunodeficient chemically or by irradiation) at a site amenable for further observation, such as under the kidney capsule, into the spleen, into a liver lobule, or into the bone marrow. Tissues are harvested after a period of a few days to several weeks or more, and assessed as to whether starting cell types such as pluripotent stem cells are still present. This can be performed by providing the administered cells with a detectable label (such as green fluorescent protein, or β-galactosidase); or by measuring a constitutive marker specific for the administered human cells. Where programmed cells provided herein are being tested in a rodent model, the presence and phenotype of the administered cells can be assessed by immunohistochemistry or ELISA using human-specific antibody, or by RT-PCR analysis using primers and hybridization conditions that cause amplification to be specific for human polynucleotide sequences. Suitable markers for assessing gene expression at the mRNA or protein level are provided elsewhere in this disclosure.

Hematopoietic cells and hematopoietic precursor provided by methods of the invention may be tested in various animal models for their ability to treat hematological disorders and injuries. For example, a sickle cell anemia mouse model or the T/B cell-deficient Rag-2 knockout mouse may be particularly useful animal models for testing the hematopoietic cells and hematopoietic precursors disclosed herein.

Hematopoietic cells and hematopoietic precursor cells provided in certain aspects of this invention that demonstrate desirable functional characteristics or efficacy in animal models, may also be suitable for direct administration to human subjects in need thereof. For purposes of hemostasis, the cells can be administered at any site that has adequate access to the circulation. Hematopoietic cells or precursors thereof may also be delivered at a site of injury or disease.

The cells provided in certain aspects of this invention can be used for therapy of any subject in need thereof. Human conditions that may be appropriate for such therapy include the various anemias and hemoglobinopathies, as well as diseases characterized by decreased numbers of hematopoietic cells (such as, for example, myelodysplastic syndrome, myelofibrosis, neutropenia, agranulocytosis, Glanzmann's thrombasthenia, thrombocytopenia, and acquired immune deficiency syndrome). For human therapy, the dose is generally between about $10^9$ and $10^{12}$ cells, and typically between about $5 \times 10^9$ and $5 \times 10^{10}$ cells, making adjustments for the body weight of the subject, nature and severity of the affliction, and the replicative capacity of the administered cells. The ultimate responsibility for determining the mode of treatment and the appropriate dose lies with the managing clinician.

C. Distribution for Commercial, Therapeutic, and Research Purposes

For purposes of manufacture, distribution, and use, the hematopoietic lineage cells of this invention are typically supplied in the form of a cell culture or suspension in an isotonic excipient or culture medium, optionally frozen to facilitate transportation or storage.

This invention also includes different reagent systems, comprising a set or combination of cells that exist at any time during manufacture, distribution, or use. The cell sets comprise any combination of two or more cell populations described in this disclosure, exemplified but not limited to programming-derived cells (hematopoietic lineage cells, their precursors and subtypes), in combination with undifferentiated stem cells, somatic cell-derived hematopoietic cells, or other differentiated cell types. The cell populations in the set sometimes share the same genome or a genetically modified form thereof. Each cell type in the set may be packaged together, or in separate containers in the same facility, or at different locations, at the same or different times, under control of the same entity or different entities sharing a business relationship.

VIII. CELLS AND METHODS FOR TESTING CANDIDATE GENE IN PROGRAMMING

The ability of a particular candidate gene or a combination of candidate genes to act as programming factors for a specific cell type, such as hematopoietic precursor cells, can be tested using the methods and cells provided in this disclosure. Efficacy of particular candidate genes or combinations of candidate genes in programming can be assessed by their effect on cell morphology, marker expression, enzymatic activity, proliferative capacity, or other features of interest, which is then determined in comparison with parallel cultures that did not include the candidate genes or combinations. Candidate genes may be transcription factors important for differentiation into desired cell types or for function of the desired cell types.

In certain embodiments, starting cells, such as pluripotent stem cells, comprising at least one expression cassette for expression of a candidate gene or a combination of candidate genes may be provided. The expression cassette may comprise an externally controllable transcriptional regulatory element, such as an inducible promoter. The activity of these promoters may be induced by the presence or absence of biotic or abiotic factors. Inducible promoters are a very powerful tool in genetic engineering because the expression of genes operably linked to them can be turned on or off at certain stages of development of an organism or in a particular tissue. Tet-On and Tet-Off inducible gene expression systems based on the essential regulatory components of the *E. coli* tetracycline-resistance operon may be used.

Once established in the starting cells, the inducer doxycycline (Dox, a tetracycline derivative) could controls the expression system in a dose-dependent manner, allowing to precisely modulate the expression levels of candidate genes.

To aid identification of desired cell types, the starting cells may further comprise a cell-specific or tissue-specific reporter expression cassette. The reporter expression cassette may comprise a reporter gene operably linked to a transcriptional regulatory element specific for the desired cell types. For example, the reporter expression cassette may comprise a hematopoietic cell-specific promoter for hematopoietic cell or hematopoietic precursor cell production, isolation, selection, or enrichment. The reporter gene may be any selectable or screenable marker gene known in the art and exemplified in the preceding disclosure.

VIII. EXAMPLES

The following examples are included to demonstrate preferred embodiments of the invention. It should be appreciated by those of skill in the art that the techniques disclosed in the examples that follow represent techniques discovered by the inventors to function well in the practice of the invention, and thus can be considered to constitute preferred modes for its practice. However, those of skill in the art should, in light of the present disclosure, appreciate that many changes can be made in the specific embodiments that are disclosed and still obtain a like or similar result without departing from the spirit and scope of the invention.

Example 1

Forward Programming into Hematopoietic Precursor Cells

Alternative approaches for hematopoietic precursor cell differentiation from human ESCs/iPSCs are shown in FIG. 1. Hematopoietic precursor cells can be efficiently induced from human ESCs/iPSCs via expression of an appropriate transgene or transgene combination (top box), bypassing most, if not all, developmental stages required during normal differentiation (bottom box).

Figure 2:
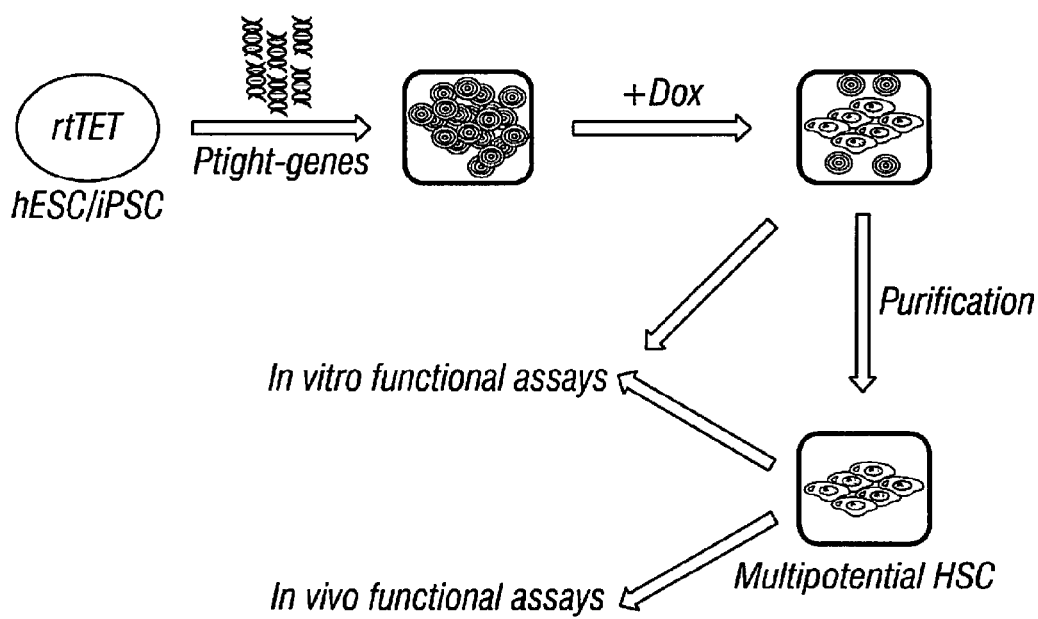
FIG. 2. The strategy employed for identifying transgene/s that could directly convert human ESCs/iPSCs to hematopoietic cells via forward programming.

The Strategy Employed for Identifying Transgenes that could Directly Convert Human ESCs/iPSCs to Hematopoietic Precursor Cells (FIG. 2).

Human ESCs/iPSCs were engineered to constitutively express rtTET protein for inducible gene expression. Transgenes under the control of the inducible promoter (Ptight) were introduced into the engineered human ESCs/iPSCs by electroporation. Upon Doxycycline (Dox) addition, transgene expression was induced, and hematopoietic differentiation was monitored by the characteristic hematopoietic cell morphology (e.g., cell clusters producing round nonadherent cells), flow cytometric detection of total hematopoietic precursor cell population by expression of the early pan-hematopoietic marker CD43 along with subpopulations of committed EMk (CD43+CD235a+CD41a+) and lineage negative (Lin−) CD43+CD45−/+ multipotent hematopoietic precursors (Vodyanik et al. 2006). Lin− cells are negative for a set of lineage-specific markers such as CD235a (erythroid), CD41a (megakaryocytic), CD11b, CD33 (myeloid), CD19, CD3, and CD2 (lymphoid), and are multipotent and not committed to any lineage (Vodyanik et al., 2006; U.S. Patent App. 20070072295). The Lin−CD43+ CD45−/+ cells are said to be "CD45−/+" because the multipotent cells are initially CD45− but then acquire CD45 expression to become CD45+. Thus, during early induction, CD43+Lin− multipotent cells may be CD45− or CD45+. Different types of hematopoietic precursors were also determined by a colony-forming assay.

Figure 3:
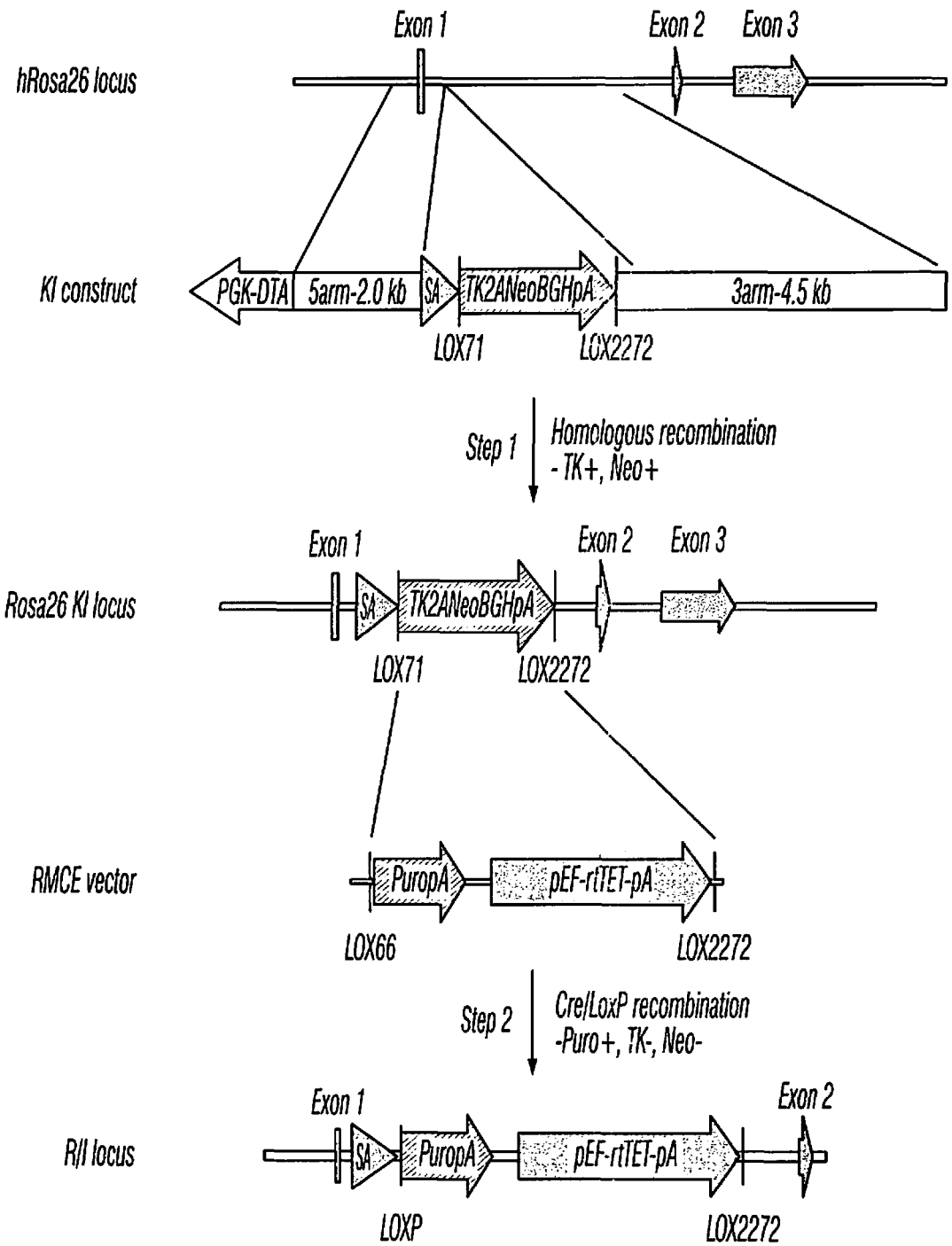
FIG. 3. The establishment of human ESC/iPSC inducible (R/I) lines for heinalopoielic differentiation.

The Establishment of Human ESC/iPSC Inducible (R/I) Lines for Hematopoietic Precursor Cell Differentiation (FIG. 3).

The human Rosa26 locus on chromosome 3 was selected to allow the expression of rtTET. First, the LoxP recombination sites (LOX71 and LOX2272) were introduced into the first intron of the human ROSA26 gene via homologous recombination. The targeting construct (KI construct) used the phosphoglycerate kinase promoter (PGK)-driven expression of diphtheria toxin A fragment gene (DTA) for negative selection and contains a ~2.0 kb 5' arm and a 4.5 kb 3' arm. A splicing acceptor signal from the human BCL2 gene (SA) was placed in front of the LOX71 site to allow the expression of selection markers from the endogenous human ROSA26 promoter. The coding region for thymidine kinase (TK) was included to enable negative selection against incorrect Cre/LoxP recombination events at step 2 using ganciclovir. The neomycin phosphotransferase (Neo) was used for positive selection during homologous recombination in step 1. The foot-and-mouth disease virus peptide (2A) was used to co-express the TK and Neo genes from the endogenous human ROSA26 promoter. BGHpA is a polyadenylation signal derived from the bovine growth hormone gene. Homologous recombination yielded parental human ESC/iPSC lines for efficient cassette exchange via Cre/LoxP recombination. To establish inducible cell lines for hematopoietic differentiation, rtTET driven by the constitutively active eukaryotic elongation factor 1α promoter (pEF) was introduced into the ROSA26 locus by lipid-mediated cotransfection of the recombination mediated cassette exchange (RMCE) vector and a Cre-expressing plasmid. The puromycin N-acetyl-transferase (Puro) was used to select for recombination events. The correctly recombined inducible cells are resistant to puromycin (Puro+) and ganciclovir (TK−), and are sensitive to geneticin selection (Neo−).

Confirmation of the Tet-on Inducible Gene Expression in Human H1 ESC Inducible Lines (FIG. 4).

Figure 4A:
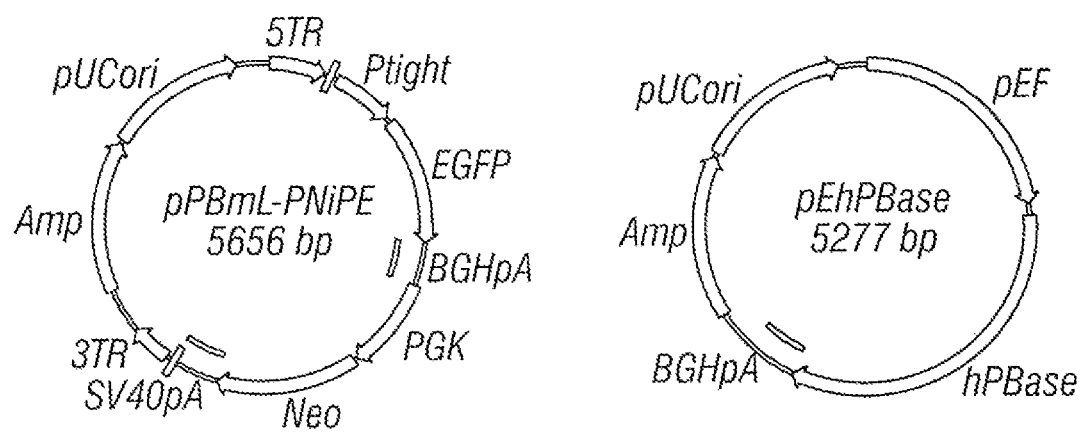
FIGS. 4A, 4B, 4C. Confirmation of the Tet-On inducible gene expression in human H1 ESC inducible lines.
Figure 4B:
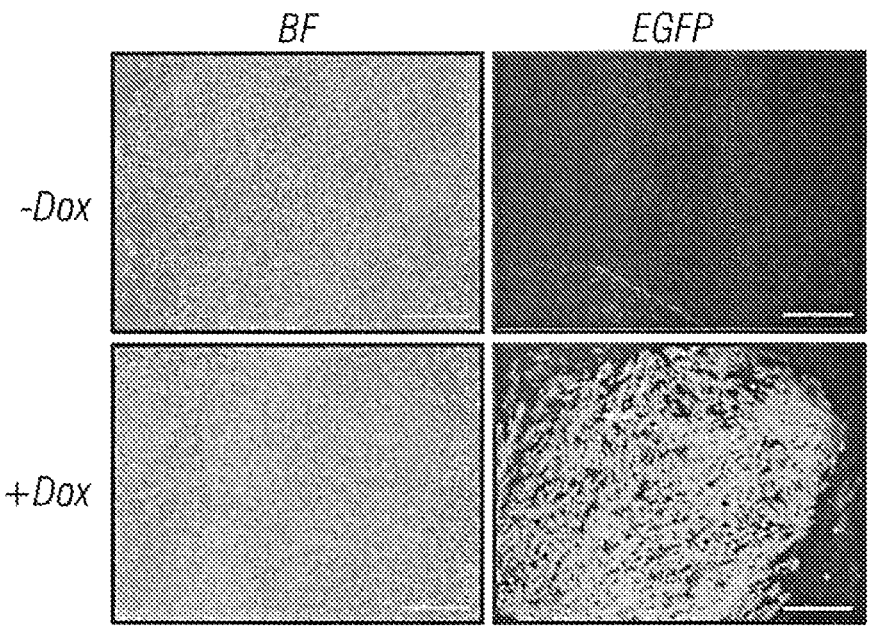
Figure 4C:
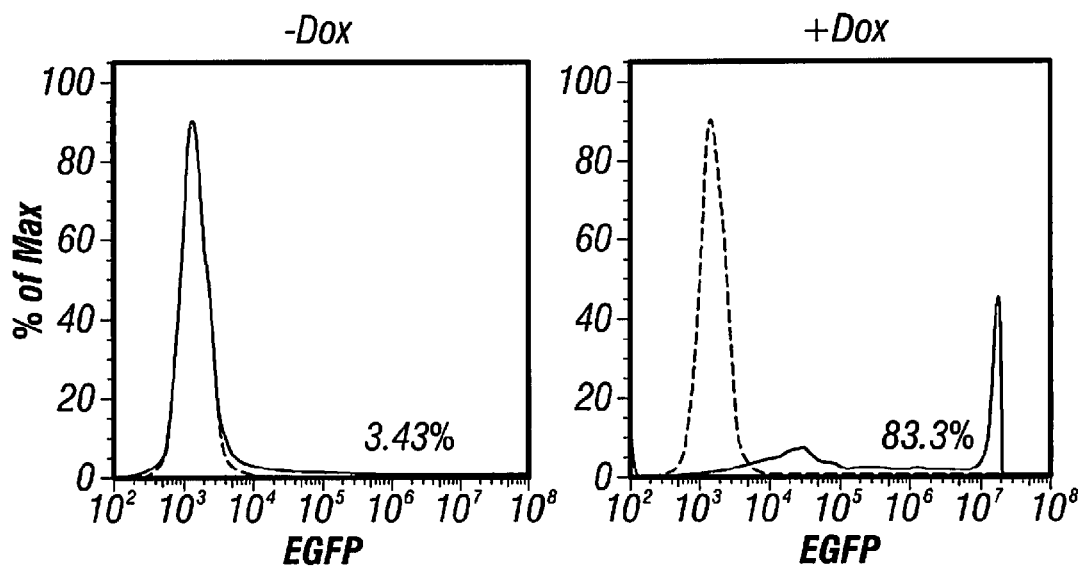

FIG. 4A shows a two-vector PiggyBac transposon gene expression system. Ptight is an rtTET-responsive inducible promoter; pEF is the eukaryotic elongation factor 1α promoter; hPBase is the coding region for the PiggyBac transposase with codons optimized for expression in human cells. FIG. 4B shows EGFP induction in human ESC inducible lines. EGFP driven by the Ptight promoter was introduced into human ESC inducible lines using Fugene HD-mediated transfection of the vectors shown in FIG. 4A. Human ESCs with stable PiggyBac transposon integration were selected with geneticin (100 μg/ml). Images are shown of human ESC inducible lines after 2 days induction with or without Doxycycline (1 μg/ml). FIG. 4C shows flow cytometric analysis of EGFP expression in human ESC inducible lines after 4 days induction with or without Doxycycline (1 μg/ml). Gray lines are human ESC inducible lines without transfection of the EGFP vector; black lines are human ESC R/I lines with stable PiggyBac transposon integration after 4 days induction with or without Doxycycline.

Figure 5A:
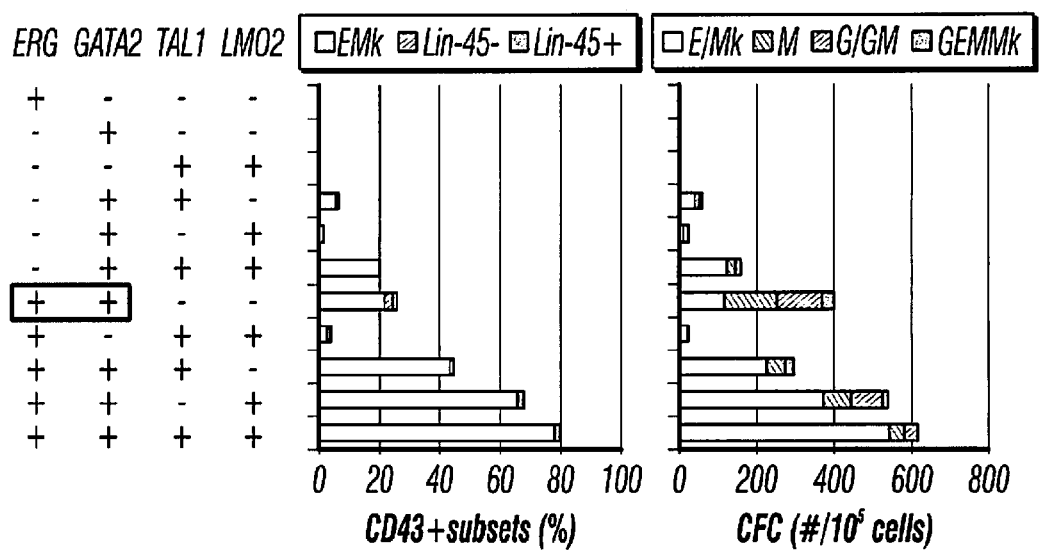
Figure 5C:
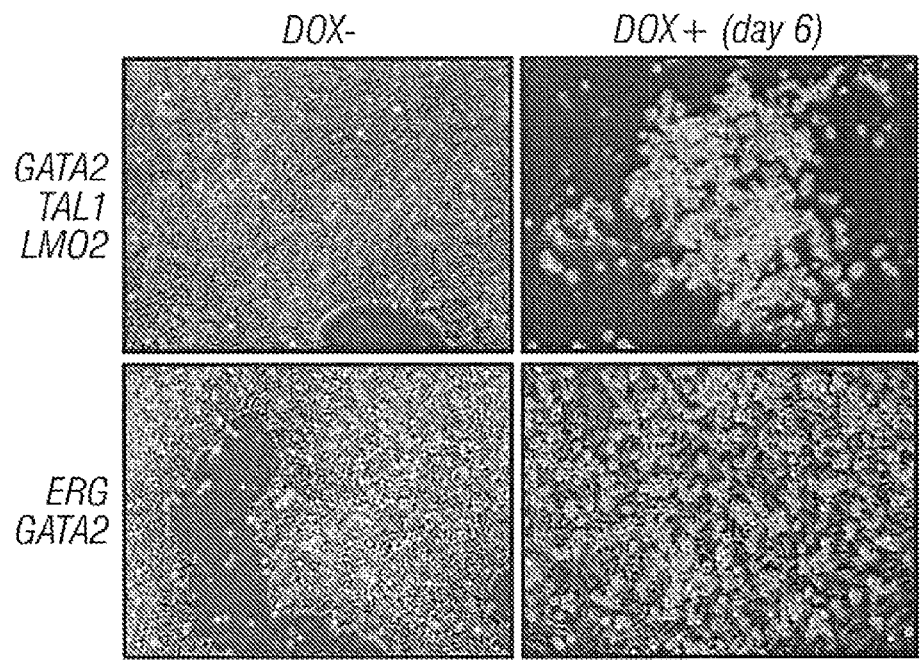
Figure 5C:
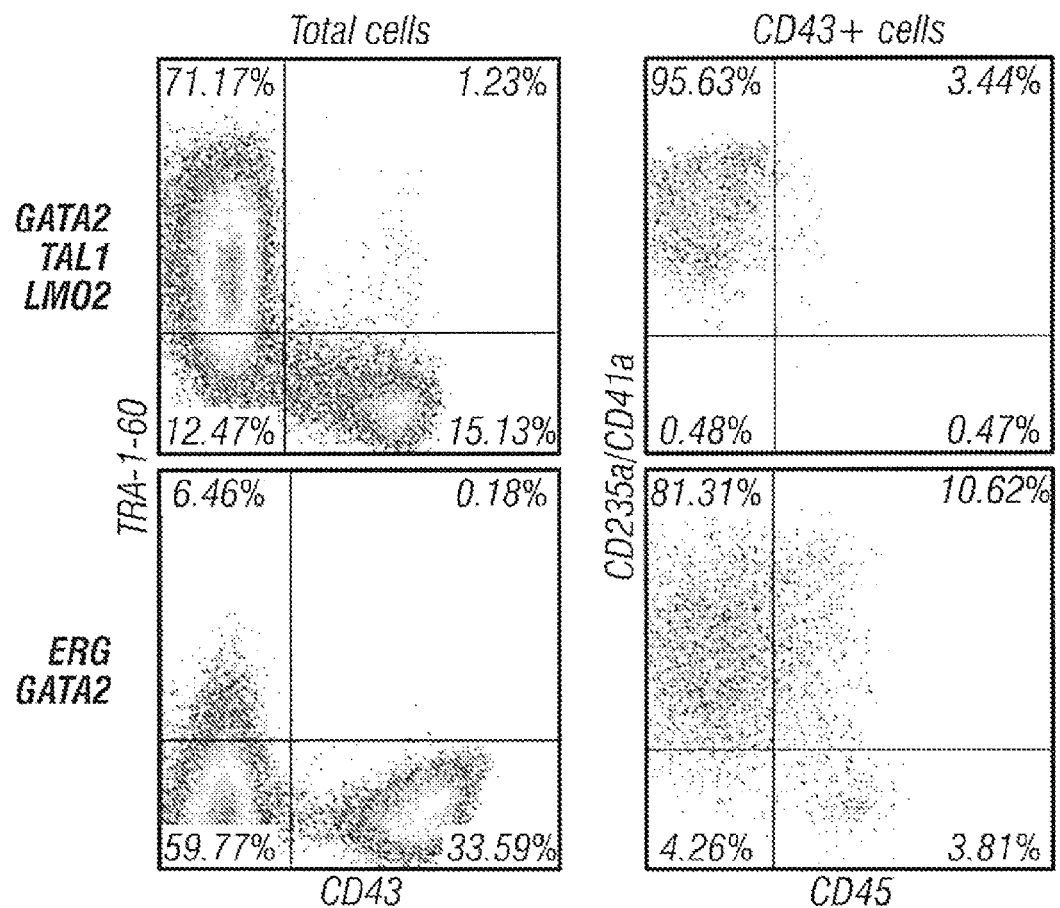

Forward Programming of Hematopoietic Precursor Cells from Human Embryonic Stem Cell (ESC) Inducible Lines Through ERG-3 and GATA2 Expression (FIG. 5).

The coding regions of genes selectively expressed or enriched in cells of hematopoietic lineage and hematopoietic stem cells (see Table 1) were cloned into the PiggyBac transposon-based expression vector under the control of the TET-inducible promoter (Ptight) (see FIG. 4A). A human H1 ESC line engineered to constitutively express rtTET protein under the control of the EF1α promoter at the ROSA26 locus (see FIG. 3) was used for transfection of PiggyBac vectors containing specific genes. Stable human ESCs with silent integrated genes were selected and maintained in medium containing Geneticin. To induce transgene expression, cells were treated with Doxycycline (DOX) (see FIG. 2).

ERG-3, GATA2, TAL1, and LMO2 were cloned into the PiggyBac vector (see FIG. 4A) under the control of the Ptight promoter and introduced by electroporation into the human ESC inducible line along with the hPBase-expressing vector. Transfected cells were cultured in mTeSR1 medium on matrigel in the presence of geneticin (100 μg/ml) for selection for stable genomic transgene integration. Doxycycline (0.2 μg/ml) was added to induce transgene expression, and the mTeSR1 was replaced with StemLine hematopoietic serum-free expansion medium (HSFM, Sigma) supplemented with 50 ng/ml SCF, 50 ng/ml TPO, 10 ng/ml FLT3L, 20 ng/ml IL-3 and 20 ng/ml IL-6 (all from Peprotech). Hematopoietic induction was observed as evidenced by the appearance of hematopoietic clusters with typical morphology, CD43+ cells, and colony-forming activity between day 4-6 post-induction.

FIG. 5A shows percentages of EMk (CD43+CD235a+CD41a+) and multipotent lineage negative (Lin−) CD43+CD45−/+ precursors and absolute numbers of colony-forming cells (CFCs) in cultures transfected with the indicated gene combinations. Multipotent CD43+Lin−CD45−/+ hematopoietic precursors and myeloid/multilineage CFCs (G/GM, GEMMk) were detected in gene combinations containing ERG-3 and GATA2. Combinations without ERG-3 (GATA2-TAL1 and GATA2-TAL1-LMO2) generated pre-committed EMk precursors, and the addition of TAL1 and/or LMO2 to the ERG-GATA2 combination accelerates differentiation toward EMk precursors.

FIG. 5B shows bright-field images of human ESCs transfected with indicated gene combinations. In the absence of Doxycycline induction (DOX−), no differentiation was observed up to day 6 in culture. In the presence of Doxycycline induction (DOX+), hematopoietic clusters and floating hematopoietic cells were first detectable on day 4 of induction, and became abundant on day 6 of induction. FIG. 5C shows flow cytometric analysis of human ESC cultures transfected with indicated gene combinations after 6 days of Doxycycline induction. Almost all (~95%) of the CD43+ cells generated in GATA2-TAL1-LMO2-transfected cultures were pre-committed EMk precursors (CD43+CD235a+CD41+), whereas ERG-GATA2-transfected cultures produced up to 10% multipotent CD43+Lin−CD45−/+ precursors.

As shown in FIG. 5, GATA2, in combination with two well known hematopoiesis-inductive factors TAL1 and LMO2 (Pimanda and Gottgens, 2010; Wilson et al., 2009) could induce hematopoietic differentiation. However, these cells were restricted to erythro-megakaryocytic (EMk) (CD43+CD235a+CD41a+) potential and essentially lacked cells of myeloid lineage. In the presence of ERG-3, GATA2 alone induced efficient hematopoietic differentiation. More importantly, multipotent CD43+Lin−CD45−/+ precursors along with myeloid/multilineage CFCs (G/GM and GEMMk) were readily detectable with this combination. The addition of TAL1 and/or LMO2 to ERG/GATA2 appeared to enhance the efficiency of EMk differentiation.

Efficient Programming of Human ESCs to Multipotent Hematopoietic Precursors Through ERG-3 and GFI1 Expression (FIG. 6).

Figure 6A:
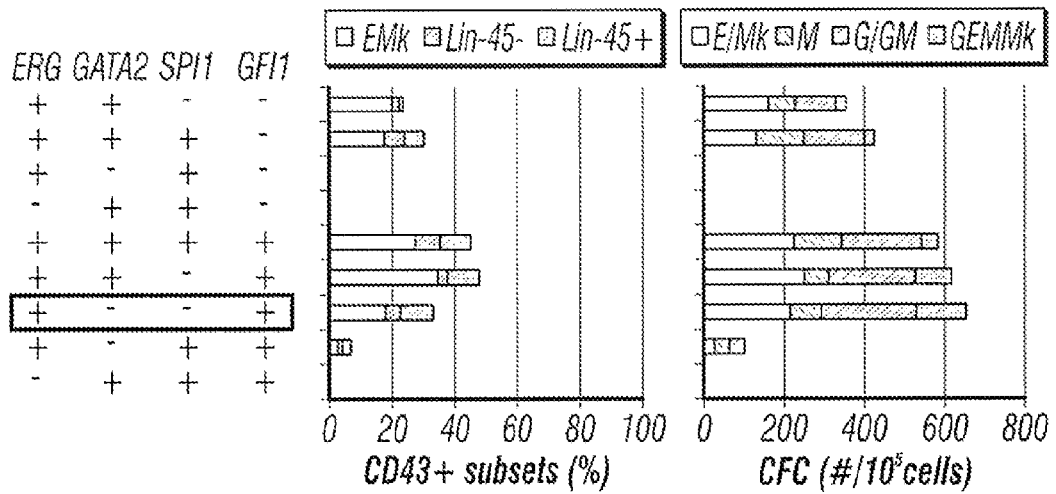
FIGS. 6A, 6B, 6C. Efficient programming of human ESCs to multipotent hematopoietic precursors through ERG and GFI1 expression. ERG, GATA2, SPI1 and GFI1 factors were tested for hematopoietic induction.
Figure 6B:
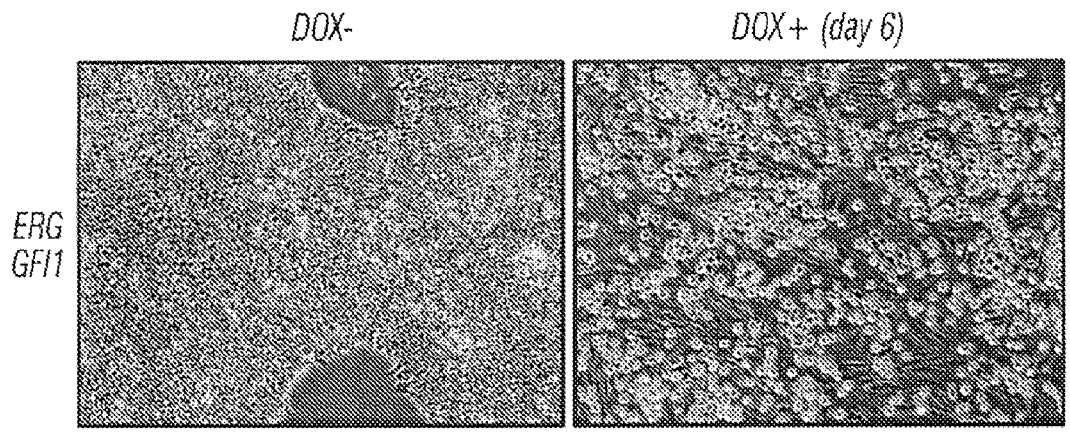
Figure 6C:
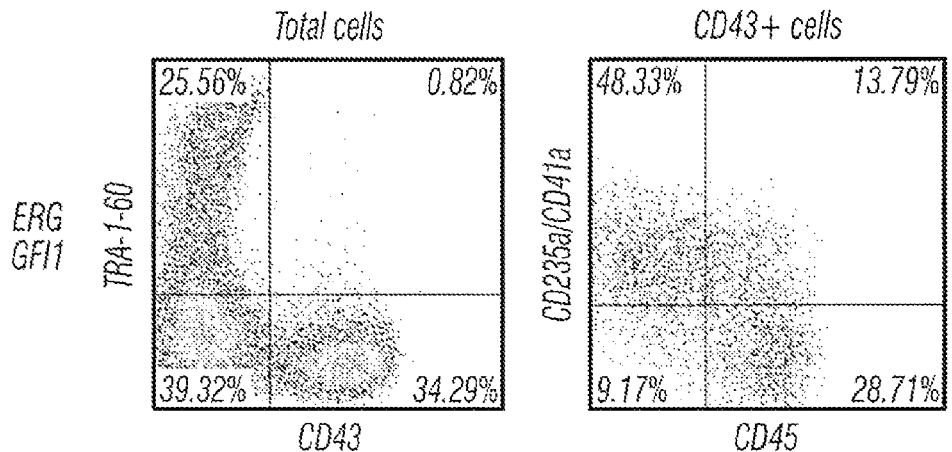
Figure 7:
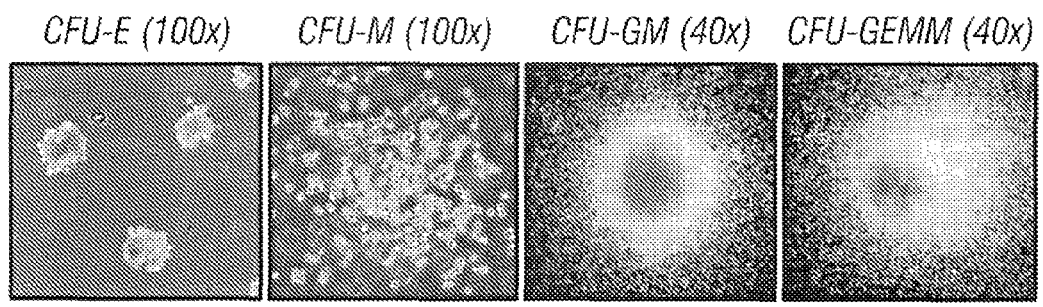
FIG. 7. Hematopoietic colonies formed by precursors generated through forward programming of human ESCs. Bright-field images show typical colonies. Magnifications are shown in parentheses.

ERG-3, GATA2, SPI1 and GFI1 factors were tested for hematopoietic induction. FIG. 6A shows the percentages of EMk (CD43+CD235a+CD41a+) and multipotent lineage negative (Lin−) CD43+CD45−/+ precursors, and absolute numbers of colony-forming cells (CFCs) in cultures transfected with indicated gene combinations. Multipotent CD43+Lin−CD45−/+ hematopoietic precursors and myeloid/multilineage CFCs (G/GM, GEMMk) were efficiently induced by ERG-3 and GFI1 genes. Addition of GATA2 and SPI1 factors promoted pre-committed EMk precursors. FIG. 6B shows bright-field images of human ESCs transfected with ERG-3 and GFI1. In the absence of Doxycycline induction (DOX−), no differentiation was observed up to day 6 in culture. In the presence of Doxycycline induction (DOX+), numerous hematopoietic clusters and abundant floating cells were observed on day 6 post-induction. FIG. 6C shows flow cytometric analysis of ERG/GFI1-transfected human ESC cultures after 6 days of Doxycycline induction. The ERG/GFI1 combination produced all types of hematopoietic precursors. FIG. 7 shows hematopoietic colonies formed by precursors generated through forward programming of human ESCs.

Although GATA2 appears to be important for the initiation of hematopoiesis in ERG-induced endothelial cells, its enforced expression may bias the hematopoietic differentiation to the EMk lineage. As shown in FIG. 6A, co-transfection of the myeloid SPI1 gene, which is a known GATA2 antagonist (Walsh et al., 2002), led to higher yield of multipotent CD43+Lin−CD45−/+ precursors and myeloid/multilineage CFCs (G/GM and GEMMk) (FIG. 7). These data suggest that the GATA2 expression level should be tightly regulated to allow the development of multilineage precursors.

In an attempt to identify alternative factors that may function as GATA2 inducers and promote autonomous balanced regulation of different hematopoietic differentiation programs, it was found that GFI1 factor may replace GATA2 for more efficient production of multipotent hematopoietic precursors in combination with ERG-3 (FIG. 6). The combination of ERG-3 and GFI1 enabled more balanced hematopoietic commitment to precursors with multilineage potential as demonstrated by the higher percentage of multipotent CD43+Lin−CD45−/+ precursors and a higher number of myeloid/multilineage CFCs (G/GM, GEMMk) (FIG. 6). The hemogenic cells induced by ERG-3 and GFI1 can likely give rise to other hematopoietic precursors and hematopoietic stem cells.

Forward programming of hematopoietic precursor cells from human ESCs/iPSCs is a rapid and efficient process. It bypasses most, if not all, intermediate developmental stages observed during normal in vitro human ESC/iPSC differentiation. This approach is a more time- and cost-efficient approach to generate human hematopoietic precursor cells and human hematopoietic stem cells with engraftment potential, as well as other hematopoietic cells.

Example 2

Transdifferentiation into Hematopoietic Precursor Cells

Figure 8:
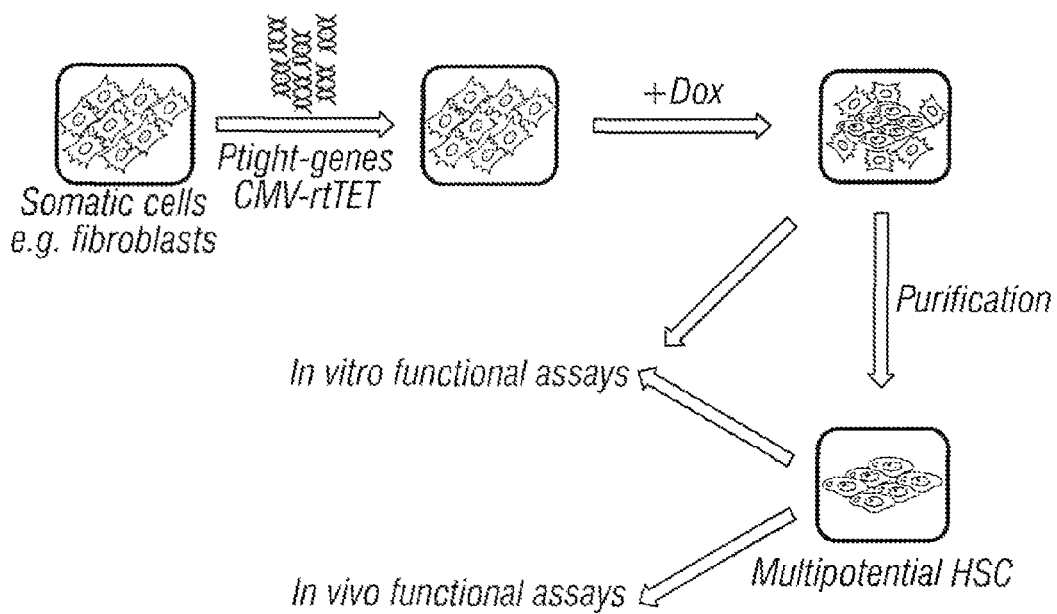
FIG. 8. The strategy to be employed for identifying transgene(s) to directly convert human somatic cells to hematopoietic cells. Human somatic cells will be cotransduced with lentivirus expressing rtTET protein (under the control of the CMV promoter) and transgenes (under the control of the Ptight inducible promoter). Upon Doxycycline (Dox) addition, transgene expression will be induced, and hematopoietic differentiation will be monitored by the characteristic hematopoietic cell morphology (e.g., cell clusters producing round non-adherent cells) and by flow cytometric detection of the total hematopoietic cell population by expression of the early pan-hematopoietic marker CD43 along with subpopulations of committed EMk (CD43+ CD235a+CD41a+) and lineage negative (Lin–) CD43+ CD45–/+ multipotent hematopoietic progenitors (Vodyanik et al., 2006). Different types of hematopoietic progenitors will also be determined by colony-forming assay.

Similar to forward programming, hematopoietic precursors may also be obtained via transdifferentiation from human somatic cells such as skin fibroblasts, adipose tissue-derived cells, and human umbilical vein endothelial cells (HUVEC) (FIG. 8). To identify genes that can convert fibroblasts to hematopoietic precursor cells, a lentiviral transgene delivery system will be used for the inducible expression of candidate genes (called the TET-ON system). Briefly, the cytomegalovirus (CMV) promoter will be used to drive the expression of the rtTET protein, and the candidate genes will be placed under the control of the rtTET-responsive inducible promoter (called Ptight). Both the rtTET and transgene-expressing lentivirus will be used to cotransduce fibroblasts. Doxycycline (0.2-1 µg/mL) will be added to the transduced fibroblasts to induce transgene expression, and the fibroblast cell culture medium will be replaced with hematopoietic cell culture medium to support programming.

The confirmation of hematopoietic precursors will be carried out similarly to forward programming from hESC/iPSCs and may include morphological characteristics, cell-surface marker expression and differentiation potential to erythroid-megakaryocytic, myeloid, and lymphoid lineages. Genes identified from forward programming from hESC/iPSCs, such as ERG-2, ERG-3, FLI1, ETV2, GATA2, GATA3, GFI1, GFI1B, TAL1 LYL1, LMO2 and SPI1 are strong candidates for use in the transdifferentiation of human somatic cells to hematopoietic precursors, although additional programming genes such as members of the OCT, KLF and MYC family may be needed to achieve optimal programming efficiency by destabilizing the established differentiated state in the human somatic cells.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and compositions disclosed herein. For example, variations may be applied in the steps or in the sequence of steps of methods described herein without departing from the concept, spirit and scope of the invention. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope, and concept of the invention as defined by the appended claims.

REFERENCES

The following references, to the extent that they provide exemplary procedural or other details supplementary to those set forth herein, are specifically incorporated herein by reference.

U.S. Pat. No. 4,683,202
U.S. Pat. No. 5,030,015
U.S. Pat. No. 5,302,523
U.S. Pat. No. 5,322,783
U.S. Pat. No. 5,384,253
U.S. Pat. No. 5,460,964
U.S. Pat. No. 5,464,765
U.S. Pat. No. 5,486,359
U.S. Pat. No. 5,538,877
U.S. Pat. No. 5,538,880
U.S. Pat. No. 5,550,318
U.S. Pat. No. 5,556,954
U.S. Pat. No. 5,563,055
U.S. Pat. No. 5,580,859

U.S. Pat. No. 5,589,466
U.S. Pat. No. 5,591,616
U.S. Pat. No. 5,610,042
U.S. Pat. No. 5,635,387
U.S. Pat. No. 5,656,610
U.S. Pat. No. 5,677,136
U.S. Pat. No. 5,681,599
U.S. Pat. No. 5,702,932
U.S. Pat. No. 5,716,827
U.S. Pat. No. 5,736,396
U.S. Pat. No. 5,736,524
U.S. Pat. No. 5,750,397
U.S. Pat. No. 5,759,793
U.S. Pat. No. 5,780,448
U.S. Pat. No. 5,789,215
U.S. Pat. No. 5,811,094
U.S. Pat. No. 5,827,735
U.S. Pat. No. 5,827,740
U.S. Pat. No. 5,837,539
U.S. Pat. No. 5,837,670
U.S. Pat. No. 5,843,780
U.S. Pat. No. 5,925,565
U.S. Pat. No. 5,928,906
U.S. Pat. No. 5,935,819
U.S. Pat. No. 5,945,100
U.S. Pat. No. 5,981,274
U.S. Pat. No. 5,994,136
U.S. Pat. No. 5,994,624
U.S. Pat. No. 6,013,516
U.S. Pat. No. 6,184,038
U.S. Pat. No. 6,833,269
U.S. Pat. No. 6,991,897
U.S. Pat. No. 7,015,037
U.S. Pat. No. 7,399,632
U.S. Pat. No. 7,410,773
U.S. Pat. No. 7,410,798
U.S. Pat. No. 7,422,736
U.S. Patent Publn. 2002/0055144
U.S. Patent Publn. 2002/0102265
U.S. Patent Publn. 2003/0040038
U.S. Patent Publn. 2003/0082561
U.S. Patent Publn. 2003/0211603
U.S. Patent Publn. 2004/0235175
U.S. Patent Publn. 2007/0072295
U.S. Patent Publn. 2007/0238170
U.S. Patent Publn. 2008/0260706
U.S. Patent Publn. 2009/0148425
U.S. application Ser. No. 08/464,599
U.S. application Ser. No. 61/058,858
U.S. application Ser. No. 61/172,079
U.S. application Ser. No. 61/184,546
Alexander et al., *Proc. Nat. Acad. Sci. USA*, 85:5092-5096, 1988.
Alison et al, *Hepatol.*, 29:678-83, 1998.
Amit et al., *Dev. Bio.*, 227:271-278, 2000.
Andrews et al., In: *Teratocarcinomas and Embryonic Stem Cells*, Robertson (Ed.), IRL Press, 207-246, 1987.
Asoh et al., *Proc. Natl. Acad. Sci. USA*, 99(26):17107-12, 2002.
Ausubel et al., *Current Protocols in Molecular Biology*, Greene Publ. Assoc. Inc. & John Wiley & Sons, Inc., MA, 1996.
Ausubel et al., In: *Current Protocols in Molecular Biology*, John, Wiley & Sons, Inc, New York, 1994.
Blomer et al., *J. Virol.*, 71(9):6641-6649, 1997.
Boczkowski et al., *Cancer Res.*, 60:1028-1034, 2001.
Boyer et al., *Cell*, 122(6):947-56, 2005.
Buss et al., *Mol. Cell. Biol.*, 8:3960-3963, 1988.
Byrne et al., *Nature*, 450(7169):497-502, 2007.
Capecchi, *Nature*, 348(6297):109, 1990.
Cassiede et al., *J. Bone Miner. Res.*, 11(9):1264-1273, 1996.
Cermak et al., *Nucleic Acids Res.*, 39(17):7879, 2011.
Chambers et al., *Cell*, 113(5):643-55, 2003.
Chen and Okayama, *Mol. Cell. Biol.*, 7(8):2745-2752, 1987.
Chevalier et al., *Prostaglandins Other Lipid Mediat.*, 70(1-2):31-37, 2002.
Christian et al., *Genetics*, 186(2):757-761, 2010.
*Current Protocols in Stem Cell Biology*, Bhatia et. al. (Ed.), John Wiley and Sons, Inc., 2007.
Derossi et al., *J. Bio. Chem.*, 269:10444-10450, 1994.
Derossi et al., *J. Biol. Chem.*, 271:18188, 1996.
Derossi et al., *Trends in Cell Biol.*, 8:84-87, 1998.
Durai et al., *Nucleic Acids Res.*, 33(18):5978-5990, 2005.
Elango et al., *Biochem. Biophys. Res. Comm.*, 330:958-966, 2005.
Elliott and O'Hare, *Cell*, 88:223-234, 1997.
EP 1507865
EP0412700
Ercolani et al., *J. Biol. Chem.*, 263:15335-15341, 1988.
Evans, et al., In: *Cancer Principles and Practice of Oncology*, Devita et al. (Eds.), Lippincot-Raven, NY, 1054-1087, 1997.
Fawell et al., *Proc. Natl. Acad. Sci. USA*, 91:664-668, 1994.
Fechheimer et al., *Proc Natl. Acad. Sci. USA*, 84:8463-8467, 1987.
Fraley et al., *Proc. Natl. Acad. Sci. USA*, 76:3348-3352, 1979.
Frankel and Pabo, *Cell*, 55(6):1189-1193, 1988.
Ghosh and Bachhawat, In: *Liver Diseases, Targeted Diagnosis and Therapy Using Specific Receptors and Ligands*, Wu et al. (Eds.), Marcel Dekker, NY, 87-104, 1991.
Gopal, *Mol. Cell. Biol.*, 5:1188-1190, 1985.
Graham and Van Der Eb, *Virology*, 52:456-467, 1973.
Gronthos, *Blood*, 84(12):41644173, 1994.
Hancock et al., *EMBO J.*, 10:4033-4039, 1991.
Harland and Weintraub, *J. Cell Biol.*, 101(3):1094-1099, 1985.
Hill et al., *Exp. Hematol.*, 24(8):936-943, 1996.
Ho et al., *Cancer Res.*, 61(2):474-7, 2001.
*In vitro Methods in Pharmaceutical Research*, Academic Press, 1997.
Jaiswal et al., *J Cell Biochem.*, 64(2):295-312, 1997.
Johnstone et al., 238(1):265-272, 1998.
Kaeppler et al., *Plant Cell Rep.*, 8:415-418, 1990.
Kaneda et al., *Science*, 243:375-378, 1989.
Karin et al. *Cell*, 36: 371-379, 1989.
Kato et al, *J. Biol. Chem.*, 266:3361-3364, 1991.
Kilic et al., *Stroke*, 34:1304-10, 2003.
Kirchmaier and Sugden, *J. Virol.*, 72(6):4657-4666, 1998.
Klein et al., *Nature*, 327:70-73, 1987.
Langle-Rouault et al., *J. Virol.*, 72(7):6181-6185, 1998.
Levitskaya et al., *Proc. Natl. Acad. Sci. USA*, 94(23):12616-12621, 1997.
Li et al., *Nucleic Acids Res.*, 39(14):6315-6325, 2011.
Lindgren et al., *Trends in Pharmacol. Sci.*, 21:99-103, 2000.
Lindner et. al., *J. Virol.*, 82(12):5693-702, 2008.
Macejak and Sarnow, *Nature*, 353:90-94, 1991.
Makino et al., *J. Clin. Invest.*, 103(5):697-705, 1999.
Maniatis, et al., *Molecular Cloning, A Laboratory Manual*, Cold Spring Harbor Press, Cold Spring Harbor, N.Y., 1988.
Mann and Frankel, *EMBO J.*, 10:1733-1739, 1991.
Mann et al., *Cell*, 33:153-159, 1983.
Miller et al., *Am. J. Clin. Oncol.*, 15(3):216-221, 1992.

Miller et al., *Nat. Biotechnol.*, 29(2):143-148, 2011.
Nabel et al., *Science*, 244(4910):1342-1344, 1989.
Naldini et al., *Science*, 272(5259):263-267, 1996.
Ng, *Nuc. Acid Res.*, 17:601-615, 1989.
Nicolas and Rubenstein, In: *Vectors: A survey of molecular cloning vectors and their uses*, Rodriguez and Denhardt, eds., Stoneham: Butterworth, pp. 494-513, 1988.
Nicolau and Sene, *Biochim. Biophys. Acta*, 721:185-190, 1982.
Nicolau et al., *Methods Enzymol.*, 149:157-176, 1987.
Oberlin et al., *Int. J. Dev. Biol. Sci.*, 54:1165, 2010.
Paskind et al., *Virology*, 67:242-248, 1975.
PCT Appln. PCT/US2004/030606
PCT Appln. PCT/IB2010/000154
PCT Appln. WO 03/042405
PCT Appln. WO 03/059940
PCT Appln. WO 03/059941
PCT Appln. WO 94/09699
PCT Appln. WO 95/06128
PCT Appln. WO 96/39487
PCT Appln. WO 99/20741
Pelletier and Sonenberg, *Nature*, 334:320-325, 1988.
Pimanda and Gottgens, *Int J. Dev. Biol. Sci.*, 54:1201, 2010.
Pingoud and Silva, *Nat. Biotechnol.*, 25(7):743-744, 2007.
Potrykus et al., *Mol. Gen. Genet.*, 199(2):169-177, 1985.
Potten, *Philos. Trans. R Soc. Lond. B Biol. Sci.*, 353:821-30, 1998.
Potter et al., *Proc. Natl. Acad. Sci. USA*, 81:7161-7165, 1984.
Quitsche et al., *J. Biol. Chem.*, 264:9539-9545, 1989.
Reubinoff et al., *Nat. Biotechnol.*, 18:399 B404, 2000.
Richards et al., *Cell*, 37: 263-272, 1984.
Rippe, et al., *Mol. Cell. Biol.*, 10:689-695, 1990.
Rothbard et al., *Nat. Med.*, 6(11):1253-7, 2000.
Sambrook and Russell, *Molecular Cloning: A Laboratory Manual*, 3rd Ed. Cold Spring Harbor Lab. Press, 2001.
Sambrook et al., In: *Molecular Cloning: A Laboratory Manual*, Vol. 1, Cold Spring Harbor Laboratory Press, Cold Spring Harbor, N.Y., (7)7:19-17.29, 1989.
Schwarze et al., *Science*, 285(5433):1466-7, 1999.
Schwarze et al., *Science*, 285:1569-1572, 1999.
Seaboe-Larssen et al., *J. Imm. Methods*, 259:191-203. 2002.
Silva et al., *Curr. Gene Ther.*, 11(1):11-27, 2011.
Smith, In: *Origins and Properties of Mouse Embryonic Stem Cells, Annu. Rev. Cell. Dev. Biol.*, 2000.
Takahashi and Yamanaka, *Cell*, 126:663-676, 2006.
Takahashi et al., *Cell*, 126(4):663-76, 2007.
Takahashi et al., *Cell*, 131:861-872, 2007.
Tanaka et al., *J. Immunol.*, 170(3):1291-8, 2003.
Temin, In: *Gene Transfer*, Kucherlapati (Ed.), NY, Plenum Press, 149-188, 1986.
Thomson and Marshall, *Curr. Top. Dev. Biol.*, 38:133-165, 1998.
Thomson and Odorico, *J. Trends. Biotechnol.*, 18:53 B57, 2000.
Thomson et al. *Proc. Natl. Acad. Scie. USA*, 92:7844-7848, 1995.
Thomson et al., *Science*, 282:1145, 1998.
Tur-Kaspa et al., *Mol. Cell. Biol.*, 6:716-718, 1986.
Vodyanik et al., *Blood*, 108:2095, 2006.
Walsh et al., *Immunity*, 17:665, 2002.
Watt, *Philos. Trans. R. Soc. Lond. B. Biol. Sci.*, 353:831, 1997.
Weber et al., *PLoS One*, 6(5):e19722, 2011.
Wender et al., *Proc. Natl. Acad. Sci. USA*, 97(24):13003-8, 2000.
Wilson et al., *Blood*, 113:5456, 2009.
Wilson et al., *Mol. Cell. Biol.*, 30:3853, 2010.
Wilson et al., *Science*, 244:1344-1346, 1989.
Wong et al., *Gene*, 10:87-94, 1980.
Wu and Wu, *Biochemistry*, 27: 887-892, 1988.
Wu and Wu, *J. Biol. Chem.*, 262:4429-4432, 1987.
Xu et al., *Nat. Biotechnol.*, 19:971-974, 2001.
Yang and Russell, *Proc. Natl. Acad. Sci. USA*, 87:4144-4148, 1990.
Ying et al., *Cell*, 115:281-292, 2003.
Yoo et al., *J. Bone Joint Sure. Am.*, 80(12):1745-1757, 1998.
Yu and Thompson, *Genes Dev.*, 22(15):1987-97, 2008.
Yu et al., *Science*, 318:1917-1920, 2007.
Yu et al., *Science*, 324(5928):797-801, 2009.
Zhang et al., *Nat. Biotechnol.*, 29(2):149-153, 2011.
Zufferey et al., *Nat. Biotechnol.*, 15(9):871-875, 1997.

What is claimed is:

1. An in vitro method of providing human hematopoietic precursor cells by forward programming of human induced pluripotent stem cells, the method comprising:
providing the hematopoietic precursor cells by culturing the induced pluripotent stem cells under conditions to increase the expression level of one or more hematopoietic precursor programming factor gene capable of causing forward programming of the induced pluripotent stem cells into hematopoietic precursor cells, thereby forward programming the induced pluripotent stem cells into hematopoietic precursor cells, wherein the culturing is performed in the absence of bone marrow stromal cells, wherein the one or more hematopoietic precursor programming factor genes is under the control of a heterologous promoter, wherein the at least one hematopoietic precursor programming factor gene comprises an endothelial differentiation factor gene selected from the group consisting of ERG (v-ets erythroblastosis virus E26 oncogene homolog (avian)), FLI-1 (Friend leukemia virus integration 1), and ETV2 (ets variant 2); or comprises a hematopoietic precursor programming factor gene selected from the group consisting of GFI1 (growth factor independent 1 transcription repressor), GFI1B (growth factor independent 1B transcription repressor), TAL1 (T-cell acute lymphocytic leukemia), LYL1 (lymphoblastic leukemia derived sequence 1), LMO2 (LIM domain only 2 (rhombotin-like 1)), GATA2 (GATA binding protein 2), GATA3 (GATA binding protein 3), and SPI1 (spleen focus forming virus (SFFP) proviral integration oncogene spi1).

2. The method of claim 1, wherein the hematopoietic precursor cells are provided by forward programming of induced pluripotent stem cells.

3. The method of claim 1, wherein at least one hematopoietic precursor programming factor gene comprises an endothelial differentiation factor gene.

4. The method of claim 3, wherein the at least one endothelial differentiation factor comprises ERG (v-ets erythroblastosis virus E26 oncogene homolog (avian)), FLI-1 (Friend leukemia virus integration 1), or ETV2 (ets variant 2).

5. The method of claim 4, wherein at least one endothelial differentiation factor is ERG.

6. The method of claim 5, wherein the ERG is ERG-2 or ERG-3.

7. The method of claim 1, wherein the heterologous promoter is an inducible promoter.

* * * * *